US009926345B2

(12) United States Patent
Melnyk et al.

(10) Patent No.: US 9,926,345 B2
(45) Date of Patent: Mar. 27, 2018

(54) COMPOSITIONS AND METHODS FOR TREATING OR PREVENTING *CLOSTRIDIUM* INFECTION

(71) Applicants: THE HOSPITAL FOR SICK CHILDREN, Toronto (CA); VANDERBILT UNIVERSITY, Nashville, TN (US)

(72) Inventors: Roman Melnyk, Oakville (CA); Zhifen Zhang, Toronto (CA); John Tam, Markham (CA); Dana Borden Lacy, Nashville, TN (US); Stacey A. Seeback, Greenbier, TN (US); Nicole M. Chumbler, Stockbridge, TN (US)

(73) Assignees: THE HOSPITAL FOR SICK CHILDREN, Toronto, Ontario (CA); VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/119,323

(22) PCT Filed: Feb. 17, 2015

(86) PCT No.: PCT/CA2015/050115
§ 371 (c)(1),
(2) Date: Aug. 16, 2016

(87) PCT Pub. No.: WO2015/123767
PCT Pub. Date: Aug. 27, 2015

(65) Prior Publication Data
US 2017/0008937 A1 Jan. 12, 2017

Related U.S. Application Data

(60) Provisional application No. 61/941,090, filed on Feb. 18, 2014, provisional application No. 62/076,689, filed on Nov. 7, 2014.

(51) Int. Cl.
*A61K 39/08* (2006.01)
*A61K 39/02* (2006.01)
*A61K 39/00* (2006.01)
*C07K 14/33* (2006.01)
*A61K 38/00* (2006.01)

(52) U.S. Cl.
CPC .............. *C07K 14/33* (2013.01); *A61K 39/08* (2013.01); *A61K 38/00* (2013.01); *A61K 2039/522* (2013.01); *G01N 2333/33* (2013.01); *G01N 2469/20* (2013.01)

(58) Field of Classification Search
CPC ........ A61K 38/00; A61K 38/04; A61K 38/16; A61K 39/00; A61K 39/02; A61K 39/08
USPC ..................... 424/184.1, 185.1, 234.1, 247.1
See application file for complete search history.

(56) References Cited

U.S. PATENT DOCUMENTS

2005/0238665 A1* 10/2005 Williams ............. C07K 14/245
424/239.1
2012/0276132 A1 11/2012 Feng et al.

FOREIGN PATENT DOCUMENTS

CA         2782406 A1     6/2011
WO   WO-2013038156 A1    3/2013

OTHER PUBLICATIONS

Barth, H., et al. (2001), "Low pH-induced Formation of Ion Channels by Clostridium difficile Toxin B in Target Cells", *The Journal of Biological Chemistry*, 276(14): 10670-10676.
Burger, S., et al. (2003), "Expression of recombinant Clostridium difficile toxin A using the Bacillus megaterium system", *Biochemical and Biophysical Research Communications*, 307: 584-588.
Choe, S., et al. (1992), "The crystal structure of diptheria toxin", *Nature*, 357: 216-222.
Chumbler, N., et al. (2012), "Clostridium difficile Toxin B causes epithelial cell necrosis through an autoprocessing-independent mechanism", *PLOS Pathog*, 8(12): e1003072.
Collier, R., (2001), "Understanding the mode of action of diptheria toxin: a perspective on progress during the 20th Century", *Toxicon*, 39: 1793-1803.
Collier, R., (2009), "Membrane translocation by anthrax toxin", *Mol Aspects Med*, 30(6): 413-422.
Deleers, M., et al. (1983), "Localization in diptheria toxin fragment B of a region that induces pore formation in planar lipid bilayers at Low pH", *FEBS*, 160(1-2): 82-86.
Donta, I., et al. (1982), "Effect of Beta-Andrenergic Blockade on Physiologic Growth in the Wistar Rat", *Research Communications in Chemical Pathology and Pharmacology*, 37(1): 147-150.
Eichel-Streiber, C., et al. (1992), "Comparative sequence analysis of the Clostridium difficile toxins A and B", *Mol Gen Genet*, 233: 260-268.
Farrow, M., et al. (2013), "Clostridium difficile toxin B-induced necrosis is mediated by the host epithelial cell NADPH oxidase complex", *PNAS*, 110(46): 18674-18679.
Genisyuerek, S., et al. (2011), "Structural determinants for membrane insertion, pore formation and translocation of Clostridium difficile toxin B", *Molecular Microbiology*, 79(6): 1643-1654.
Genth, H., et al. (1999), "Monoglucosylation of Rhoa at Threonine 37 Blocks Cytosol-Membrane Cycling", *The Journal of Biological Chemistry*, 274(41): 29050-29056.

(Continued)

*Primary Examiner* — Rodney P Swartz
(74) *Attorney, Agent, or Firm* — Harness, Dickey and Pierce, P.L.C.

(57) ABSTRACT

*Clostridium difficile* is a leading cause of antibiotic-associated infection in hospitals worldwide. There is a need for a vaccine to *Clostridium difficile* that can target toxic proteins, or that can elicit adequate immunity to prevent infection or reduce the severity of infection. Modified *Clostridium difficile* toxin A and B (TcdA and TcdB) proteins are described herein, which comprise mutations that reduce toxin A and B toxicity compared to the native toxin. The proteins described are highly similar to the native toxin of *Clostridium difficile*, but toxicity is reduced.

14 Claims, 15 Drawing Sheets

(56) References Cited

OTHER PUBLICATIONS

Hippenstiel, S., et al. (2002), "Rho Protein inactivation induced apoptosis of cultured human endothelial cells", *Am J Physiol Lung Cell Mol Physiol*, 283: L830-L838.

Ho, J., et al. (2005), "Crystal Structure of receptor-binding C-terminal repeats from Clostridium difficile toxin A", *PNAS*, 102(51): 18373-18378.

Hundsberger, T., et al. (1997), "Transcription Analysis of the Genes tcdA-E of the pathogenicity locus of Clostridium difficile", *Eur. J. Biochem*, 244: 735-742.

International Preliminary Report on Patentability for Application No. PCT/CA2015/050115, dated Sep. 1, 2016, 9 pages.

International Search Report for Application No. PCT/CA2015/050115, dated May 4, 2015, 6 pages.

Johnson, V., et al. (1993), "The Role of Proline 345 in Diptheria Toxin Translocation", *The Journal of Biological Chemistry*, 268(5): 3514-3519.

Just, I., et al. (1995), "The Low Molecular Mass GTP-binding Protein Rho is Affected by Toxin A from Clostridium difficile", *J. Clin. Invest.*, 95: 1026-1031.

Kabsch, W. (2010), "XDS", *Acta Cryst.*, 66: 125-132.

Kaul, P., et al. (1996), "Roles of Glu 349 and Asp 352 in membrane insertion and translocation by diptheria toxin", *Protein Science*, 5: 687-692.

Kelly, C., et al. (2008), "Clostridium difficile—More Difficult Than Ever", *The New England Journal of Medicine*, 359: 1932-1940.

Kreimeyer, I., et al. (2011), "Autoproteolytic cleavage mediates cytotoxicity of Clostridium difficile toxin A", *Naunyn-Schmied Arch Pharmacol*, 383: 253-262.

Krogh, A., et al. (2001), "Predicting Transmembrane Protein Topology with a Hidden Markov Model: Application to Complete Genomes", *J. Mol.Biol.*, 305: 567-580.

Lanis, J., et al. (2010), "Variations in TcdB Activity and the Hypervirulence of Emerging Strains of Clostridium difficile", *PLosPathog*, 6(8): e1001061.

Melnyk, R., et al. (2006), "A Loop network within the anthrax toxin pore positions the phenylalanine clamp in an active conformation", *PNAS*, 103(26): 9802-9807.

Murase, T., et al. (2014), "Structural Basis for Antibody Reognition in the Receptor-binding Domains of Toxins A and B from Clostridium difficile", *The Journal of Biological Chemistry*, 289(4): 2331-2343.

Olling, A., et al. (2011), "The Repetitive Oligopeptide Sequences Modulate Cytopathic Potency but Are Not Crucial for Cellular Uptake of Clostridium difficile Toxin A", *PLoSONE*, 6(3): e17623.

Papatheodorou, P., et al. (2010), "Clostridial Glucosylating Toxins Enter Cells via Clathrin-Mediated Endocytosis", *PLoSONE*, 5(5): e10673.

Pruitt, R., et al. (2010), "Structural organization of the functional domains of Clostridium difficile toxins A and B", *PNAS*, 107(30): 13467-13472.

Pruitt, R., et al. (2012), "Structural Determinants of Clostridium difficile Toxin A Glucosyltransferase Activity", *The Journal of Biological Chemistry*, 287(11): 8013-8020.

Qa'dan, M., et al. (2000), "pH-Induced Conformational Changes in Clostridium difficile Toxin B", *Infection and Immunity*, 68(5): 2470-2474.

Reineke, J., et al. (2007), "Autocatalytic cleavage of Clostridium difficile toxin B", *Nature*, 446: 415-419.

Reinert, D., etal. (2005), "Structural Basis for the Function of Clostridium Difficile Toxin B", *J. Mol. Biol.*, 351: 973-981.

Ren, J., et al. (1999), "Interaction of Diptheria Toxin T Domain with Molten Globule-Like Proteins and Its Implications for Translocation", *Science*, 284: 955-957.

Shen, A., et al. (2011), "Defining an allosteric circuit in the cysteine protease domain of Clostridium difficile toxins", *Nature Structural & Molecular Biology*, 364-371.

Silverman, J., et al. (1994), "Mutational Analysis of the Helical Hairpin Region of Diptheria Toxin Transmembrane Domain", *The Journal of Biological Chemistry*, 269(36): 22524-22532.

Wang, J., et al. (2009), "The Membrane Topography of Diptheria Toxin T Domain Linked to the A Chain Reveals a Transient Transmembrane Hairpin and Potential Translocation Mechanisms", *Biochemistry*, 48(43): 10446-10456.

Wang, Y., et al. (1997), "Identification of Shallow and Deep Membrane-penetrating Forms of Diptheria Toxin T Domain That are Regulated by Protein Concentration and Bilayer Width", *The Journal of Biological Chemistry*, 272(40): 25091-25098.

Written Opinion for Application No. PCT/CA2015/050115, dated May 4, 2015, 8 pages.

Yang, G., et al. (2008), "Expression of recombinant Clostridium difficile toxin A and B in Bacillus megaterium", *BMC Microbiology*, 8(192): 1-13.

Zhang, Y., et al. (2013), "A Segment of 97 Amino Acids within the Translocation Domain of Clostridium difficile Toxin B is Essential for Toxicity", *PLoS ONE*, 8(3): e58634.

Zhang, Z., et al. (2014), "Translocation domain mutations affecting cellular toxicity identify the Clostridium difficile Toxin B pore", *PNAS*, 111(10): 3721-3726.

Ziegler, M., et al. (2007), "Conformational Changes and Reaction of Clostridial Glcosylating Toxins", *J. Mol. Biol.*, 377: 1346-1356.

\* cited by examiner

WT TcdB protein sequence (SEQ ID NO: 1)

```
MSLVNRKQLEKMANVRFRTQEDEYVAILDALEEYHNMSENTVVEKYLKLKDINSLTDIYI
DTYKKSGRNKALKKFKEYLVTEVLELKNNNLTPVEKNLHFVWIGGQINDTAINYINQWKD
VNSDYNVNVFYDSNAFLINTLKKTVVESAINDTLESFRENLNDPRFDYNKFFRKRMEIIY
DKQKNFINYYKAQREENPELIIDDIVKTYLSNEYSKEIDELNTYIEESLNKITQNSGNDV
RNFEEFKNGESFNLYEQELVERWNLAAASDILRISALKEIGGMYLDVDMLPGIQPDLFES
IEKPSSVTVDFWEMTKLEAIMKYKEYIPEYTSEHFDMLDEEVQSSFESVLASKSDKSEIF
SSLGDMEASPLEVKIAFNSKGIINQGLISVKDSYCSNLIVKQIENRYKILNNSLNPAISE
DNDFNTTTNTFIDSIMAEANADNGRFMMELGKYLRVGFFPDVKTTINLSGPEAYAAAYQD
LLMFKEGSMNIHLIEADLRNFEISKTNISQSTEQEMASLWSFDDARAKAQFEEYKRNYFE
GSLGEDDNLDFSQNIVVDKEYLLEKISSLARSSERGYIHYIVQLQGDKISYEAACNLFAK
TPYDSVLFQKNIEDSEIAYYYNPGDGEIQEIDKYKIPSIISDRPKIKLTFIGHGKDEFNT
DIFAGFDVDSLSTEIEAAIDLAKEDISPKSIEINLLGCNMFSYSINVEETYPGKLLLKVK
DKISELMPSISQDSIIVSANQYEVRINSEGRRELLDHSGEWINKEESIIKDISSKEYISF
NPKENKITVKSKNLPELSTLLQEIRNNSNSSDIELEEKVMLTECEINVISNIDTQIVEER
IEEAKNLTSDSINYIKDEFKLIESISDALCDLKQQNELEDSHFISFEDISETDEGFSIRF
INKETGESIFVETEKTIFSEYANHITEEISKIKGTIFDTVNGKLVKKVNLDTTHEVNTLN
AAFFIQSLIEYNSSKESLSNLSVAMKVQVYAQLFSTGLNTITDAAKVVELVSTALDETID
LLPTLSEGLPIIATIIDGVSLGAAIKELSETSDPLLRQEIEAKIGIMAVNLTTATTAIIT
SSLGIASGFSILLVPLAGISAGIPSLVNNELVLRDKATKVVDYFKHVSLVETEGVFTLLD
DKIMMPQDDLVISEIDFNNNSIVLGKCEIWRMEGGSGHTVTDDIDHFFSAPSITYREPHL
SIYDVLEVQKEELDLSKDLMVLPNAPNRVFAWETGWTPGLRSLENDGTKLLDRIRDNYEG
EFYWRYFAFIADALITTLKPRYEDTNIRINLDSNTRSFIVPIITTEYIREKLSYSFYGSG
GTYALSLSQYNMGINIELSESDVWIIDVDNVVRDVTIESDKIKKGDLIEGILSTLSIEEN
KIILNSHEINFSGEVNGSNGFVSLTFSILEGINAIIEVDLLSKSYKLLISGELKILMLNS
NHIQQKIDYIGFNSELQKNIPYSFVDSEGKENGFINGSTKEGLFVSELPDVVLISKVYMD
DSKPSFGYYSNNLKDVKVITKDNVNILTGYYLKDDIKISLSLTLQDEKTIKLNSVHLDES
GVAEILKFMNRKGNTNTSDSLMSFLESMNIKSIFVNFLQSNIKFILDANFIISGTTSIGQ
FEFICDENDNIQPYFIKFNTLETNYTLYVGNRQNMIVEPNYDLDDSGDISSTVINFSQKY
LYGIDSCVNKVVISPNIYTDEINITPVYETNNTYPEVIVLDANYINEKINVNINDLSIRY
VWSNDGNDFILMSTSEENKVSQVKIRFVNVFKDKTLANKLSFNFSDKQDVPVSEIILSFT
PSYYEDGLIGYDLGLVSLYNEKFYINNFGMMVSGLIYINDSLYYFKPPVNNLITGFVTVG
DDKYYFNPINGGAASIGETIIDDKNYYFNQSGVLQTGVFSTEDGFKYFAPANTLDENLEG
EAIDFTGKLIIDENIYYFDDNYRGAVEWKELDGEMHYFSPETGKAFKGLNQIGDYKYYFN
SDGVMQKGFVSINDNKHYFDDSGVMKVGYTEIDGKHFYFAENGEMQIGVFNTEDGFKYFA
HHNEDLGNEEGEEISYSGILNFNNKIYYFDDSFTAVVGWKDLEDGSKYYFDEDTAEAYIG
LSLINDGQYYFNDDGIMQVGFVTINDKVFYFSDSGIIESGVQNIDDNYFYIDDNGIVQIG
VFDTSDGYKYFAPANTVNDNIYGQAVEYSGLVRVGEDVYYFGETYTIETGWIYDMENESD
KYYFNPETKKACKGINLIDDIKYYFDEKGIMRTGLISFENNNYYFNENGEMQFGYINIED
KMFYFGEDGVMQIGVFNTPDGFKYFAHQNTLDENFEGESINYTGWLDLDEKRYYFTDEYI
AATGSVIIDGEEYYFDPDTAQLVISEHHHHHH-
```

FIG. 1

TcdB - L1106K protein sequence (SEQ ID NO:2)

```
MSLVNRKQLEKMANVRFRT

TcdB - WT Nucleotide Sequence (part 1 of 2 for SEQ ID NO:3)

ATGAGCCTGGTCAACCGTAAACAACTGGAAAAAATGGCAAATGTCCGCTTTCGCACCCAAGAAGATGAATATGTC
GCAATCCTGGACGCGCTGGAAGAATACCATAACATGAGCGAAAATACCGTGGTTGAAAAGTACCTGAAGCTGAAG
GATATCAACTCCCTGACCGATATTTACATCGACACGTATAAAAAGTCAGGCCGTAACAAGGCACTGAAAAAGTTC
AAGGAATATCTGGTGACCGAAGTTCTGGAACTGAAGAACAATAACCTGACGCCGGTTGAAAAGAACCTGCACTTC
GTCTGGATTGGCGGTCAGATCAACGATACCGCTATCAACTACATCAACCAATGGAAGGATGTGAACTCCGACTAC
AACGTGAACGTGTTTTATGATTCAAACGCATTCCTGATCAACACCCTGAAAAAGACGGTCGTGGAATCTGCTATC
AATGATACCCTGGAAAGTTTTCGTGAAAATCTGAACGATCCGCGCTTCGACTACAACAAGTTTTTCCGTAAGCGC
ATGGAAATCATCTACGATAAGCAGAAGAACTTCATCAACTACTACAAGGCGCAACGTGAAGAAAATCCGGAACTG
ATTATCGATGACATCGTGAAGACCTACCTGAGCAACGAATACTCTAAGGAAATCGATGAACTGAACACCTACATT
GAAGAATCCCTGAACAAAATCACGCAGAACTCAGGCAACGATGTTCGCAACTTCGAAGAATTCAAGAACGGTGAA
AGCTTTAACCTGTATGAACAAGAACTGGTGGAACGTTGGAACCTGGCGGCCGCATCAGATATTCTGCGCATCTCG
GCCCTGAAAGAAATTGGCGGTATGTATCTGGATGTTGACATGCTGCCGGGCATTCAGCCGGACCTGTTTGAATCT
ATCGAAAAACCGAGCTCTGTCACCGTGGATTTCTGGGAAATGACGAAACTGGAAGCGATTATGAAATACAAGGAA
TATATCCCGGAATATACCAGTGAACATTTTGATATGCTGGACGAAGAAGTGCAGAGTTCCTTCGAATCCGTTCTG
GCCAGCAAGTCCGACAAATCAGAAATTTTTAGCAGCCTGGGTGATATGGAAGCGTCGCCGCTGGAAGTGAAGATT
GCCTTCAACAGCAAAGGTATTATCAATCAGGGCCTGATCTCTGTCAAAGATAGCTACTGCTCTAATCTGATTGTG
AAGCAAATCGAAAACCGTTACAAGATCCTGAACAACAGCCTGAATCCGGCAATTTCTGAAGATAACGACTTTAAT
ACCACGACCAACACCTTCATTGACAGCATCATGGCGGAAGCCAACGCAGATAATGGCCGTTTTATGATGGAACTG
GGCAAGTATCTGCGCGTGGGCTTTTTCCCGGATGTTAAAACGACCATTAATCTGTCTGGTCCGGAAGCATACGCT
GCAGCATATCAGGATCTGCTGATGTTTAAAGAAGGTTCAATGAACATTCACCTGATCGAAGCAGATCTGCGCAAC
TTCGAAATCTCGAAAACCAATATTTCACAGTCGACGGAACAAGAAATGGCTAGTCTGTGGTCCTTTGATGACGCT
CGTGCGAAGGCCCAGTTCGAAGAATACAAGCGCAACTACTTCGAAGGCAGTCTGGGTGAAGATGACAACCTGGAC
TTCTCCCAAAATATTGTTGTCGATAAGGAATATCTGCTGGAAAAAATCAGCTCTCTGGCGCGTAGTTCCGAACGC
GGCTACATTCATTATATCGTTCAGCTGCAAGGTGATAAAATTAGCTACGAAGCAGCTTGCAACCTGTTTGCAAAG
ACCCCGTATGACTCAGTGCTGTTCCAGAAAAATATCGAAGATTCGGAAATCGCTTACTACTATAACCCGGGCGAC
GGTGAAATCCAAGAAATCGATAAGTACAAGATCCCGTCAATCATCTCGGATCGTCCGAAAATCAAGCTGACCTTT
ATTGGCCACGGTAAAGATGAATTCAATACGGACATTTTTGCGGGCTTCGATGTGGACAGCCTGTCTACCGAAATT
GAAGCGGCCATCGATCTGGCCAAGGAAGACATTAGCCCGAAATCTATTGAAATCAATCTGCTGGGCTGTAACATG
TTTAGTTACTCCATCAACGTGGAAGAAACCTATCCGGGTAAACTGCTGCTGAAAGTTAAGGACAAAATTTCAGAA
CTGATGCCGTCAATCTCGCAGGATAGTATTATCGTCTCCGCCAACCAATATGAAGTGCGCATTAATTCTGAAGGC
CGTCGCGAACTGCTGGATCATTCGGGTGAATGGATCAACAAAGAAGAAAGCATCATCAAGGATATCTCATCGAAG
GAATACATCAGCTTCAACCCGAAGGAAAACAAGATCACCGTGAAGTCCAAGAACCTGCCGGAACTGTCAACGCTG
CTGCAGGAAATCCGTAATAACAGTAACAGCTCTGATATTGAACTGGAAGAAAAAGTGATGCTGACCGAATGCGAA
ATTAACGTTATCTCCAATATTGATACGCAGATCGTCGAAGAACGCATTGAAGAAGCGAAAAACCTGACCAGCGAC
TCTATTAACTACATCAAGGATGAATTCAAGCTGATCGAAAGTATTTCCGATGCCCTGTGTGACCTGAAACAGCAA
AACGAACTGGAAGATTCACACTTTATCTCGTTCGAAGATATTTCGGAAACCGACGAAGGCTTTAGCATCCGCTTC
ATCAACAAGGAAACGGGTGAATCAATCTTCGTGGAAACGGAAAAAACCATCTTCTCGGAATATGCGAACCATATT
ACCGAAGAAATCAGCAAGATTAAAGGCACCATTTTTGACACGGTTAATGGTAAACTGGTCAAAAAGGTGAACCTG
GATACGACCCACGAAGTCAACACCCTGAATGCAGCGTTTTTCATTCAGAGCCTGATCGAATACAATAGTTCCAAG
GAATCACTGTCGAACCTGTCGGTTGCAATGAAAGTTCAGGTCTATGCTCAACTGTTTAGCACCGGCCTGAATACG
ATTACCGATGCGGCCAAAGTGGTTGAACTGGTGTCTACCGCGCTGGATGAAACGATCGACCTGCTGCCGACCCTG
AGTGAAGGTCTGCCGATTATCGCCACGATTATCGATGGCGTTTCCCTGGGTGCAGCTATTAAAGAACTGAGTGAA
ACCTCCGATCCGCTGCTGCGTCAGGAAATCGAAGCAAAAATTGGCATCATGGCTGTTAACCTGACGACCGCAACG
ACCGCTATTATCACGTCATCGCTGGGCATCGCATCAGGTTTTTCGATTCTGCTGGTGCCGCTGGCAGGTATTAGT
GCAGGTATCCCGTCCCTGGTTAATAACGAACTGGTCCTGCGCGACAAGGCTACCAAAGTCGTGGATTATTTTAAA
CATGTTAGCCTGGTCGAAACCGAGGGTGTGTTCACGCTGCTGGATGACAAAATTATGATGCCGCAGGATGACCTG
GTCATCTCGGAAATCGATTTCAACAACAACAGCATTGTGCTGGGCAAATGTGAAATCTGGCGTATGGAAGGCGGT
AGCGGTCATACGGTTACCGATGACATCGATCACTTTTTCAGCGCGCCGTCTATTACCTACCGCGAACCGCACCTG
AGCATCTATGATGTGCTGGAAGTTCAGAAGGAAGAACTGGATCTGTCTAAAGACCTGATGGTCCTGCCGAACGCG
CCGAATCGTGTGTTTGCCTGGGAAACGGGTTGGACCCCGGGTCTGCGTAGCCTGGAAAATGATGGCACCAAACTG
CTGGATCGTATTCGCGACAACTACGAGGGTGAATTCTACTGGCGTTATTTTGCCTTCATCGCAGATGCTCTGATT
ACGACCCTGAAACCGCGTTATGAAGACACCAACATTCGCATCAATCTGGATAGCAACACGCGTTCTTTTATTGTG
CCGATTATCACGACCGAATATATCCGCGAAAAACTGAGCTACTCTTTCTATGGCAGCGGCGGTACCTACGCACTG
AGTCTGTCCCAGTATAATATGGGTATTAACATCGAACTGTCAGAATCGGATGTGTGGATTATCGATGTTGACAAT
GTTGTCCGCGATGTTACCATCGAAAGCGACAAAATTAAAAAGGGTGATCTGATCGAAGGCATTCTGAGTACGCTG
TCCATCGAAGAAAACAAGATCATCCTGAACAGTCATGAAATCAATTTTAGCGGCGAAGTTAACGGCTCAAATGGT
TTTGTCAGTCTGACCTTCTCCATTCTGGAAGGTATCAACGCCATTATCGAAGTGGATCTGCTGAGCAAGTCTTAT

FIG 3A

TcdB - WT Nucleotide Sequence (part 2 of 2 for SEQ ID NO:3)

```
AAACTGCTGATCAGCGGCGAACTGAAGATTCTGATGCTGAATTCTAACCACATCCAGCAAAAGATCGATTACATC
GGTTTCAACAGCGAACTGCAGAAGAATATCCCGTACTCATTCGTTGATTCGGAAGGCAAGGAAAATGGTTTCATC
AACGGCTCTACCAAAGAAGGCCTGTTTGTTAGTGAACTGCCGGATGTGGTTCTGATTAGTAAGGTCTATATGGAT
GACTCAAAACCGTCGTTTGGCTACTATTCCAACAATCTGAAGGACGTGAAGGTTATCACCAAGGATAACGTGAAC
ATCCTGACGGGTTACTATCTGAAGGATGACATTAAAATCAGTCTGTCCCTGACCCTGCAGGACGAAAAGACGATT
AAACTGAATTCGGTGCATCTGGATGAAAGCGGCGTTGCAGAAATCCTGAAGTTTATGAACCGTAAAGGTAATACG
AACACCTCAGATTCGCTGATGAGCTTCCTGGAATCTATGAACATCAAGTCCATCTTCGTTAACTTCCTGCAGTCA
AATATCAAGTTTATTCTGGATGCGAACTTCATTATCAGTGGTACGACCTCCATCGGCCAGTTTGAATTCATTTGC
GATGAAAATGACAACATCCAACCGTACTTTATTAAATTCAACACGCTGGAAACCAATTACACGCTGTATGTTGGT
AACCGCCAGAATATGATTGTCGAACCGAATTATGACCTGGATGACTCTGGCGATATCAGCTCTACCGTCATTAAC
TTTAGTCAAAAGTACCTGTATGGTATTGATTCGTGTGTGAACAAAGTCGTGATTAGCCCGAATATCTATACCGAT
GAAATTAACATCACGCCCGGTGTACGAAACCAACAATACGTATCCGGAAGTCATTGTGCTGGACGCGAACTACATC
AACGAAAAGATCAACGTTAACATCAACGATCTGTCTATCCGTTATGTCTGGAGTAACGATGGCAATGACTTTATC
CTGATGAGCACCTCTGAAGAAAATAAAGTCAGCCAGGTGAAAATTCGCTTTGTTAACGTCTTCAAGGATAAAACG
CTGGCCAACAAGCTGTCATTTAATTTCTCGGATAAACAAGACGTGCCTGTTAGTGAAATTATCCTGAGCTTTACC
CCGTCTTACTATGAAGACGGCCTGATTGGTTACGATCTGGGTCTGGTTTCCCTGTACAACGAAAAGTTCTACATC
AACAACTTCGGTATGATGGTGTCTGCCTGATCTACATCAACGATAGTCTGTACTACTTCAAACCGCCGGTGAAC
AATCTGATTACCGGTTTCGTCACGGTGGGCGATGACAAGTACTACTTCAACCCGATCAACGGCGGTGCGGCCAGC
ATCGGCGAAACCATCATCGATGACAAGAACTACTACTTCAACCAGTCTGGTGTCCTGCAAACCGGCGTGTTCAGT
ACGGAAGACGGTTTTAAATATTTCGCGCCGGCCAACACCCTGGATGAAAATCTGGAAGGCGAAGCGATTGACTTT
ACGGGCAAGCTGATCATCGATGAAAACATCTACTACTTCGATGACAACTACCGTGGCGCAGTGGAATGGAAAGAA
CTGGATGGTGAAATGCATTATTTTTAGCCCGGAAACCGGCAAGGCTTTCAAAGGCCTGAATCAGATTGGTGACTAC
AAATACTATTTCAACAGTGATGGCGTCATGCAAAAGGGTTTCGTGTCCATCAACGATAACAAGCATTATTTCGAT
GACAGCGGCGTTATGAAGGTCGGTTACACCGAAATTGATGGCAAACACTTTTATTTCGCGGAAAATGGCGAAATG
CAGATCGGTGTTTTTAACACCCGAAGATGGTTTTAAATACTTCGCCCATCACAACGAAGATCTGGGTAATGAAGAA
GGCGAAGAAATCAGTTATTCCGGCATTCTGAACTTCAACAACAAGATTTATTACTTCGATGACTCATTCACCGCC
GTTGTCGGCTGGAAGGATCTGGAAGACGGTTCGAAATACTATTTCGATGAAGACACGGCAGAAGCTTATATCGGC
CTGAGTCTGATCAACGATGGCCAGTACTACTTCAACGATGACGGCATCATGCAAGTGGGTTTCGTTACCATCAAC
GACAAGGTGTTTTATTTCTCAGATTCGGGCATTATCGAATCTGGTGTTTCAGAACATCGATGACAACTACTTCTAC
ATCGATGACAATGGCATCGTCCAAATTGGTGTGTTTGATACCAGCGACGGCTACAAGTACTTCGCGCCGGCCAAC
ACGGTGAACGATAATATTTACGGTCAGGCCGTTGAATATTCTGGCCTGGTCGTGTCGGTGAAGATGTGTACTAT
TTTGGCGAAACGTACACCATCGAAACCGGTTGGATCTACGACATGGAAAACGAAAGCGATAAATATTACTTCAAC
CCGGAAACGAAAAAGGCATGCAAGGGTATCAATCTGATTGATGACATCAAGTACTATTTCGATGAAAAAGGCATC
ATGCGCACCGGTCTGATCTCTTTCGAAAACAACAACTACTACTTCAACGAAAACGGTGAAATGCAGTTTGGTTAC
ATCAACATCGAAGACAAGATGTTCTATTTCGGCGAAGATGGTGTTATGCAGATTGGCGTCTTTAACACCCCGGAC
GGTTTTAAATACTTCGCGCATCAAAACACGCTGGATGAAAACTTCGAAGGCGAAAGTATCAACTACACCGGTTGG
CTGGATCTGGACGAAAAACGCTACTATTTTACCGACGAATACATTGCAGCTACGGGCAGCGTGATTATCGATGGT
GAAGAATATTATTTTGACCCGGACACCGCACAACTGGTTATTCTGAACATCATCATCATCACTAA
```

FIG 3B

TcdB - L1106K Nucleotide Sequence (part 1 of 2 for SEQ ID NO:4)

```
ATGAGCCTGGTCAACCGTAAACAACTGGAAAAAATGGCAAATGTCCGCTTTCGCACCCAAGAAGATGAATATGTC
GCAATCCTGGACGCGCTGGAAGAATACCATAACATGAGCGAAAATACCGTGGTTGAAAAGTACCTGAAGCTGAAG
GATATCAACTCCCTGACCGTATATTTACATCGACACGTATAAAAAGTCAGGCCGTAACAAGGCACTGAAAAAGTTC
AAGGAATATCTGGTGACCGAAGTTCTGGAACTGAAGAACAATAACCTGACGCCGGTTGAAAAGAACCTGCACTTC
GTCTGGATTGGCGGTCAGATCAACGATACCGCTATCAACTACATCAACCAATGGAAGGATGTGAACTCCGACTAC
AACGTGAACGTGTTTTATGATTCAAACGCATTCCTGATCAACCACCCTGAAAAAGACGGTCGTGGAATCTGCTATC
AATGATACCCTGGAAAGTTTTCGTGAAAATCTGAACGATCCGCGCTTCGACTACAACAAGTTTTTCCGTAAGCGC
ATGGAAATCATCTACGATAAGCAGAAGAACTTCATCAACTACTACAAGGCGCAACGTGAAGAAAATCCGGAACTG
ATTATCGATGACATCGTGAAGACCTACCTGAGCAACGAATACTCTAAGGAAATCGATGAACTGAACACCTACATT
GAAGAATCCCTGAACAAAATCACGCAGAACTCAGGCAACGATGTTCGCAACTTCGAAGAATTCAAGAACGGTGAA
AGCTTTAACCTGTATGAACAAGAACTGGTGGAACGTTGGAACCTGGCGGCCGCATCAGATATTCTGCGCATCTCG
GCCCTGAAAGAAATTGGCGGTATGTATCTGGATGTTGACATGCTGCCGGGCATTCAGCCGGACCTGTTTGAATCT
ATCGAAAAACCGAGCTCTGTCACCGTGGATTTCTGGGAAATGACGAAACTGGAAGCGATTATGAAATACAAGGAA
TATATCCCGGAATATACCAGTGAACATTTTGATATGCTGGACGAAGAAGTGCAGAGTTCCTTCGAATCCGTTCTG
GCCAGCAAGTCCGACAAATCAGAAATTTTTAGCAGCCTGGGTGATATGGAAGCGTCGCCGCTGGAAGTGAAGATT
GCCTTCAACAGCAAAGGTATTATCAATCAGGGCCTGATCTCTGTCAAAGATAGCTACTGCTCTAATCTGATTGTG
AAGCAAATCGAAACCGTTACAAGATCCTGAACAACAGCCTGAATCCGGCAATTTCTGAAGATAACGACTTTAAT
ACCACGACCAACACCTTCATTGACAGCATCATGGCGGAAGCCAACGCAGATAATGGCCGTTTTATGATGGAACTG
GGCAAGTATCTGCGCGTGGGCTTTTTCCCGGATGTTAAAACGACCATTAATCTGTCTGGTCCGGAAGCATACGCT
GCAGCATATCAGGATCTGCTGATGTTTAAAGAAGGTTCAATGAACATTCACCTGATCGAAGCAGATCTGCGCAAC
TTCGAAATCTCGAAAACCAATATTTCACAGTCGACGGAACAAGAAATGGCTAGTCTGTGGTCCTTTGATGACGCT
CGTGCGAAGGCCCAGTTCGAAGAATACAAGCGCAACTACTTCGAAGGCAGTCTGGGTGAAGATGACAACCTGGAC
TTCTCCCAAAATATTGTTGTCGATAAGGAATATCTGCTGGAAAAAATCAGCTCTCTGGCGCGTAGTTCCGAACGC
GGCTACATTCATTATCGTTCAGCTGCAAGGTGATAAAATTAGCTACGAAGCAGCTTGCAACCTGTTTGCAAAG
ACCCCGTATGACTCAGTGCTGTTCCAGAAAAATATCGAAGATTCGGAAATCGCTTACTACTATAACCCGGGCGAC
GGTGAAATCCAAGAAATCGATAAGTACAAGATCCCGTCAATCATCTCGGATCGTCCGAAAATCAAGCTGACCTTT
ATTGGCCACGGTAAAGATGAATTCAATACGGACATTTTTGCGGGCTTCGATGTGGACAGCCTGTCTACCGAAATT
GAAGCGGCCATCGATCTGGCCAAGGAAGACATTAGCCCGAAATCTATTGAAATCAATCTGCTGGGCTGTAACATG
TTTAGTTACTCCATCAACGTGGAAGAAACCTATCCGGGTAAACTGCTGCTGAAAGTTAAGGACAAATTTCAGAA
CTGATGCCGTCAATCTCGCAGGATAGTATTATCGTCTCCGCCAACCAATATGAAGTGCGCATTAATTCTGAAGGC
CGTCGCGAACTGCTGGATCATTCGGGTGAATGGATCAACAAAGAAGAAAGCATCATCAAGGATATCTCATCGAAG
GAATACATCAGCTTCAACCCGAAGGAAAACAAGATCACCGTGAAGTCCAAGAACCTGCCGGAACCTGTCAACGCTG
CTGCAGGAAATCCGTAATAACAGTAACAGCTCTGATATTGAACTGGAAGAAAAAGTGATGCTGACCGAATGCGAA
ATTAACGTTATCTCCAATATTGATACGCAGATCGTCGAAGAACGCATTGAAGAAGCGAAAAACCCTGACCAGCGAC
TCTATTAACTACATCAAGGATGAATTCAAGCTGATCGAAAGTATTTCCGATGCCCTGTGTGACCTGAAACAGCAA
AACGAACTGGAAGATTCACACTTTATCTCGTTCGAAGATATTTCGGAAACCGACGAAGGCTTTAGCATCCGCTTC
ATCAACAAGGAAACGGGTGAATCAATCTTCGTGGAAAAACCATCTTCTCGGAATATGCGAACCATATT
ACCGAAGAAATCAGCAAGATTAAAGGCACCATTTTTGACACGGTTAATGGTAAACTGGTCAAAAAGGTGAACCTG
GATACGACCCACGAAGTCAACACCCTGAATGCAGCGTTTTTCATTCAGAGCCTGATCGAATACAATAGTTCCAAG
GAATCACTGTCGAACCTGTCGGTTGCAATGAAAGTTCAGGTCTATGCTCAACTGTTTAGCACCGGCCTGAATACG
ATTACCGATGCGGCCAAAGTGGTTGAACTGGTGTCTACCGCGCTGGATGAAACGATCGACCTGCTGCCGACCCTG
AGTGAAGGTCTGCCGATTATCGCCACGATTATCGATGGCGTTTCCCTGGGTGCAGCTATTAAAGAACTGAGTGAA
ACCTCCGATCGCTGCTGCGTCAGGAAATCGAAGCAAAAATTGGCATCATGGCTGTTAACCTGACGACCGCAACG
ACCGCTATTATCACGTCATCGCTGGGCATCGCATCAGGTTTTTCGATTCTGCTGGTGCCGCTGGCAGGATTAGT
GCAGGTATCCCGTCCAAGGTTAATAACGAACTGGTCCTGCGCGACAAGGCTACCAAAGTCGTGGATTATTTAAA
CATGTTAGCCTGGTCGAAACCGAGGGTGTGTTCACGCTGCTGGATGACAAAATTATGATGCCGCAGGATGACCTG
GTCATCTCGGAAATCGATTTCAACAACAACAGCATTGTGCTGGGCAAATGTGAAATCGGCGTATGGAAGGCGGT
AGCGGTCATACGGTTACCGATGACATCGATCACTTTTTCAGCGCCGCCGTCTATTACCTACCGCGAACCGCACCTG
AGCATCTATGATGTGCTGGAAGTTCAGAAGGAAGAACTGGATCTGTCTAAAGACCTGATGGTCCTGCCGAACGCG
CCGAATCGTGTGTTTGCCTGGGAAACGGGTTGGACCCCGGGTCTGCGTAGCCTGGAAAATGATGGCACCAAACTG
CTGGATCGTATTCGCGACAACTACGAGGGTGAATTCTACTGGCGTTATTTTGCCTTCATCGCAGATGCTCTGATT
ACGACCCTGAAACCGCGTTATGAAGACACCAACATTCGCATCAATCTGGATAGCAACACGCGTTCTTTTATTGTG
CCGATTATCACGACGGAATATATCCGCGAAAAACTGAGCTACTCTTTCTATGGCAGCGGCGGTACCTACGCACTG
AGTCTGTCCCAGTATAATATGGGTATTAACATCGAACTGTCAGAATCGGATGTGTGGATTATCGATGTTGACAAT
GTTGTCCGCGATGTTACCATCGAAAGCGACAAAATTAAAAAGGGTGATCTGATCGAAGGCATTCTGAGTACGCTG
TCCATCGAAGAAAACAAGATCATCCTGAACAGTCATGAAATCAATTTTAGCGGCGAAGTTAACGGCTCAAATGGT
TTTGTCAGTCTGACCTTCTCCATTCTGGAAGGTATCAACGCCATTATCGAAGTGGATCTGCTGAGCAAGTCTTAT
```

FIG 4A

TcdB - L1106K Nucleotide Sequence (part 2 of 2 for SEQ ID NO:4)

```
AAACTGCTGATCAGCGGCGAACTGAAGATTCTGATGCTGAATTCTAACCACATCCAGCAAAAGATCGATTACATC
GGTTTCAACAGCGAACTGCAGAAGAATATCCCGTACTCATTCGTTGATTCGGAAGGCAAGGAAAATGGTTTCATC
AACGGCTCTACCAAAGAAGGCCTGTTTGTTAGTGAACTGCCGGATGTGGTTCTGATTAGTAAGGTCTATATGGAT
GACTCAAAACCGTCGTTTGGCTACTATTCCAACAATCTGAAGGACGTGAAGGTTATCACCAAGGATAACGTGAAC
ATCCTGACGGGTTACTATCTGAAGGATGACATTAAAATCAGTCTGTCCCTGACCCTGCAGGACGAAAAGACGATT
AAACTGAATTCGGTGCATCTGGATGAAAGCGGCGTTGCAGAAATCCTGAAGTTTATGAACCGTAAAGGTAATACG
AACACCTCAGATTCGCTGATGAGCTTCCTGGAATCTATGAACATCAAGTCCATCTTCGTTAACTTCCTGCAGTCA
AATATCAAGTTTATTCTGGATGCGAACTTCATTATCAGTGGTACGACCTCCATCGGCCAGTTTGAATTCATTTGC
GATGAAAATGACAACATCCAACCGTACTTTATTAAATTCAACACGCTGGAAACCAATTACACGCTGTATGTTGGT
AACCGCCAGAATATGATTGTCGAACCGAATTATGACCTGGATGACTCTGGCGATATCAGCTCTACCGTCATTAAC
TTTAGTCAAAAGTACCTGTATGGTATTGATTCGTGTGTGAACAAAGTCGTGATTAGCCCGAATATCTATACCGAT
GAAATTAACATCACGCCGGTGTACGAAACCAACAATACGTATCCGGAAGTCATTGTGCTGGACGCGAACTACATC
AACGAAAAGATCAACGTTAACATCAACGATCTGTCTATCCGTTATGTCTGGAGTAACGATGGCAATGACTTTATC
CTGATGAGCACCTCTGAAGAAAATAAAGTCAGCCAGGTGAAAATTCGCTTTGTTAACGTCTTCAAGGATAAAACG
CTGGCCAACAAGCTGTCATTTAATTTCTCGGATAAACAAGACGTGCCTGTTAGTGAAATTATCCTGAGCTTTACC
CCGTCTTACTATGAAGACGGCCTGATTGGTTACGATCTGGGTCTGGTTTCCCTGTACAACGAAAAGTTCTACATC
AACAACTTCGGTATGATGGTGTCTGGCCTGATCTACATCAACGATAGTCTGTACTACTTCAAACCGCCGGTGAAC
AATCTGATTACCGGTTTCGTCACGGTGGGCGATGACAAGTACTACTTCAACCCGATCAACGGCGGTGCGGCCAGC
ATCGGCGAAACCATCATCGATGACAAGCAACTACTACTTCAACCAGTCTGGTGTCCTGCAAACCGGCGTGTTCAGT
ACGAAGACGGTTTTAAATATTTCGCGCCGGCCAACACCCTGGATGAAAATCTGGAAGGCGAAGCGATTGACTTT
ACGGGCAAGCTGATCATCGATGAAAACATCTACTACTTCGATGACAACTACCGTGGCGCAGTGGAATGGAAAGAA
CTGGATGGTGAAATGCATTATTTTAGCCCGGAAACCGGCAAGGCTTTCAAAGGCCTGAATCAGATTGGTGACTAC
AAATACTATTTCAACAGTGATGGCGTCATGCAAAAGGGTTTCGTGTCCATCAACGATAACAAGCATTATTTCGAT
GACAGCGGCGTTATGAAGGTCGGTTACACCGAAATTGATGGCAAACACTTTTATTTCGCGGAAAATGGCGAAATG
CAGATCGGTGTTTTTAACACCGAAGATGGTTTTAAATACTTCGCCCATCACAACGAAGATCTGGGTAATGAAGAA
GGCGAAGAAATCAGTTATTCCGGCATTCTGAACTTCAACAACAAGATTTATTACTTCGATGACTCATTCACCGCC
GTTGTCGGCTGGAAGGATCTGGAAGACGGTTCGAAATACTATTTCGATGAAGACACGGCAGAAGCTTATATCGGC
CTGAGTCTGATCAACGATGGCCAGTACTACTTCAACGATGACGGCATCATGCAAGTGGGTTTCGTTACCATCAAC
GACAAGGTGTTTTATTTCTCAGATTCGGGCATTATCGAATCTGGTGTTCAGAACATCGATGACAACTACTTCTAC
ATCGATGACAATGGCATCGTCCAAATTGGTGTGTTTGATACCAGCGACGGCTACAAGTACTTCGCGCCGGCCAAC
ACGGTGAACGATAATATTTACGGTCAGGCCGTTGAATATTCTGGCCTGGTTCGTGTCGGTGAAGATGTGTACTAT
TTTGGCGAAACGTACACCATCGAAACCGGTTGGATCTACGACATGGAAAACGAAAGCGATAAATATTACTTCAAC
CCGGAAACGAAAAAGGCATGCAAGGGTATCAATCTGATTGATGACATCAAGTACTATTTCGATGAAAAGGCATC
ATGCGCACCGGTCTGATCTCTTTCGAAAACAACAACTACTACTTCAACGAAAACGGTGAAATGCAGTTTGGTTAC
ATCAACATCGAAGACAAGATGTTCTATTTCGGCGAAGATGGTGTTATGCAGATTGGCGTCTTTAACACCCCGGAC
GGTTTTAAATACTTCGCGCATCAAAACACGCTGGATGAAACTTCGAAGGCGAAGTATCAACTACACCGGTTGG
CTGGATCTGGACGAAAAACGCTACTATTTTACCGACGAATACATTGCAGCTACGGGCAGCGTGATTATCGATGGT
GAAGAATATTATTTTGACCCGGACACCGCACAACTGGTTATTTCTGAACATCATCATCATCATCACTAA
```

FIG 4B

Rb$^{86}$ release on vero cells pH 4.8

- TcdA
- TcdA$_{DXD}$
- TcdA$_{KK}$
- TcdA$_{SAS}$
- TcdA$_{L1108K}$
- TcdA$_{KS}$

FIGURE 13

Dose response curve

- TcdA
- TcdA$_{DXD}$
- TcdA$_{1831}$
- TcdA$_{KK}$
- TcdA$_{VNN}$
- TcdA$_{L1108K}$
- TcdA$_{KS}$

FIGURE 14

COMPOSITIONS AND METHODS FOR TREATING OR PREVENTING *CLOSTRIDIUM* INFECTION

CROSS REFERENCE TO RELATED APPLICATIONS

This application is a national stage entry under 35 U.S.C. § 371 of PCT/CA2015/050115, filed on Feb. 17, 2015, which claims the benefit of priority of U.S. Provisional Patent Application No. 61/941,090 entitled TRANSLOCATION-DEFECTIVE RECOMBINANT HOLOTOXINS OF *CLOSTRIDIUM DIFFICILE* AS IMMUNOGENS filed on Feb. 18, 2014 and U.S. Provisional Patent Application No. 62/076,689 entitled *CLOSTRIDIUM* TOXIN PORE FORMING DOMAIN AND ASSOCIATED VACCINES AND NEUTRALIZING ANTIBODIES filed on Nov. 7, 2014, all of which are hereby incorporated by reference.

REFERENCE TO A SEQUENCE LISTING

This application contains references to amino acid sequences and/or nucleic acid sequences which have been submitted concurrently herewith as the sequence listing text file "61811478_1.txt", file size 62 KiloBytes (KB), created on 12 Aug. 2016. The aforementioned sequence listing is hereby incorporated by reference in its entirety pursuant to 37 C.F.R. § 1.52(e)(5).

FIELD

The present disclosure relates generally to compositions for reducing incidence or severity of *Clostridium difficile* (*C. difficile*) infection. More particularly, the present disclosure relates to atoxic mutated forms of *C. difficile* toxin proteins.

BACKGROUND

*C. difficile* is a leading cause of antibiotic-associated infection in hospitals worldwide, including such infections as hospital-acquired diarrhea and pseudomembranous colitis. Disease symptoms are caused by homologous toxins A and B (TcdA and TcdB), which form membrane-spanning translocation pores through which associated cytotoxic enzymatic domains are delivered into target cells of the colonic epithelium. This leads to cellular death and tissue damage. Binding to target cells triggers toxin internalization into acidified vesicles, whereupon cryptic segments from within the translocation domain unfurl and insert into the membrane of the epithelial cell, creating a transmembrane passageway to the cytosol. Despite a wealth of information for the enzymatic domains that act once inside the cell, little is known about the translocation pore and its role disease pathogenesis.

TcdA and TcdB are the primary virulence determinants of pathogenic *C. difficile*. TcdA and TcdB are responsible for the symptoms associated with infection, including diarrhea and pseudomembranous colitis. TcdA and TcdB are large (approximately 308 kDa and 270 kDa, respectively), homologous toxins sharing 48% sequence identity. An amino acid sequence representing TcdB is provided in FIG. 1 (SEQ ID NO:1). TcdA and TcdB appear to intoxicate target cells using a strategy that is similar to a number of smaller A-B toxins, such as anthrax toxin and diphtheria toxin (DT). In addition to a cytotoxic enzymic A-domain and receptor binding B-domain responsible for binding and translocating the A-domain into cells, TcdA and TcdB are equipped with an internal autoprocessing domain that proteolytically cleaves and releases the N-terminal glucosyltransferase domain in response to intracellular inositol hexakisphosphate.

The series of events leading to the delivery of the A-domain into cells begins with toxin binding to an as yet identified receptor on target cells via the C-terminal receptor-binding domain (the B-domain), which triggers toxin internalization into acidified vesicles via clathrin-mediated endocytosis. In the endosome, cryptic regions from within the large ~1000 amino acid translocation domain emerge and insert into the endosomal membrane, creating a pore that is believed to enable translocation of the N-terminal glucosyltransferase (the A-domain) into the cytosol. Processed and released A-chains enzymatically glucosylate and thereby inactivate intracellular Rho and Ras family GTPases, leading first to cytopathic effects (such as cell rounding), and later cytotoxic effects, such as apoptosis and necrosis.

Like many other A-B toxins that mediate their own delivery into cells, high-resolution structures of the enzymic A-domains and the receptor-binding portion of the B-domains of glucosylating toxin family members are known, while the structure and mechanism of the pore-forming translocation domain remains poorly characterized. These inter-connected processes have been proposed to be mediated by the central ~1000 amino acid D-domain (at about aa 801-1850). However, absent structural information for this domain in either the pre-pore or pore state, no framework exists for resolving the functional determinants for this large domain that govern pore formation and translocation. It is established that in response to acidic pH, the D-domain undergoes a conformational change that results in the formation of ion-conductive pores in both biological membranes and artificial lipid bilayers.

It has been hypothesized that the cluster of 172 hydrophobic, highly conserved amino acids in the middle of the translocation domain (i.e., residues 958-1130 in TcdA; and, 956 to 1128 in TcdB) comprised some, if not all, of the segments that form the translocation pore. See von Eichel-Streiber et al. (1992), Mol Gen Genet 233(1-2):260-268. Demonstrating this, however, has been challenging, in large part due to difficulties associated with manipulating Clostridial toxin genes at the genetic level. The recent availability of clones of both TcdA and TcdB in *Bacillus megaterium* expression plasmids, which enable the high-level production of stably folded toxin, has facilitated research in this direction, however studies specifically addressing the structure and function of the translocation domain have been limited to large-fragment deletions to probe function (Genisyuerek et al. (2011) Mol Microbiol 79(6)1643-1654; Zhang et al. (2013) PLoS One 8(3): e58634).

U.S. patent application Ser. No. 13/486,550, filed Jun. 1, 2012 and given US Patent Publication No. US 2012/0276132 A1, describes a recombinant toxin of *C. difficile* which is based on a 97 amino acid deletion in the transmembrane domain.

There is a need for a vaccine to *C. difficile* that can target toxic proteins, and that could elicit adequate systemic or mucosal immunity to prevent infection or reduce the severity of infection. It is desirable to provide a protein that is highly similar to the native toxin of *C. difficile*, in which toxicity is reduced or eliminated.

SUMMARY

It is an object of the present disclosure to obviate or mitigate at least one disadvantage of previous efforts to reduce incidence or severity of *Clostridium* infection, such as *C. difficile* infection.

There is provided herein a recombinant *Clostridium* toxin protein comprising a mutant of SEQ ID NO: 11 (AGISA-GIPSLVNNEL).

Further, there is provided herein a recombinant protein which is a *Clostridium* TcdA toxin protein comprising a L1108K mutation; a recombinant protein which is a *Clostridium* TcdB toxin protein comprising a L1106K mutation; a recombinant protein which is a *Clostridium* TcdA toxin protein comprising mutations V1109S, N1110A, and N1111S; and a recombinant protein which is a *Clostridium* TcdB toxin protein comprising mutations V1107S, N1108A, and N1109S.

There is also provided herein an immunogenic composition comprising one or more of the above recombinant proteins and a pharmaceutically acceptable excipient. The composition may be a vaccine, and may comprise an adjuvant.

A nucleic acid is provided herein encoding one or more of the above-noted recombinant *Clostridium* toxin proteins. A vector comprising such a nucleic acid, and a cell comprising such a vector are provided herein.

There is provided herein a kit comprising the composition described herein, together with instructions for use in treating or preventing *Clostridium* infection.

Further, a method is provided herein for eliciting an immune response to *Clostridium* in a subject comprising administration of the recombinant *Clostridium* toxin protein described herein to the subject.

There is provided herein an antibody or antigen-binding fragment thereof which specifically binds to a modified *Clostridium difficile* toxin A (TcdA) comprising a L1108K mutation, a modified *Clostridium difficile* toxin B (TcdB) protein comprising a L1108K mutation; a modified *Clostridium difficile* toxin A (TcdA) comprising V1109S, N1110A, and N1111S mutations; or a modified *Clostridium difficile* toxin B (TcdB) protein comprising V1107S, N1108A, and N1109S mutations. Such an antibody or antigen-binding fragment thereof may be used to prevent infection from *Clostridium* in a subject, or used to prepare a medicament for such a purpose.

There is also provided herein a method of identifying an antibody or antigen-binding fragment thereof which specifically binds to a portion of an epitope defined by SEQ ID NO: 11 (AGISAGIPSLVNNEL), SEQ ID NO:12 (VPLAGISA-GIPSLVNNELVL), or SEQ ID NO: 13 (LPIAGISAG-IPSLVNNELIL) in a *Clostridium* TcdA and/or TcdB toxin, comprising the steps of: a) immunizing an animal with a *Clostridium* TcdA or TcdB toxin comprising SEQ ID NO: 11, SEQ ID NO: 12, or SEQ ID NO: 13; b) obtaining sera from the immunized animal subsequent to immunization; and c) screening the sera for an antibody or antigen-binding fragment thereof which specifically binds to a portion of an epitope defined by SEQ ID NO: 11, SEQ ID NO: 12, or SEQ ID NO: 13 in the *Clostridium* TcdA and/or TcdB toxin.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 1 shows an amino acid sequence of wild-type (WT) TcdB (SEQ ID NO:1).

FIG. 2 shows an amino acid sequence of a mutant of wild-type TcdB showing codon AAG encoding lysine (K) at residue 1106 (thus, representing "L1106K") (SEQ ID NO:2).

FIG. 3A is a first portion of SEQ ID NO:3, of a nucleic acid sequence encoding wild-type TcdB, showing codon CTG, encoding leucine (L) at position 1106.

FIG. 3B is a second portion of SEQ ID NO:3, a nucleic acid sequence encoding wild-type TcdB when taken together with the portion shown in FIG. 3A.

FIG. 4A is a first portion of SEQ ID NO:4, of a nucleic acid sequence encoding a mutant of wild-type TcdB showing codon AAG encoding lysine (K) at residue 1106 (thus, representing "L1106K").

FIG. 4B is a second portion of SEQ ID NO:4, a nucleic acid sequence encoding mutant TcdB when taken together with the portion shown in FIG. 4A.

FIG. 13 shows Rb86 release for Vero cells at pH 4.8, with TcdA and mutants thereof.

FIG. 14 shows a dose response curve for CHO cell viability for TcdA and mutants.

DETAILED DESCRIPTION

Figure 5:
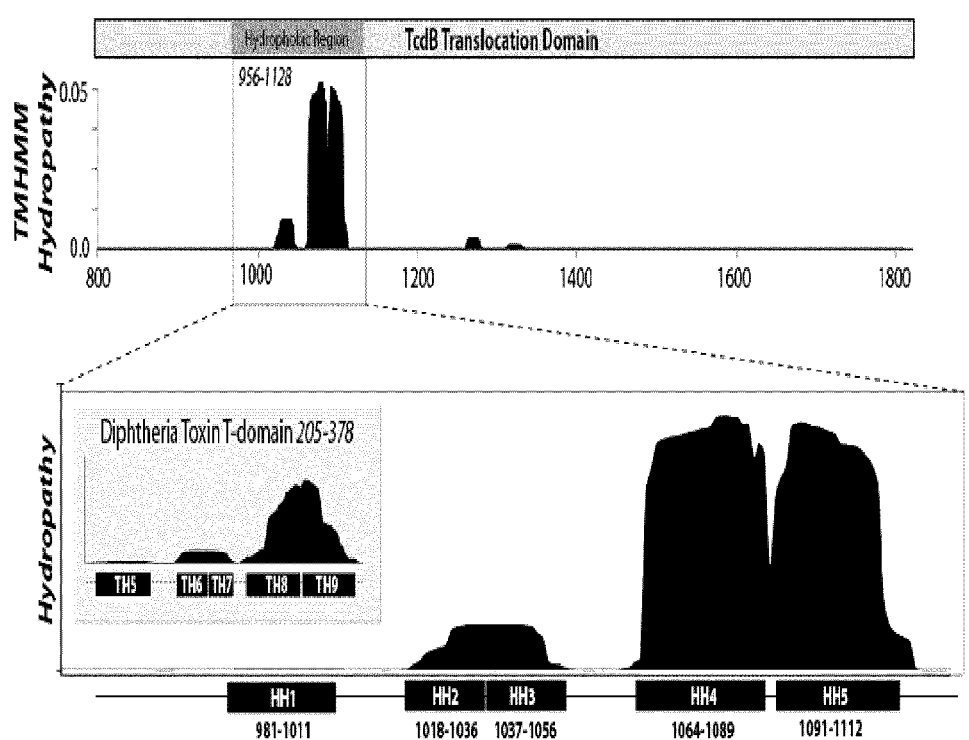
FIG. 5 shows a hydropathy analysis of the translocation domain. In the top panel, hydropathy analysis of the entire translocation domain of TcdB is shown from a membrane protein topology prediction method. The bottom panel shows hydropathy analysis of the 172 residue hydrophobic region, indicating predicted hydrophobic helices (HH1-HH5). The inset shows hydropathy analysis of the 173 amino acid diphtheria toxin translocation domain.

Generally, the present disclosure provides recombinant *Clostridium* toxin proteins which comprise one or more mutations, and are thus said to be "mutant" sequences containing SEQ ID NO: 11 (AGISAGIPSLVNNEL), which is a portion of a highly conserved region of native TcdA and TcdB. The one or more mutations in this region render the protein a mutant of SEQ ID NO: 11. The protein need only contain this sequence, and is thus said to comprise the sequence within the length of the protein, but need not be limited to this sequence only. The mutant of SEQ ID NO: 11 may, for example, have from 1 to 4 mutations with reference to altered amino acid residues. Exemplary mutations may occur in LVNN of SEQ ID NO: 11, which are located at the positions 10 to 13 of SEQ ID NO: 11. When the N at position 12 is referred to, the term "the first N" may be used, whereas when the N at position 13 is referred to, it may be referred to as "the second N", as a skilled person would understand that within the portion of the protein defined by SEQ ID NO: 11, only these two N residues are present. The mutation may be L to K at the 10$^{th}$ amino acid position of SEQ ID NO: 11. Further, the mutation may be of VNN to SAS at positions 11 to 13 of SEQ ID NO: 11.

For example, mutant may contain the mutations within of SEQ ID NO: 12 (VPLAGISAGIPSLVNNELVL) from TcdB or SEQ ID NO: 13 (LPIAGISAGIPSLVNNELIL) from TcdB, both of which contain SEQ ID NO: 11.

The mutant may be mutated at particular residues, and thus may comprise SEQ ID NO: 14 (VPLAGISAGIPSK-VNNELVL) for TcdB; SEQ ID NO: 15 (LPIAGISAGIPSK-VNNELIL) for TcdA; SEQ ID NO: 16 (VPLAGISAGIPSK-SASELVL) for TcdB; or SEQ ID NO: 17 (LPIAGISAGIPSKSASELIL) for TcdA. However, the mutants are not limited to these.

A recombinant protein mutant is described which is comparable to native *Clostridium* TcdA toxin protein, except that it comprises a L1108K mutation, or which is comparable to *Clostridium* TcdB toxin protein, except that it comprises a L1106K mutation. Further, a recombinant protein is described which is a *Clostridium* TcdA toxin protein comprising mutations V1109S, N1110A, and N1111S; or a *Clostridium* TcdB toxin protein comprising mutations V1107S, N1108A, and N1109S. These proteins retain conformational properties of the native TcdA and TcdB toxins, but do not possess toxic effects.

The proteins described herein may have an epithelial cell toxicity that is reduced by 100-fold or greater, or 1000-fold or greater compared to wild-type *Clostridium* toxin.

The proteins described herein may comprise a sequence of 75% or greater, 80% or greater, 85% or greater, 90% or greater, 95% or greater, or 99% or greater identity to residues 958 to 1130 of TcdA; or to residues 956 to 1128 of TcdB, which are hydrophobic and highly conserved residues within the middle of the translocation domain of these *Clostridium* toxins.

The proteins described may be encoded by a sequence of 75% or greater, 80% or greater, 85% or greater, 90% or greater, 95% or greater, or 99% or greater identity to SEQ ID NO:4.

The proteins described herein may be produced recombinantly in a *Bacillus* host. For example, the *Bacillus* host may be *Bacillus megaterium*.

Immunogenic compositions are described herein which comprise one or more of the recited recombinant proteins having the described mutations, together with one or more pharmaceutically acceptable excipients. Such a composition may, for example, be a vaccine, which may be combined with or administered together, in serial, or in parallel with a pharmaceutically acceptable adjuvant. The vaccine may have a toxicity, attributable to the recombinant *Clostridium* toxin protein, which is reduced by 100-fold or greater, or 1000-fold or greater compared to the wild-type *Clostridium* toxin(s).

Nucleic acids are described which encode the subject recombinant *Clostridium* toxin proteins. Such a nucleic acid may encode a modified *Clostridium difficile* toxin A (TcdA) protein comprising a L1108K mutation, or may encode a modified *Clostridium difficile* toxin B (TcdB) protein comprising a L1106K mutation. Further, such nucleic acids may encode a modified TcdA with VNN mutated to SAS at residues 1109-1111 (TcdA) or at 1107-1109 (TcdB). A vector is described herein which comprises such nucleic acids as these, or others which may encode the subject proteins. There is also provided herein a cell which comprises such a vector.

A kit comprising the composition of which contains the protein is described, which kit includes instructions for use of the composition in treating or preventing *Clostridium* infection.

A method of eliciting an immune response to *Clostridium* is described. The method is intended for use by such subjects in need of prevention or treatment for *Clostridium* infection. The method involves administration to the subject of the recombinant *Clostridium* toxin protein described herein. The method may be used to treat, prevent, or otherwise counter *Clostridium* infections such as *Clostridium difficile*, *Clostridium sordellii*, *Clostridium novyi*, or *Clostridium perfringens*. The administration of the protein to the subject may elicit an effective immune response before the subject has had any exposure to *Clostridium* toxin, and in this way, the method may be said to be prophylactic. The method may involve any variety of routes for administration of the protein to the subject, such as intravenous, intramuscular, subcutaneous, intraperitoneal, intradermal, ransdermal, mucosal, sublingual. Intranasal or oral administration.

The method for eliciting an immune response may include an assessment of antibody titer in the subject, so as to check for antibodies specifically binding to wild-type *Clostridium* toxin B or toxin A. This may be used for comparison with a control value to determine the immune response of the subject. The control value used may be selected as a level of antibody titer for TcdB, measured in the subject prior to administering the protein. In this way, the subject can serve as her own control. Optionally, when the protein is administered to the subject, it may be in combination with a pharmaceutically acceptable adjuvant in an appropriate manner to heighten or otherwise encourage immune response.

There is described herein an antibody or antigen-binding fragment thereof which specifically binds to a modified *Clostridium difficile* toxin A (TcdA) comprising a L1108K mutation, a modified *Clostridium difficile* toxin B (TcdB)

protein comprising a L1106K mutation; a modified *Clostridium difficile* toxin A (TcdA) comprising V1109S, N1110A, and N1111S mutations; or a modified *Clostridium difficile* toxin B (TcdB) protein comprising V1107S, N1108A, and N1109S mutations. For example, the antibody or antigen-binding fragment thereof may specifically bind to a protein having a sequence according to SEQ ID NO:2. Further, the antibody or antigen-binding fragment thereof may be one which specifically binds to a portion of an epitope comprising AGISAGIPSLVNNEL (SEQ ID NO: 11) in a *Clostridium* TcdA or TcdB toxin, or may be one which specifically binds to SEQ ID NO:12 (VPLAGISAGIPSLVNNELVL) or SEQ ID NO: 13 (LPIAGISAGIPSLVNNELIL). The antibody or antigen-binding fragment thereof may specifically bind to the TcdA and the TcdB toxin. The antibody may be a monoclonal antibody, or may be a humanized antibody.

There is described herein a method of preventing infection from *Clostridium* in a subject, comprising administering to the subject an effective amount of the antibody or antigen-binding fragment thereof.

The described proteins may be used for eliciting an immune response to *Clostridium difficile* toxin A (TcdA) or toxin B (TcdB) in a subject. Further, the use of the antibody or antigen-binding fragment thereof may be for preventing *Clostridium* infection in a subject. The described proteins may be used for preparation of a medicament for eliciting an immune response to *Clostridium difficile* toxin A (TcdA) or toxin B (TcdB) in a subject. Further, the use of the antibody or antigen-binding fragment thereof may be for preparation of a medicament for preventing *Clostridium* infection in a subject.

A method is described herein for identifying an antibody or antigen-binding fragment thereof which specifically binds to a portion of an epitope defined by SEQ ID NO: 11 (AGISAGIPSLVNNEL), SEQ ID NO:12 (VPLAGISAGIPSLVNNELVL), or SEQ ID NO: 13 (LPIAGISAGIPSLVNNELIL) in a *Clostridium* TcdA and/or TcdB toxin, comprising the steps of: a) immunizing an animal with a *Clostridium* TcdA or TcdB toxin comprising SEQ ID NO: 11, SEQ ID NO: 12, or SEQ ID NO: 13; b) obtaining sera from the immunized animal subsequent to immunization; and c) screening the sera for an antibody or antigen-binding fragment thereof which specifically binds to a portion of an epitope defined by SEQ ID NO: 11; SEQ ID NO: 12, or SEQ ID NO: 13 in the *Clostridium* TcdA and/or TcdB toxin.

In such a method, the antibody or antigen-binding fragment thereof may specifically bind to both the TcdA and TcdB toxin. Further, the screening may be conducted using a high-throughput screening method. The sera may be screened by ELISA. The method may comprise the step of adding *Clostridium* toxin to cell culture and determining if the sera decreases the cytotoxic effect of the *Clostridium* toxin on the cells.

A protein, a nucleic acid, and an antibody are described herein, as well as an immunogenic composition or vaccine composition, based on a *C. difficile* toxin protein TcdA and/or TcdB, which contain one or more mutations so as to be rendered less toxic or atoxic. For Example, TcdB comprising the mutation L1106K is rendered less toxic than native TcdB. Similarly, the mutation of TcdA with L1108K renders a protein less toxic than native TcdA. TcdA mutated from VNN to SAS at residues 1107-1109 (TcdB) or residues 1109-1111 (TcdA) are less toxic than wild-type. The use of these proteins, nucleic acid encoding for them, or antibodies based upon these for immunizing a subject against *Clostridium* infection are described herein. Despite the mutation and reduced toxicity, the mutated TcdA and TcdB proteins described herein retain native protein conformation comparable to wild-type TcdB.

An amino acid sequence of a L1106K protein is provided in SEQ ID NO:2. An exemplary nucleotide sequence encoding a wild-type TcdB protein is found in SEQ ID NO: 3. An exemplary nucleic acid sequence encoding a protein sequence having the L1106K mutation is provided in SEQ ID NO:4.

There are also described herein translocation-defective recombinant holotoxin proteins of *Clostridium difficile* toxin TcdB, for use as immunogens. The proteins have a L1106K mutation. Protein sequences, nucleotide sequences, and antibodies are described as well as compositions, vaccines, uses and methods pertaining to treatment or prevention of *C. difficile* infection. The L1106K mutation blocks pore-formation within the translocation domain and thus reduces toxicity.

It would be advantageous to develop neutralizing antibodies against homologous toxins from organisms associated with rare infections, such as those involving *Clostridium sordellii* and *Clostridium novyi*. It is possible that neutralizing antibodies against *Clostridium* that are currently in development may not be effective against all strains, since the TcdB sequence can vary significantly. Efforts have been made to develop non-toxic vaccines against *Clostridium* toxin using formalin-treated TcdA and TcdB proteins, but formalin-treatment results in significant disruption of the toxin structure.

There is described herein a 3.25 Å crystal structure for residues 1-1832 of *C. difficile* TcdA. The sequence of TcdA is known, for example, GenBank describes a 2710 aa sequence for TcdA in accession number CAA63564, hereby incorporated by reference, as described by Hundsberger et al., Eur. J. Biochem. 244 (3), 735-742 (1997). The structure reveals a novel epitope to be targeted for pan-toxin neutralization. Mutation of the epitope, representing a pore forming domain as revealed by the crystal structure, can provide a toxin protein with decreased toxicity which can be used as a vaccine antigen. The pore forming domain is a hydrophobic helical element, the sequence of which strictly conserved in 6 homologous toxins: TcdA and TcdB from *C. difficile*, TcsH and TcsL from *C. sordellii*, Tcna from *C. novyi*, and TpeL from *C. perfringens*. It is shown herein that mutation of the conserved loop removes or decreases all or essentially all of the toxicity associated with the toxin in cell culture. The strictly conserved amino acid sequence is LPIAGISAGIPSLVNNELIL (SEQ ID NO: 13). In TcdA, this typically corresponds to amino acids 1096 to 1115, while in TcdB this typically corresponds to amino acids 1094 to 1113, taking into account the slightly different sequences present in different strains of *C. difficile*. A mutation tested involved changing VNN of SEQ ID NO: 13 to SAS in both TcdA and TcdB.

Identification of this novel epitope permits the preparation neutralizing antibodies against homologous toxins from organisms associated with rare infections such as *C. sordellii* and *C. novyi*, and can be used to provide a common neutralizing antibody against TcdA and TcdB that would be effective across many, and possibly all strain variants. Mutation of the novel epitope can provide safe vaccine antigens.

A modified *Clostridium difficile* toxin B (TcdB) protein is described herein comprising a L1106K mutation. The protein may comprise a sequence of 75% or greater identity to SEQ ID NO:2, or may comprise a sequence of 80% or greater, 85% or greater, 90% or greater, 95% or greater, or 99% or greater identity to SEQ ID NO:2. The protein may have the sequence according to SEQ ID NO:2, and encompasses equivalent proteins which have deletions or substitutions while generally maintaining the properties of SEQ ID NO:2. The protein may be one encoded by a nucleic acid sequence of 75% or greater identity to SEQ ID NO:4. Specifically, the protein may be encoded by a sequence of 80% or greater, 85% or greater, 90% or greater, 95% or greater, or 99% or greater identity to SEQ ID NO:4. The protein may be encoded by the nucleic acid sequence of SEQ ID NO:4, which encompasses equivalents, having different codons encoding the same amino acids or different codons encoding conservatively substituted amino acids.

The protein described herein possesses epithelial cell toxicity that is reduced by 10-fold or greater, 100-fold or greater, or 1000-fold or greater when compared to wild-type (WT) TcdB.

In exemplary embodiments, the protein may be produced recombinantly in a *Bacillus* host. For example, the *Bacillus* host may be *Bacillus megaterium*.

A nucleic acid is described herein encoding a modified *Clostridium difficile* toxin B (TcdB) protein comprising a L1106K mutation. The nucleic acid may comprise a sequence of 75% or greater identity to SEQ ID NO:4. For example, the nucleic acid may comprise a sequence of 80% or greater, 85% or greater, 90% or greater, 95% or greater, or 99% or greater identity to SEQ ID NO:4. The nucleic acid may comprise the sequence according to SEQ ID NO:4. The nucleic acid may encode a protein of 75% or greater identity to SEQ ID NO:2. For example, the nucleic acid may comprise a sequence of 80% or greater, 85% or greater, 90% or greater, 95% or greater, or 99% or greater identity to SEQ ID NO: 2, and may specifically encode SEQ ID NO:2.

The nucleic acid may be one in which the epithelial cell toxicity of the encoded protein is reduced by 10-fold or greater, 100-fold or greater, or 1000-fold or greater compared to wild-type (WT) TcdB.

A vector is described herein comprising the nucleic acid described above. A cell comprising such a vector is also encompassed. The cell may thus express a modified *Clostridium difficile* toxin B (TcdB) protein comprising the L1106K mutation, for example that of SEQ ID NO:2, or a functional equivalent thereto having 75% or greater identity to SEQ ID NO:2.

An immunogenic composition is described herein comprising the protein described above. The composition may comprise a pharmaceutically acceptable excipient. The composition may be used as a vaccine to *Clostridium difficile*. A kit is provided, comprising such a composition together with instructions for use as a vaccine to *Clostridium difficile*.

A method of eliciting an immune response to *Clostridium difficile* toxin B (TcdB) in a subject is described comprising: delivering to the subject a modified *Clostridium difficile* toxin B (TcdB) protein comprising a L1106K mutation or a nucleic acid encoding the modified *Clostridium difficile* toxin B (TcdB) protein comprising the L1106K mutation. The method may involve delivering the protein or the nucleic acid via intravenous, intramuscular, subcutaneous, intraperitoneal, intradermal, transdermal, mucosal, sublingual, intranasal or oral administration to the subject. The method may further comprise assessing antibody titer in the subject for antibodies specifically binding to wild-type TcdB for comparison with a control value to determine immune response to the modified TcdB protein or nucleic acid. Such a control value may, for example, be a level of antibody titer for TcdB in the subject prior to delivering the modified protein or nucleic acid.

An antibody is provided herein which is raised to and/or specifically binds to a modified *Clostridium difficile* toxin B (TcdB) protein comprising a L1106K mutation or an equivalent mutation. Such an antibody may specifically bind to a protein having a sequence according to SEQ ID NO:2, or one at least 75% identical thereto. Such an antibody may be monoclonal, and/or may be humanized.

The use of a modified *Clostridium difficile* toxin B (TcdB) protein is described herein comprising a L1106K mutation or a nucleic acid encoding the modified *Clostridium difficile* toxin B (TcdB) protein comprising the L1106K mutation for eliciting an immune response to *Clostridium difficile* toxin B (TcdB) in a subject.

Further, as use is provided of a modified *Clostridium difficile* toxin B (TcdB) protein comprising a L1106K mutation or a nucleic acid encoding the modified *Clostridium difficile* toxin B (TcdB) protein comprising the L1106K mutation for preparation of a medicament for eliciting an immune response to *Clostridium difficile* toxin B (TcdB) in a subject.

Regarding substitutions within the described sequences, different codons can encode lysine, and thus it is understood that the nucleic acid sequence of SEQ ID NO:4 is merely one example of a sequence that can encode the amino acid sequence L1106K of SEQ ID NO:2. Codons MG and AAA encode lysine. Further, amino acids than lysine may be substituted for leucine at this position, provided a similar effect in blocking pore-formation within the translocation domain is achieved, and toxicity is appropriately reduced. Such residues would be considered equivalent, provided the atoxic effect is maintained. Lysine is a basic amino acid, and thus it may be considered an appropriate conservative substitution to utilize other basic amino acids, such as arginine and glutamine. Conservative substitutions in other residues of SEQ ID NO:2 may be made, provided the desired properties of the protein are intact: preserving the intoxicating properties of wild-type TcdB, while rendering the protein atoxic. Deletions and substitutions which may be permitted while maintaining these properties may render a protein having 75% or greater identity to that of SE4 ID NO:2, for example 80% or greater, 85% or greater, 90% or greater, 95% or greater, or 99% or greater identity thereto.

Similarly, nucleic acid sequences utilizing equivalent codons, or codons encoding a conservative substitution of amino acids are considered equivalent to SEQ ID NO:4, provided the protein encoded maintains the properties described herein. Nucleotide sequences encoding for a protein having deletions and substitutions which may be permitted while maintaining these properties may be encoded by a sequence having 75% or greater identity to that of SEQ ID NO:4, for example 80% or greater, 85% or greater, 90% or greater, 95% or greater, or 99% or greater identity thereto.

Conservative amino acid substitutions which are known in the art are as follows with conservative substitutable candidate amino acids showing in parentheses: Ala (Gly, Ser); Arg (Gly, Gln); Asn (Gln; His); Asp (Glu); Cys (Ser); Gln (Asn, Lys); Glu (Asp); Gly (Ala, Pro); His (Asn; Gln); Ile (Leu; Val); Leu (Ile; Val); Lys (Arg; Gln); Met (Leu, Ile); Phe (Met, Leu, Tyr); Ser (Thr; Gly); Thr (Ser; Val); Trp (Tyr); Tyr (Trp; Phe); Val (Ile; Leu).

Compositions having immunogenic properties, such as a vaccine, are described herein for use in treating or vaccinating against *C. difficile*. The described compositions elicit antibody production in a subject. The production of antibodies to TcdB can protect against or reduce the severity of *C. difficile* infection. Advantageously, the described mutation results in a protein that maintains wild-type characteristics but has a greatly reduced toxicity compared with the wild-type TcdB protein. A *Bacillus megaterium* expression system was used to generate mutant proteins, which were tested for a reduction in or absence of toxicity.

The protein or nucleic acid may be formulated in a composition with a pharmaceutically acceptable excipient, for delivery as a vaccine to a subject at an effective dose, optionally with an adjuvant. Such a vaccination would be utilized for prevention of the disease and symptoms associated with *C. difficile* infection in human or animal subjects.

The subject may be a human, and may advantageously be a human at high risk for *C. difficile* infection, such as a hospitalized or immune compromised human. Further, the subject may be a non-human animal such as a livestock animal, a research animal, or a domesticated animal such as a companion animal at risk of infection. The subject may be an animal in a stressful circumstance, at risk for *C. difficile* infection.

Antibodies against *C. difficile* are typically present in the general population. Thus, antibody titer may involve assessing an individual's own base-line level (as a control value) of antibody before and after vaccination is used to elicit an immune response.

Advantageously, the mutant toxin protein provided herein involves a primary point mutation that permits the protein to maintain similar properties to the native toxin while exhibiting a greatly reduced toxicity.

The composition may comprise the mutant protein as an antigen along with one or more pharmaceutically acceptable carrier, excipient or diluent. Optionally, the composition may further include an adjuvant. The composition may be used in conjunction with conventional treatments or prevention strategies for *C. difficile* infection, either delivered separately or simultaneously. Such conventional treatments may encompass antibiotic treatment with metronidazole or vancomycin, or probiotic delivery.

In certain embodiments, the composition optionally further comprises one or more additional therapeutic agents. For example, an antibiotic compound, anti-viral compound, anti-fungal compound may be included. Other optional components of the composition include one or more growth factor, anti-inflammatory agent, vasopressor agent, collagenase inhibitor, topical steroid, matrix metalloproteinase inhibitor, ascorbate, angiotensin, caireticulin, tetracycline, fibronectin, collagen, thrombospondin, transforming growth factor (TGF), keratinocyte growth factor (KGF), fibroblast growth factor (FGF), insulin-like growth factor (IGF), epidermal growth factor (EGF), platelet derived growth factor (PDGF), neu differentiation factor (NDF), hepatocyte growth factor (HGF), or hyaluronic acid.

Pharmaceutically acceptable carriers include solvents, diluents, liquid vehicles, dispersion or suspension aids, surface active agents, isotonic agents, thickening or emulsifying agents, preservatives, solid binders, or lubricants. Carriers may be selected to prolong dwell time for sustained release appropriate to the selected route of administration. Exemplary carriers include sugars such as glucose and sucrose, starches such as corn starch and potato starch, fibers such as cellulose and its derivatives, sodium carboxymethyl cellulose, ethyl cellulose, cellulose acetate, powdered tragacanth, malt, gelatin, talc, cocoa butter, suppository waxes, oils such as peanut oil, cottonseed oil, safflower oil, sesame oil, olive oil, corn oil, and soybean oil; glycols such as propylene glycol, esters such as ethyl oleate and ethyl laurate, agar, buffering agents such as magnesium hydroxide and aluminum hydroxide, alginic acid, pyrogen-free water, isotonic saline, Ringers solution, ethyl alcohol, phosphate buffer solutions, non-toxic compatible lubricants such as sodium lauryl sulfate and magnesium stearate, coloring agents, releasing agents, coating agents, sweeteners, flavors, perfuming agents, preservatives, and antioxidants.

Immunization of a subject, or eliciting an immune response may involve delivery of a therapeutically effective amount of the composition to a subject in need or at risk of *C. difficile* infection, in an appropriate amount and for an adequate time as may be necessary to achieve the goal. The composition can be used as a preventive or therapeutic measure to promote immunity to infection or re-infection by *C. difficile*.

The therapeutically effective amount may be determined on an individual basis or on the basis of the established amount necessary for an effective promotion of antibody formation. Appearance of antibodies in serum, which are specific for the toxins of *C. difficile*, or disappearance of disease symptoms can be evaluated clinically. The dosage for an individual subject is chosen in view of the subject to be treated. Dosage and administration are adjusted to provide sufficient levels of the active agent(s) or to maintain the desired effect. Factors which may be taken into account include the severity of the disease state, contact with infectious agent in the past, potential future contact; age, weight, gender of the subject, diet, time and frequency of administration, drug combinations, reaction sensitivities, and tolerance/response to therapy. Sustained release compositions might be administered less frequently than fast-acting compositions.

A therapeutic dose may encompass from about 1 µg per kg, for example, about 5, 10, 50, 100, 500 µg per kg, at least about 1 mg/kg, 5, 10, 50 or 100 mg/kg body weight of the purified toxin vaccine per body weight of the subject, although the doses may be more or less depending on age, health status, history of prior infection, and immune status of the subject as would be known by one of skill in the art of immunization. Doses may be administered as a bolus or repeated at appropriate intervals, or via an infusion at a constant or intermittent rate.

Compositions can be administered to subjects through any acceptable route, such as topically (as by powders, ointments, or drops), orally, rectally, mucosally, sublingually, parenterally, intracisternally, intravaginally, intraperitoneally, bucally, ocularly, or intranasally.

Liquid dosage forms for oral administration may include emulsions, microemulsions, solutions, suspensions, syrups and elixirs. Liquid dosage forms may contain inert diluents such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils such as cottonseed, groundnut, corn, germ, olive, castor, and sesame oils, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required.

Injectable preparations, such as sterile injectable aqueous or oleaginous suspensions may be formulated according to the known art using suitable dispersing or wetting agents and suspending agents. The sterile injectable preparation may also be a sterile injectable solution, suspension or emulsion in a non-toxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized prior to addition of spores, for example, by filtration through a bacterial-retaining filter, or by incorporating sterilizing agents in the form of sterile solid compositions which can be dissolved or dispersed in sterile water or other sterile injectable medium prior to use.

It is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral, mucosal or sublingual administration include capsules, tablets, pills, powders, and granules. In such solid dosage forms, the active agent is mixed with at least one inert, pharmaceutically acceptable excipient or carrier such as sodium citrate or dicalcium phosphate, fliers or extenders such as starches, sucrose, glucose, mannitol, and silicic acid, binders such as, for example, carboxymethylcellulose, alginates, gelatin, polyvinylpyrrolidinone, sucrose, and acacia, humectants such as glycerol, disintegrating agents such as agar-agar, calcium carbonate, potato or tapioca starch, alginic acid, certain silicates, and sodium carbonate, solution retarding agents such as paraffin, absorption accelerators such as quaternary ammonium compounds, wetting agents such as, for example, cetyl alcohol and glycerol monostearate, absorbents such as kaolin and bentonite clay, and lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, such as tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

EXAMPLES

Example 1

Translocation Domain Mutations Affecting Cellular Toxicity Identify the *Clostridium difficile* Toxin B Pore Introduction Homologous toxins TcdA and TcdB of *C. difficile* impact colonic epithelial cells upon infection. Binding to target cells triggers internalization of these toxins into acidified vesicles, whereupon cryptic segments from within the 1050 amino acid translocation domain unfurl and insert into the membrane of the epithelial cell, creating a transmembrane passageway to the cytosol. Current understanding of pore-formation and the subsequent translocation of the upstream cytotoxic domain to the cytosol is limited by the lack of information regarding the identity and architecture of the transmembrane pore. In this Example, through systematic perturbation of conserved sites within predicted membrane-insertion elements of the translocation domain, highly sensitive residues have been found, clustered between amino acids 1035 and 1107, that when individually mutated reduce cellular toxicity by as much as >1000-fold. It is shown that defective variants are defined by impaired pore-formation in planar lipid bilayers and biological membranes, resulting in an inability to intoxicate cells through either apoptotic or necrotic pathways. Further, unexpected similarities were uncovered between the pore-forming "hotspots" of TcdB and the well-characterized α-helical diphtheria toxin translocation domain. Together, there is provided insight into the structure and mechanism of formation of the translocation pore for this important class of pathogenic toxins.

The structural features of the pore are described, and mutants are described which prevent pore-formation, showing reduced toxicity to host cells. These findings reveal information about the translocation pore, and provide the basis for a strategy to target toxins therapeutically.

In this Example, the initial goal was to identify the determinants of pore-formation and translocation through a comprehensive mutagenesis study using the *B. megaterium* platform. It was found, early in this pursuit, that site-specific mutagenesis of the inherently AT-rich toxin sequence (i.e., G+C=27%) using the *B. megaterium* system was laborious and inefficient. To address this, a GC-enriched copy of TcdB was generated (approximately G+C=45%) with codons optimized for *E. coli* expression. This permitted high throughput probing of the translocation domain. Several single point mutations were identified, clustering to within the hydrophobic region of the delivery domain, resulting in major defects in pore-formation and translocation. The unexpected similarity of the identified pore-forming region to that of the translocation domain of DT is reported. An α-helical model is described for the translocation pore of TcdB and homologous pathogenic toxins.

Materials and Methods

Expression and Purification of Recombinant TcdB from *Bacillus megaterium*.

Recombinant TcdB wild-type was a *B. megaterium* expression vector pH is 1522 encoding the strain VPI10463 obtained from Dr. Hangping Feng. Proteins were expressed and purified as previously described (Yang et al. (2008) BMC Microbial 8:192).

Expression and Purification of Recombinant Codon-Optimized TcdB constructs.

Codon-optimized TcdB sequence was synthesized (GenScript™) to increase GC percentage to 45%. The codon-optimized gene was cloned into an *E. coli* expression vector pET28a and transformed into *E. coli* BL21 DE3 competent cells and expressed as C-terminal His-tagged proteins.

Mutagenesis of TcdB Mutants.

Single point mutations were made in the TcdB codon-optimized sequence using QuickChange™ lightning multi-mutagenesis kit (Agilent Technologies, Santa Clara, Calif.). Sequenced plasmids with confirmed mutations were transformed and expressed using the same conditions as wild-type.

Small-Scale Expression of TcdB Mutants.

Plasmids expressing TcdB mutants were transformed into *E. coli* BL21 DE3 cells. Overnight cultures were prepared in a 24-well block (BD biosciences) in 5 mL. Cells were harvested by centrifugation and resuspended in buffer (20 mM Tris, 500 mM NaCl pH 8.0 and protease inhibitor) and lysed by lysozyme (BioShop™) as manufacturer's instructions followed by centrifugation at 4,000 g for 20 min. Supernatants were collected. The concentration of each full-length mutant protein in the lysates was determined by densitometry (Image Lab 3.0).

Cell Viability Assay.

TcdB variants were added to CHO-K1 cells at a serial dilution of 1/3 starting at 1 nM. Cell viability was assessed after 48 h by PrestoBlue® Cell Viability Reagent (Life technology). Fluorescence was read on a Spectramax M5 plate reader (Molecular Devices).

Rubidium Release Assay.

$^{86}$Rb+ release assay was performed as previously reported by Genisyuerek S, et al. (2011). Briefly, CHO-K1 cells were seeded in 96-well plates supplemented with 1 µCi/ml $^{86}$Rb+ (PerkinElmer) at a density of 1×10$^4$ cells per well. $^{86}$Rb+ released was determined by liquid scintillation counting with TopCount NXT (PerkinElmer).

TNS Fluorescence Assay.

pH-induced conformational changes of TcdB were assessed as described previously (Lanis et al. (2010) PLoS Pathog 6(8):e1001061). Assay plates were read in Spectramax M5 plate reader (Molecular Devices).

Black lipid bilayer experiments. Lipid bilayer experiments were performed essentially as described previously (Melnyk & Collier (2006) Proc Natl Acad Sci USA 103(26): 9802-9807). Both cis and trans compartments contained 1 ml of solutions containing 1 M KCl; 10 mM Tris pH 7.4. Pore-formation was initiated by adding appropriate amounts of 2 M HCl to the cis compartment to lower the pH to 4.5.

CellTiterGlo™ ATP Assay.

Cell death assay was performed as previously described (Chumbler et al. (2012) PLoS Pathog 8(12):e1003072.). Assay plates were read in Spectramax M5 plate reader (Molecular Devices).

Expression and Purification of Recombinant TcdB from *Bacillus megaterium*.

The template used for mutagenesis and clone for production of recombinant TcdB wild-type and mutant was a *B. megaterium* expression vector pHis 1522 encoding the strain VPI10463 obtained from Dr. Hangping Feng. Proteins were expressed and purified as described by Yang et al. (2008) BMC Microbiol 8:192.

Expression and Purification of Recombinant Codon-Optimized TcdB Constructs.

Codon-optimized TcdB sequence was synthesized (GenScript™) to increase GC percentage to 47%. The codon-optimized gene was cloned into an *E. coli* expression vector pET28a and transformed into *E. coli* BL21 DE3 competent cells and expressed as C-terminal His-tagged proteins. 50 mL of overnight culture was inoculated into 1 L of LB with 50 µg/ml Kanamycin and induced at OD600 of 0.6 with 0.5 mM IPTG at 37° C. for 4 h. Cells were harvested by centrifugation and re-suspended with lysis buffer (20 mM Tris pH 8.0, 0.5M NaCl, protease inhibitor) and lysed by an EmulsiFlex™ C3 microfluidizer (Avestin) at 15,000 psi. After lysing, lysate were centrifuged at 18,000 g for 20 min. Proteins were purified by Ni-affinity chromatography using HisTrap FF column (GE Healthcare). Fractions containing TcdB were verified and pooled with a 100,000 MWCO ultrafiltration device. 10% of glycerol was added; protein concentration was calculated by densitometry (Image Lab 3.0).

Mutagenesis of TcdB Mutants.

Single point mutations were made in the TcdB codon-optimized sequence using QuickChange™ lightning multi-mutagenesis kit (Agilent technologies). Plasmids with correct mutations were transformed and expressed using the same conditions as wild-type.

Small-Scale Expression of TcdB Mutants.

Plasmids expressing TcdB mutants were transformed into *E. coli* BL21 DE3 cells. Overnight culture were prepared in 24 well block (BD biosciences) in 5 mL. 250 µl of overnight culture were inoculated into 5 ml of LB with Kanamycin and induced at OD600 of 0.6 with 0.5 mM IPTG at 37° C. for 4 h. Cells were harvested by centrifugation and resuspended in buffer (20 mM Tris, 500 mM NaCl pH 8.0 and protease inhibitor (Sigma)) and lysed by lysozyme (Bioshop) as manufacturer's instructions followed by centrifugation at 4,000 g for 20 min. Supernatants were collected. The concentration of each full-length mutant protein in the lysates was determined by densitometry (Image Lab 3.0).

Details of Cell Viability Assay.

CHO-K1 Cells (Chinese hamster ovary cells) were cultured in Ham's F-12 medium (Wisent) with 10% fetal calf serum (FBS, Wisent) and 1% penicillin and streptomycin (Wisent). CHO-K1 cells were seeded at a concentration of 8,000 cells/well in 96-well CellBind plates (Corning). The next day, medium was exchanged with serum free medium and cells were intoxicated by adding TcdB toxins at a serial dilution of 1/3 starting at 1 nM. After intoxication, cells were incubated at 37° C., 5% CO2 for 48 h. Serum (FBS) was added back to cells 24 h after intoxication to a final concentration of 10%. The Cell viability after 48 h was assessed by PrestoBlue® Cell Viability Reagent (Life technology). Fluorescence was read on a Spectramax M5 plate reader (Molecular Devices).

Details of Rubidium Release Assay.

$^{86}$Rb+ release assay was performed as previously reported (2) with slight modifications. Briefly, CHO-K1 cells were seeded in 96-well plates in the medium (Ham's F-12 with 10% FBS), supplemented with 1 µCi/ml $^{86}$Rb+ (PerkinElmer) at a density of 1×10$^4$ cells per well. Cells were incubated at 37° C., 5% CO$_2$ overnight. Medium was exchanged with fresh growth medium with 100 nM bafilomycin A1 (Sigma) and continued to incubate for another 20 min. Then, cells were chilled on ice and ice-cold medium containing TcdB mutants (10 nM) was added. Cells were kept on ice for toxin binding for 1 h at 4° C. before they were washed with ice-cold PBS twice to remove unbound toxins. pH-dependent insertion into the plasma membrane was induced by warm, acidified growth medium (37° C., pH 4.5 or pH 7.5) for 5 min at 37° C. After 1 hour of further incubation on ice, medium containing released 86Rb+ was removed from cell plate and amount of $^{86}$Rb+ released was determined by liquid scintillation counting with TopCount™ NXT (PerkinElmer).

In Vitro Glucosyltransferase Assay.

10 nM of TcdB mutants were incubated with 0.8 μM GST-Rac1 (0.2 μg/μl, Sigma) in 25 μM UDPglucose in glucosylation buffer (50 mM HEPES, 100 mM KCl, 2 mM $MgCl_2$ and 1 mM $MnCl_2$, pH 7.5) for 60 min. The reaction was stopped by addition of Laemmli loading buffer with β-mercaptoethanol and boiling at 95° C. for 5 min. The proteins were separated on a 5%-12% gradient polyacrylamide gel by SDS-PAGE and then proteins were transferred to nitrocellulose with the iBlot device (Invitrogen). Glucosylated GST-Rac1 was detected by standard western blotting with an antibody that specifically recognizes the non-glucosylated form of Rac1 (Mab 102, ED Biosciences), anti-GST antibody (GenScript) and HRP-conjugated anti-mouse-IgG (GE healthcare).

TNS Fluorescence Assay.

pH-induced conformational changes of TcdB were assessed as described by Lanis et al. (2010) PLoS Pathog 6(8):e1001061. 2 μg of TcdB was prepared in buffer having a pH ranging from 4 to 7. 2-(p-toluidiny)-naphthalene-6-sulfonic acid, sodium salt (2,6-TNS, Invitrogen) was added at a final concentration of 150 μM. The final volume was 250 μl and mixed in 96-well black plate (Corning). Mixtures were incubated at 37° C. for 20 min. The plate was analyzed in Spectramax™ M5 plate reader (Molecular Devices) with excitation of 366 nm and an emission scan of 380 to 500 nm.

Black Lipid Bilayer Experiments.

Lipid bilayer experiments were performed as described previously with modifications (Melnyk & Collier (2006) Proc Natl Acad Sci USA 103(26):9802-9807). Briefly, membranes were made by painting diphytanoyl phosphatidylcholine (Avanti Polar Lipids) in decane across a 200-μm aperture in a Delrin cup by using the brush technique. Both cis and trans compartments contained 1 ml of solutions containing universal bilayer buffer as described by Kreimeyer et al. (2011) Naunyn Schmiedebergs Arch Pharmacol 383(3): 253-262 (1 M KCl; 10 mM Tris pH 7.4). Translocation was initiated by adding appropriate amounts of 2 M HCl to the cis compartment to lower the pH to 4.5. Each compartment was stirred continuously throughout the experiment with a small stir bar. Agar salt bridges linked Ag/AgCl electrodes in 3 M KCl. The current was amplified through a BC-525C integrating bilayer clamp amplifier (Warner Instruments, Hamden, Conn.), filtered at a frequency of 0.1 kHz by a low-pass eight-pole Bessel filter and computer-displayed through an analog/digital converter.

Further Details of Cell Death Assay.

Cell death assay was performed as previously described (Chumbler et al. (2012 PLoS Pathog 8(12):e1003072.). Briefly, IMR-90 Cells (cultured in EMEM, 10% FBS, 5% $CO_2$) were seeded in 96-well Cellbind™ plate at a concentration of 8,000 cells/well. The next day, the growth medium was exchanged with serum free EMEM and incubated at 37° C., 5% $CO_2$ for 60 min. TcdB toxins were added to cells in dilutions starting at 30 nM. After intoxication, cells were incubated at 37° C., 5% $CO_2$ for 3 h. The amount of ATP was assessed with CellTiterGlo™ as per the manufacturer's instructions (Promega). Plates were read in Spectramax™ M5 plate reader (Molecular Devices).

Results

Patterns of Hydrophobicity and Secondary Structure Suggest a Helical Pore for TcdB To begin to unravel the determinants of pore formation and translocation, hydrophobicity, sequence conservation and predicted secondary structure elements of the 1050 amino acid translocation domain were analyzed. Seven stretches of hydrophobicity were identified in TcdB: 985-1005, 1018-1036, 1037-1056, 1064-1089, 1091-1112, 1261-1281, and 1310-1330 as shown in the top panel of FIG. 5. The latter two regions were excluded since neither was predicted to be hydrophobic in the homologue from Clostridium novyi (TcnA).

FIG. 5 shows a hydropathy analysis of the translocation domain. In the top panel, hydropathy analysis of the entire translocation domain of TcdB was performed using a membrane protein topology prediction method (TMHMM v2.0) that uses a hidden Markov model to predict transmembrane helices (Krogh et al. (2001) J Mol Biol 305(3):567-580). Seven distinct peaks of hydrophobicity are evident; five within the previously described hydrophobic region, along with two smaller regions of hydrophobicity between 1280-1350, which were poorly conserved among homologous toxins and thus not pursued. In the bottom panel, hydropathy analysis of the 172 residue hydrophobic region is illustrated, showing predicted hydrophobic helices (HH1-HH5). The inset shows a hydropathy analysis of the 173 amino acid diphtheria toxin translocation domain with established α-helical segments predicted to comprise the translocation pore of DT.

Alignment of the translocation domain of the large Clostridial Toxin family using ClustalX2.1 was conducted. Residues 800-1880 were evaluated using TcdB numbering. Only HH1-HH5 were predicted to be hydrophobic, whereas HH6 and HH7 were predicted in all homologues except for TcnA from Clostridium novyi.

Notably, the former five hydrophobic segments fell within the "hydrophobic region" of the translocation domain (i.e., 956-1128). The length of the four hydrophobic segments that all were between 18 to 25 amino acids, combined with the absence of any alternating hydrophobic-hydrophilic "β-barrel" motifs in this region, suggest that the membrane-inserted form of these segments adopt an α-helical conformation. When the primary sequence of the hydrophobic region was analyzed using secondary structure propensity algorithms, five α-helical structural elements with four intervening disordered loops were predicted. Secondary structure prediction for the translocation domain of TcdB was undertaken using JPRED3, and predicted helical regions were observed.

Positing an α-helical mode of membrane insertion, the well-characterized α-helical diphtheria toxin (DT) translocation domain was evaluated for comparison. The hydrophobic helices (TH5-6/7 and TH8-TH9) previously shown to be involved in pore-formation and translocation of DT were correctly mapped by this analysis (FIG. 5, bottom panel). Unexpectedly, it was found that the general pattern of hydrophobicity was strikingly similar for the 173-residue translocation and the 172-residue hydrophobic region of TcdB. Three peaks of similar length and amplitude were predicted in both toxins. The functional link between DT translocation and the hydrophobic region of TcdB is considered further, below.

Validation of a GC-Enriched Toxin B Gene for Mutagenesis and Expression in *E. coli*

The observation that the putative pore-forming hydrophobic regions of the translocation domain were localized within the 172 amino acid window led to the investigation of which specific amino acids in this region were involved in pore-formation and translocation. To circumvent experimental barriers associated with generating many mutants to the AT-rich Clostridial toxin gene (i.e., G+C=27%), a copy of the 7,098 base pair TcdB gene was synthesized in which the G+C content was increased to 45%. This mutagenesis-competent copy of TcdB was then cloned into an *E. coli* expression plasmid in order to enable expression in a host that is more amenable for high throughput characterization than the existing *Bacillus megaterium* expression system.

To validate the newly constructed GC-enhanced copy of TcdB, the structure and function of *E. coli* produced TcdB was characterized and compared it to benchmark standards. TcdB produced in *E. coli* was indistinguishable from TcdB produced in the well-validated *B. megaterium* system showing equal potency on CHO cells toxicity. Validation of GC-enriched, codon-optimized TcdB protein was evaluated based on *E. coli* expression. Autoprocessing activity of recombinant toxins was evaluated. Recombinant TcdB variants were treated with 100 µM InsP6 (+) or PBS (−) for 3 h and cleavage was visualized by Western blot by probing with an anti-GTD antibody. Further, GTD activity of recombinant toxins was evaluated. GST-Rac1 was treated with recombinant toxins, and the level of glucosylation was determined by Western blot analysis using Mab102 that recognizes unglucosyated Rac1 and an anti-Rac1 antibody to determine total Rac1. Functional activity of recombinant toxins was assessed. Recombinant TcdB constructs were added to CHO cells over a range of concentrations. Cellular viability was quantitated 48 h later by measuring the fluorescence of cells treated with the cell viability reagent (PrestoBlue®).

The cytotoxicity of both purified toxin and soluble clarified lysate from induced *E. coli* on Chinese Hamster Ovary (CHO) cells was next measured, and compared this to uninduced controls, a glucosyltransferase defective mutant (D270A), and WT TcdB produced in *B. megaterium*. Purified WT toxins produced in either system yielded similar potency on CHO cells, whereas D270A was similarly inactive when produced in either system. Importantly, WT toxin produced in *E. coli* clarified soluble lysate was equipotent with the purified toxins (after normalizing toxin concentration of toxin in crude lysates using densitometry). This set of experiments showed that *E. coli*-produced toxin is functional and further that there is no confounding contaminant in the *E. coli* preparations as evidenced by the complete lack of toxicity of the uninduced control on CHO cell viability.

High-Throughput Mapping of the Functional Determinants in the Translocation Domain With a robust system to probe toxin function in place, residues that were absolutely conserved among the LCT family members were probed, reasoning that functionally important residues would be conserved in homologous toxins. A double-mutant strategy was used in which each of the residues was mutated to both a highly disruptive residue (Lysine), and to a more conservative residue (Cysteine). The highly polar Lysine side chain was selected to increase the probability of identifying a membrane-spanning segment; introducing the polar and charged Lys side chain into a marginally hydrophobic membrane-inserting segment could be expected to prevent insertion of this segment and thus pore-formation. On the other hand, Cysteine, like Alanine, is a relatively benign substitution that can both help identify key functional residues and has the added downstream benefit of offering the possibility of attaching sulfhydryl probes in TcdB for structure/function studies.

Figure 6:
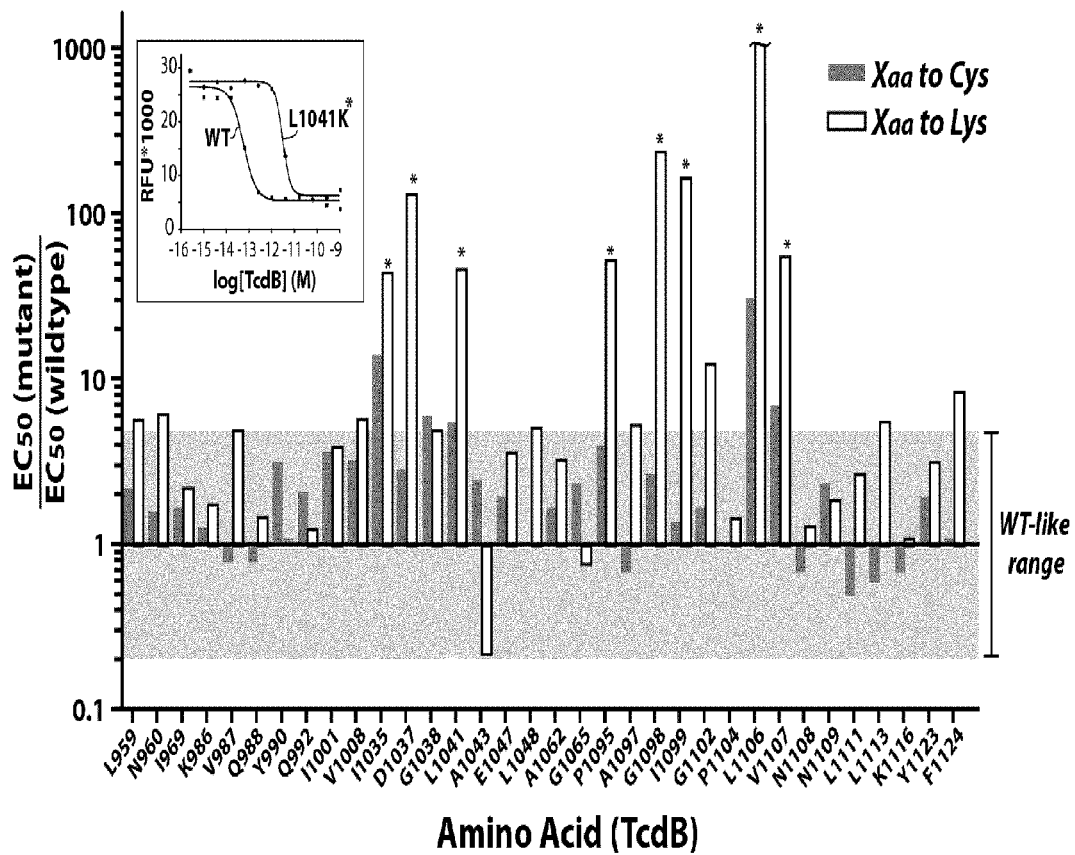
FIG. 6 shows high throughput mapping of the functional determinants in the translocation domain of TcdB, illustrating functional consequences on toxicity (EC50) of Cys and Lys substitutions in the hydrophobic region of TcdB.

The impact of each mutation on TcdB function was quantified by measuring the dose-dependent reduction in cell viability 48 hours post-toxin addition relative to wild-type TcdB, and results are shown in FIG. 6.

FIG. 6 shows high throughput mapping of the functional determinants in the translocation domain of TcdB. Functional consequences of Cys and Lys substitutions in the hydrophobic region of TcdB. Mutant soluble lysates were titrated onto CHO cells (using 3-fold dilutions) in 96-well plates and incubated for 48 h at 37° C. (n=4). In parallel, an aliquot of each mutant was used to measure the concentration using band densitometry after SDS-PAGE. 48 h later cell viability of treated cells was quantitated by measuring PrestoBlue® fluorescence using a SpectraMax M2 fluorescence microplate reader, as shown in the inset chart of sample titration curves of WT TcdB and L1041K mutant TcdB. Grey shading in FIG. 6 represents the wild-type-like range of activity (i.e., ±5-fold wild-type TcdB).

Of the nearly 90 mutants generated, only Y971 and L1048 were not expressed upon mutation, and thus were not evaluated further. Of the remaining mutants, eight residues that when mutated, gave rise to a greater than a 90% reduction in toxicity relative to WT (FIG. 6). As expected, for virtually all sites tested, mutation to Lysine was more detrimental to function than mutation to Cysteine. Four positions (i.e., D1037, G1098, I1099, and L1106) displayed a greater than a 99% reduction in toxicity of which L1106K was the most defective with an observed shift of over 1000-fold relative to wild-type TcdB. This surprising result was highly indicative of an atoxic holotoxin.

FIG. 3A and FIG. 3B, when taken together, show SEQ ID NO: 3, a nucleic acid sequence encoding wild-type TcdB (SEQ ID NO:1), showing codon CTG (bold and underlined in FIG. 3A), encoding L1106.

FIG. 4A and FIG. 4B, when taken together, show SEQ ID NO: 4, a nucleic acid sequence encoding a mutant of wild-type TcdB (SEQ ID NO:2) showing codon AAG (bold and underlined in FIG. 4A) encoding lysine at residue 1106 (thus, representing "L1106K").

Mutants displaying greater than a 10-fold reduction in toxicity were re-expressed in large scale and purified using Ni+-affinity chromatography and/or anion exchange chromatography and re-tested in triplicate. Excellent overall correlation was observed in potency between the soluble lysates and purified toxins, which both confirmed the screening results and further validated the soluble lysate screening approach.

Pinpointing the Nature of the Defects in TcdB that Diminish Function

Defective TcdB mutants were studied in detail to determine the mechanistic basis for their defects. To rule out the possibility that point mutations were causing gross and global misfolding of toxins, thus rendering them unable to intoxicate cells, the state of folding for each mutant was evaluated using the hydrophobic dye TNS, which displays increased fluorescence when binding to hydrophobic patches of polypeptide (i.e., unfolded proteins). In addition to confirming that all mutants tested were folded, these studies show that the pH dependence of unfolding was preserved for mutant toxins. Defective TcdB mutants are folded and display a similar pH-induced unfolding by TNS fluorescence. Defective mutants were all folded at neutral pH and began unfolding at pH <5. The two most defective mutants (G1098K and L1106K) show a similar unfolding profile to WT TcdB.

To address this further, the enzymatic activity of the glucosyltransferase domain was evaluated for activity in each defective mutant. All mutants tested showed comparable activity to WT TcdB with specific activities that were within ±2-fold wild-type levels, further suggesting that mutant toxins were otherwise folded.

Defective mutants were then tested for translocation domain-specific functions. The ability of each of the defective mutants and control toxins to release $^{86}$Rubidium ions from CHO-K1 cells upon binding to the cell surface and acidification of the medium to trigger insertion into the plasma membrane was tested as shown in FIG. 7, panel A.

Figure 7:
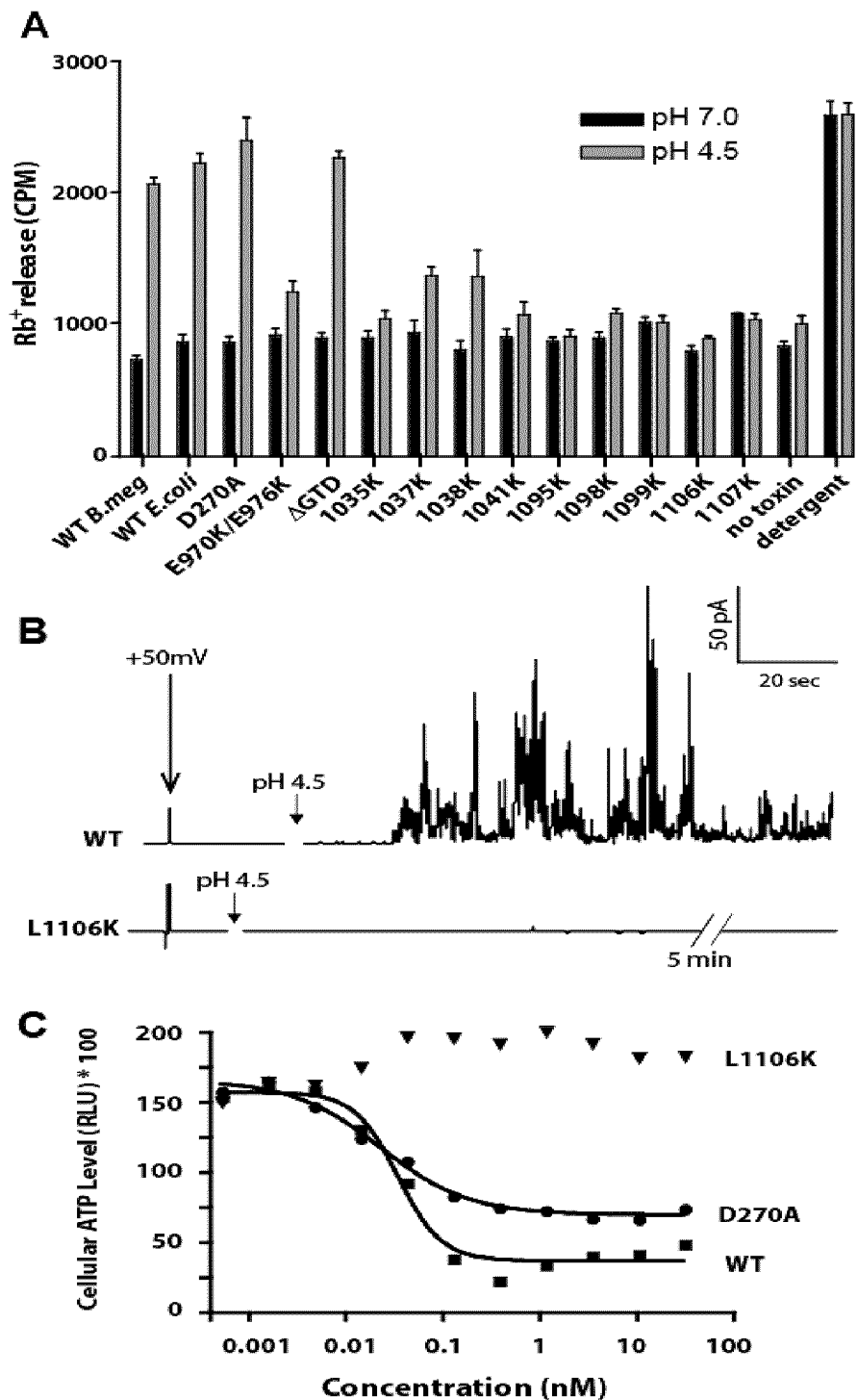
FIG. 7 provides characterizations of defective purified TcdB mutants. Panel A shows pore-formation on biological membranes for different. Panel B shows pore formation on planar lipid bilayers. Panel C shows effect of pore-formation on enzyme-independent cytotoxicity.

FIG. 7 shows a characterization of defective purified TcdB mutants. Panel A shows the characterization of pore-formation on biological membranes. Pore-formation of purified mutant toxins was tested on CHO cells pre-loaded with $^{86}$Rb+. Pore-formation was induced by acidification of the external medium (control pH 7.0; black bars. pH 4.5; grey bars)—see Methods for details of assay (n=5). Panel B shows pore formation on planar lipid bilayers. Approximately 100 pM of WT or L1106K toxin was added to the cis chamber of planar DiPhPC/n-decane membranes in buffer containing 1M KCl. After 2 minutes the pH of the cis chamber was dropped to pH 4.5 using a defined concentration of dilute HCl. Measurements were performed with +50 mV ($\psi$=+50 mV, cis-positive) at room temperature. Panel C shows the effect of pore-formation on enzyme-independent cytotoxicity. The high-dose acute cytotoxicity of purified WT TcdB, a glucosyltransferase-defective mutant (D270A), and a pore-formation defective mutant (L1106K). Constructs were tested on human IMR-90 fibroblasts under necrosis-like conditions as described previously (Chumbler et al. (2012) PLoS Pathog 8(12):e1003072).

Wild-type TcdB from all sources was able to form pores and release rubidium upon acidification to levels comparable to the detergent controls. As expected, the glucosyltransferase inactive mutant D270A, and a construct in which the entire GTD was removed (i.e., ΔGTD) were also able to form pores at low pH. In contrast, all of the defective mutant toxins tested showed defects in pore-formation, with most showing levels comparable to the no toxin control. Interestingly, two mutant toxins, 1037K and 1038K showed intermediate levels of pore-formation, suggesting that pore-formation was reduced, but not ablated under these conditions. Similarly, the previously identified mutant E970K/E976K, which is the only other mutant reported to date that affects pore-formation, showed a partial, but not complete reduction in pore-formation.

In parallel, pore-formation in synthetic lipid bilayers was tested using electrophysiological methods. As shown in FIG. 7, panel B (top trace), WT TcdB induced an increase in membrane activity at acidic pH (pH 4.5) with a holding potential of +50 mV ($\Delta\psi$=+50 mV, cis-positive). The observed Large and transient currents were reproducible and similar in character to previous planar lipid bilayer experiments of Genisyuerek et al. (2011, B. Mol Microbiol 79(6):1643-1654). By contrast, despite several attempts (n=8), the use of higher concentrations and extended traces, no channel activity was detected for the L1106K mutant, consistent with an inability to form ion-conductive pores as seen in FIG. 7, panel B.

Examining the Role of Pore-Formation on TcdB-Induced Necrosis

The experimental conditions used in this study to measure TcdB cytotoxicity depend on functional autoprocessing and glucosyltransferase domain functions. A second, alternative mode of cytotoxicity for TcdB that was found to be independent of autoprocessing and glucosyltransferase functions. See Chumbler et al. (2012). PLoS Pathog 8(12):e1003072. At higher doses of TcdB—which may be possible during infection—cells undergo a rapid necrotic-like cell death via an NADPH oxidase pathway, characterized by a rapid depletion of ATP. The pore-defective mutants identified here were utilized to examine the importance of pore-formation on this alternative mode of TcdB-mediated cell death. Whereas both WT TcdB, and the glucosyltransferase inactive D270A mutant equally induced a rapid depletion of ATP at 100 pM, no reduction was observed in cellular ATP for L1106K up to 100 nM, indicating that pore-formation is indeed required for the TcdB-mediated necrosis, see FIG. 7, panel C. In support of this, Donald et al., recently showed using the milder double mutant E970K/E976K, which partially reduces pore-formation, shifted the potency of a TcdB variant with attenuated GTD and CPD activity by ~100-fold. Under equivalent conditions, L1106K has a greater impact on pore formation than E970K/E976K.

Mapping the Determinants of Pore Formation onto a Model of the TcdB Pore

To place these functional data onto a structural framework, a model of the membrane-inserted form of TcdB was used, based on the predicted hydrophobicity and secondary structure of the hydrophobic region and using knowledge of DT to help orient the model.

Figure 8:
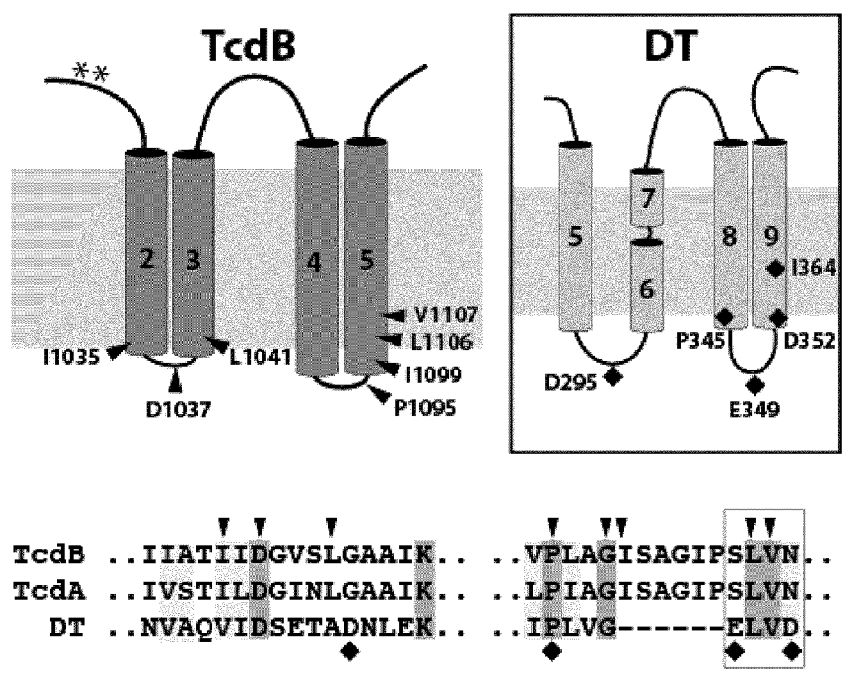
FIG. 8 shows a mapping of the functional determinants of pore-formation and translocation onto a working model of the TcdB translocation pore. A model of TcdA and of the "double-dagger" DT pore are also shown. TcdB sequences shown here are SEQ ID NO:5 ILATIIDGVSLGAAIK and SEQ ID NO:6 VPLAGISAGIPSLVN. TcdA sequences shown here are SEQ ID NO:7 IVSTILDGINLGAAIK and SEQ ID NO:8 LPIAGISAGIPSLVN. DT sequences shown here are SEQ ID NO:9 NVAQVIDSETADNLEK and SEQ ID NO:10 IPLVGXXXXXXELVD.

FIG. 8 provides a mapping of the functional determinants of pore-formation and translocation onto a working model of the TcdB translocation pore and the model of the "double-dagger" DT pore proposed originally by Choe et al (1992) Nature 357(6375):216-222.) and later supported by Wang & London (2009), Biochemistry 48(43):10446-10456. Four hydrophobic segments of ~20 amino acids are proposed to span the lipid bilayer in the pore state as two helical hairpins—similar to DT. Functionally important residues affecting membrane-insertion/pore-formation map to the cytosolic face of the membrane in TcdB and DT. Below the model is shown a ClustalX alignment of TcdB, TcdA and DT showing regions of conservation in the two pore-formation "hotspots" with defective mutants indicated as arrowheads (for TcdB) or diamonds (for DT). Residues within the boxed region (i.e., S1105-N1108 for TcdB, S1107-N1110 for TcdA and E349-D352 for DT) are highly susceptible to mutagenesis.

Mapping the residues that were identified as being sensitive to mutagenesis onto the TcdB model revealed two "hotspots" that conspicuously localized to the distal side of the membrane (FIG. 8). In forming the pore, these residues would be expected to traverse the greatest distance into the membrane relative to the proximal side of the membrane where the pre-pore residues before insertion. Intriguingly, when the four residues were mapped in the DT translocation domain previously shown to reduce DT-mediated toxicity by more than 100-fold, a similar phenomenon was observed; defective mutants localize to the distal end of the pore. In support of this model, shared residues were found within the hotspots that appear to be functionally important in both toxins. Asp-1037 in TcdB and Asp-295 in DT, though offset slightly in primary sequence alignments are positioned in the loop between the first two membrane-spanning helices and mutations to Lysine in both cases as shown here for TcdB and previously with DT resulting in a >100-fold shifted relative to WT toxin. In the loop region intervening the second helical hairpin hotspot, Pro-345 in TcdB is aligned with Pro-1095 in DT. Pro-345 in DT was previously shown to prevent pore formation and membrane insertion resulting in a 99% reduction in toxicity to Vero cells. Mutagenesis studies were conducted, showing that the P1095K mutation also prevents pore formation similarly giving rise to a ~95% reduction in toxicity (FIG. 6).

Finally, at the heart of the membrane-insertion region are the well-studied pore-formation/translocation defective DT mutants E349K and D352K, which were shown previously to reduce functional toxicity in Vero cells by >100-fold due to an impairment in membrane-insertion of the TH8-TH9 helical hairpin. Sandwiched between these two residues are L350 and V351 in DT, corresponding to the two defective mutants, L1106 and V1107 uncovered here in TcdB.

Discussion

Research over the past decade has provided tremendous insight into the structure and function of the pathogenic toxins of *Clostridium difficile*. Despite these significant advances, there remains a large gap in our understanding of the underlying structural and functional features that explain how the central translocation domain mediates the critical step of delivering the cytotoxic glucosyltransferase domains across the endosomal membrane into the cytosol. In this study we provide the first comprehensive analysis of the functional determinants of the translocation domain and offer a model of the TcdB pore. Using a synthetic GC-enriched copy of TcdB, we identified eight residues, between residues 1035 and 1107 that when mutated resulted in a greater than 90% decrease in function. One of these pore-formation defective mutants, L1106K, strikingly reduced TcdB toxicity by greater than 1000-fold relative to WT toxin. These key functional determinants are conserved in the members of the Large Clostridial Toxin family as well as among the different variants of TcdB. Alignment of the hydrophobic region of different forms/strains of TcdB was undertaken. Specifically, five TcdB strains were aligned as follows (with accession codes shown in parentheses): R20291 (YP_003217086), CD196 (YP_003213639), 8864 (CAC19891), 630 (YP_001087135) and 1470 (CAA80815). The eight residues resulted in a greater than 90% decrease in activity upon mutation. That these studies were conducted under conditions where autoprocessing and glucosyltransferase functions are required for cytotoxicity, argues that formation of this pore is required for translocation of the glucosyltransferase effector into cells.

Genisyuerek et al. (2011. Mol Microbiol 79(6):1643-1654) generated a series of internal-, amino-, and carboxy-terminal truncations of the translocation domain in order to delineate the determinants of pore formation and translocation for TcdB. They concluded that residues 1-1500 (with a receptor-binding domain) encompassed the translocation machinery enabling functional toxicity. They showed that a small fragment (i.e., 830-1025) was able to form channels in planar lipid bilayers. The appearance of ion channel activity in a synthetic lipid bilayer with fragments of a toxin, does not necessarily indicate the existence of the minimal translocation domain. Distinctions between the minimal channel forming region and the minimal translocation domain have been made previously for DT. For example, a C-terminal fragment of DT, containing only half of TH8 and all of TH9 formed channels in lipid bilayers that had similar electrophysiological properties as those formed by wild-type toxin, despite lacking the necessary determinants for translocation.

The data obtained in this example supports a model for the TcdB pore that is similar in principle to the double-hairpin model has been suggested previously for DT. Introducing a positive charge in regions that must travel furthest across the apolar bilayer during insertion to be the most detrimental to function.

The observation made in this Example, that a single point mutant within the translocation domain of TcdB can prevent pore formation and translocation, highlights the importance of this domain in pathogenesis.

Given the magnitude of the reduction in toxicity combined with the subtly of a single point mutation on holotoxin folding demonstrated in this Example, the defective single-point mutants described herein are useful for vaccine and/or monoclonal antibody development to neutralize these potent toxins.

Example 2

Crystal Structure of *Clostridium difficile* Toxin A

Overview

*Clostridium difficile* infection (CDI) is the leading cause of hospital-acquired diarrhea and pseudomembranous colitis. Disease is mediated by the actions of two toxins. TcdA and TcdB, which cause diarrhea, inflammation, and necrosis within the colon. The toxins are large (308 and 270 kDa, respectively), homologous (47% amino acid identity), glucosyltransferases that target and inactivate small GTPases within the host. The multi-domain toxins enter cells by receptor-mediated endocytosis and form pores upon exposure to the low pH of the endosome. Eukaryotic inositol-hexakisphosphate (InsP6) binds a cysteine protease domain (CPD) to activate an autoprocessing event that releases the N-terminal glucosyltransferase domain (GTD) into the cytosol. The molecular details of how low pH and InsP6 regulate the delivery of the GTD into the cell have not been defined. The crystal structure of a fully-toxic 1831 amino acid fragment of TcdA (TcdA1831) is described herein, which reveals a role for zinc in the regulation of toxin autoprocessing and an extended delivery domain that serves as a scaffold for the hydrophobic α-helices involved in pH-dependent pore formation. A surface loop of the delivery domain comprises a sequence that is strictly conserved among all large clostridial toxins. This loop and the sequence thereof is described herein for use in vaccines and therapeutics.

Methods

In general, $TcdA_{1831}$ was expressed in *Bacillus megaterium* and purified to homogeneity by affinity chromatography and gel filtration. The protein was crystallized and diffraction data were collected on LS-CAT beamline 21-D at the Advanced Photon Source (USA). The structure was determined with phases from mercury using heavy atom methods. Data collection and refinement statistics not shown. XAS and ICP-MS were used to detect zinc bound to the toxin in solution. Viability, rubidium release, and Rac1 glucosylation assays were conducted in a cell culture model to assess toxin activity.

Plasmid Construction and Point Mutants.

Previously described plasmids for the recombinant expression of TcdA, $TcdA_{1831}$, and TcdB (Pruitt et al., 2010 & Pruitt et al., 2012) were used as templates for mutant proteins generated. Mutations were introduced by site-directed mutagenesis using the QuickChange protocol. TcdB C698A was previously described (Chumbler et al., 2012). The plasmid encoding $TcdA_{DXD}$ was provided by Ralf Gerhard (Kreimeyer et al., 2011). $TcdA_{DXD}$ is a known TcdA protein with two point mutations: D286N and D288N. This renders the toxin inactive in its glucosyltransferase activity.

Protein Expression and Purification.

GST-Rac1 was expressed and purified as previously described (Pruitt et al., 2012). Toxin expression plasmids were transformed into *Bacillus megaterium* protoplasts according to the manufacturer's protocol (MoBiTec). Transformants were grown in LB containing 10 ug/ml tetracycline at 37° C., 220 rpm overnight to produce a seed culture. To 1 L of LB, 30 mL of the overnight seed was used as inoculum. The inoculated cultures were grown at 37° C. until their $A_{600}$=0.3-0.4. Protein expression was induced using 5 g/L of D-xylose solid (TCI, X0019). After approximately 4 more hours at 37° C., 220 rpm, the cells were harvested into 1 L bottles at 4° C. and 5000×g for 30 minutes. Pellets were resuspended in buffer containing 20 mM Tris, pH 8.0, 300 mM NaCl, 10 μg/ml DNaseI, protease cocktail (Sigma, P8849), and 20 μg/ml lysozyme. The suspensions were homogenized using a dounce homogenizer and then lysed at room temperature at 25,000 psi (Constant Cell Disruption Systems). The lysates were placed on ice then centrifuged at 18,000 rpm in a JA-20 fixed-angle rotor for 25 minutes at 4° C. After filtering the chilled supernatants through 0.22 mm filters, the proteins were purified using nickel affinity chromatography at 4° C. Further purification was performed at room temperature using anion exchange chromatography followed by gel-filtration chromatography into 20 mM Tris, pH 8.0, 100 mM NaCl.

Crystallization.

$TcdA_{1831}$ and S1329C $TcdA_{1831}$ were concentrated to 10 mg/ml in 20 mM Tris, pH 8.0, 100 mM NaCl. Crystallization was performed using the hanging drop method at 21° C. with a 1:1 ratio of protein to mother liquor. The mother liquor formulation for WT crystals was 100 mM Bis-Tris, pH 6, 11% PEG 4000, 30-50 mM guanidium chloride (GuCl). The mother liquor formulation for the S1329C crystals was 100 mM Bis-Tris, pH 5.8, 8% PEG 4000, 50 mM GuCl. Crystals were exchanged into appropriate mother liquor containing 20% glycerol, mounted on cryo loops, and flash cooled in liquid nitrogen.

Heavy atom derivatives of $TcdA_{1831}$ were prepared by soaking crystals in the appropriate mother liquor containing either 5 mM mercuric chloride for 90 minutes, 5 mM mercuric chloride for 3 days, 1 mM gold (III) chloride hydrate for 40 min, or 1 mM $K_2PtCl_2$ for 40 minutes. Heavy atom derivatives of S1329C $TcdA_{1831}$ were prepared by soaking crystals in 5 mM mercuric chloride for 3 days.

Structure Determination and Refinement.

X-ray data were collected from single crystals on LS-CAT beamline 21 ID-D at the Advanced Photon Source (Argonne, Ill.) at 100° K. Diffraction data were indexed, integrated, and scaled using XDS (Kabsch, 2010) or HKL2000. The two mercury datasets were compared to the native dataset using multiple isomorphous replacement with anomalous scattering in SHARP. The analysis revealed five mercury sites in the two mercury datasets, differing only in their occupancies, and was consistent with the expectation that each protein monomer would have five free cysteine residues. The heavy atom positions were used to calculate initial phases, which were included in an auto-building protocol in PHENIX. The fragments generated by auto-building guided manual placement of the apo-GTD structure (PDB ID 3SS1) (Pruitt, 2012). Phases from the GTD model were combined with the phases from SHARP to calculate a new map and initiate a new round of autobuilding. The fragments generated through autobuilding allowed for manual placement of the CPD (PDB ID 3H06). Phases from the combined GTD and CPD model were combined with the phases from SHARP to calculate a new map and initiate new rounds of automated and manual building. Further phase improvement came from multi-crystal averaging.

The working model (consisting of the GTD, most of the CPD, and a series of unconnected fragments from the delivery domain) was used as search model for molecular replacement into the native, platinum, and gold datasets. The models and phases from each dataset were subjected to multi crystal averaging and density modification in PHENIX and resulted in excellent quality maps. One area of ambiguity was resolved through site specific introduction of a Hg atom: crystals of a S1329C $TcdA_{1-1832}$ mutant were derivitized with mercuric chloride, and the sixth heavy atom site was identified using PHENIX. The model was generated through an iterative process of manual building in Coot and refinement using Phenix.

The final model reflects the 50-3.25 Å native dataset ($R_{cryst}$=22%, $R_{free}$=26%) with 92.6% of the residues in the most favored regions of the Ramachandran plot with 0.3% outliers. The model contains residues 4-944 and 951-1806 along with 1 zinc atom.

X-Ray Absorption Spectroscopy.

X-ray absorption spectroscopy (XAS) experiments were carried at beamline X3B of the National Synchrotron Light Source, which was equipped with a sagitally focusing Si(111) double crystal monochromator and a Ni-coated mirror for harmonic rejection. A He Displex cryostat was used for temperature control (~15K typical sample temperatures). Fluorescence detection was provided by a 31-element solid-state germanium detector array (Canberra Industries, Inc., Meriden, Conn., USA).

Samples of TcdA (10 mg/mL) and buffer blanks were loaded into 30 μL polycarbonate cuvettes wrapped in 1 mil Kapton tape and then frozen by immediate immersion in liquid nitrogen. The Kα fluorescence emission spectra from TcdA and buffer samples in the X-ray beam (incident energy=10 keV) were examined. There was a significant increase in the total Zn fluorescence counts for the TcdA sample compared to buffer, while fluorescence for the Mn—Cu series was unchanged. XAS measurements were therefore carried out at the Zn K-edge on TcdA, over an energy range of 9.46-10.3 keV. Internal energy calibration was provided by simultaneous measurement of a Zn metal foil, with the first inflection point of the edge set to a reference energy of 9659 eV. Calibration and averaging of XAS data was carried out using Athena.

ICP-MS.

Proteins were prepared as described above and dialyzed overnight into metal free buffers. TcdB proteins were maintained in 20 mM HEPES pH 6.9, 50 mM NaCl, whereas $TcdA_{1831}$ proteins were dialyzed into 100 mM BisTris pH 6.0, 50 mM NaCl to reflect the crystallization conditions. Protein samples were analyzed for metal content by utilizing 50 μL of the protein solution and diluting in 2.5% (v/v) nitric acid (Sigma-Aldrich, TraceSELECT quality) to a final volume of 3 mL for ICP-MS analysis. In samples with significant precipitation after acidification, the samples were centrifuged at 15,000×g for 20 minutes to pellet any precipitate, and the solution transferred to a fresh tube for measurement. The diluted samples were analyzed for $^{66}Zn$, $^{55}Mn$, $^{63}Cu$, and $^{60}Ni$ using a 1-30 ppb standard curve utilizing stock solutions (Perkin Elmer). Analyses were performed using a PerkinElmer ELAN DRCII ICP-MS. The instrument was equipped with a Microflow PFA-ST concentric nebulizer with a 100 μL/min self-aspiration capillary, a cyclonic spray chamber, a quartz torch and nickel sampler/skimmer cones.

Germanium at 50 ppb was added as an internal standard using an EzyFit™ glass mixing chamber. Concentrations in ppb) were corrected for the dilution factor and the molar concentrations and molar ratios ($^{66}$Zn/protein) were determined for each sample.

Viability Assays.

Chinese hamster ovary cells CHO-K1 cells were cultured in Ham's F-12 medium (Wisent) with 10% FCS (FBS; Wisent) and 1% penicillin and streptomycin (Wisent). CHO-K1 cells were seeded at a concentration of 8,000 cells per well in 96-well CellBind plates (Corning). The next day, medium was exchanged with serum-free medium and cells were intoxicated by adding TcdA toxins at a serial dilution of 1/3 starting at 10 nM. After intoxication, cells were incubated at 37° C., 5% $CO_2$ for 48 h. Serum (FBS) was added back to cells 24 h after intoxication to a final concentration of 10% (vol/vol). The cell viability after 48 h was assessed by PrestoBlue Cell Viability Reagent (Life Technologies). Fluorescence was read on a Spectramax M5 plate reader (Molecular Devices).

Rubidium Release Assays.

$^{86}Rb^+$ release assay was performed described briefly, herein. Vero cells were seeded in 24-well plates in the medium (DMEM with 10% FBS), supplemented with 1 µCi/mL $^{86}Rb^+$ (PerkinElmer) at a density of 1×10$^5$ cells per well. Cells were incubated at 37° C., 5% $CO_2$ overnight. Medium was exchanged with fresh growth medium with 100 nM bafilomycin A1 (Sigma) and continued to incubate for another 20 min. Then, cells were chilled on ice and ice-cold medium containing TcdA mutants (10 nM) was added. Cells were kept on ice for toxin binding for 1 h at 4° C. before they were washed with ice-cold PBS twice to remove unbound toxins. pH-dependent insertion into the plasma membrane was induced by warm, acidified growth medium (37° C., pH 4.8 or pH 7.5) for 5 min at 37° C. Cells were incubated further on ice, medium containing released $^{86}Rb^+$ was removed from the cell plate at different time points, and the amount of $^{86}Rb^+$ released was determined by liquid scintillation counting with TopCount NXT (PerkinElmer). The percentage of $^{86}Rb^+$ release was calculated by subtracting the signal from untreated controls from each time point and dividing this difference by the signal from cells treated with 0.1% Triton.

Rac1 Glucosylation in Cells.

HeLa cells were synchronized by cooling to 4° C. and then intoxicated with 10 nM toxin or buffer. The cells were returned to 4° C. for 1 h, and then shifted to 37° C. for 3 hours. The cells were harvested and lysed (250 mM sucrose, 10 mM Tris pH 7.5, 3 mM imidazole), samples were boiled, and proteins were separated by SDS-PAGE. Samples were analyzed by Western with primary antibodies specific for unglucosylated Rac1 (BD, 610650) and total Rac1 (Millipore, clone 23A8). Binding of an anti-mouse, HRP-conjugated secondary antibody (Jackson ImmunoResearch Laboratories, 115-035-174) was detected with a LumiGLO™ kit (Cell Signaling) according to manufacturer's instructions.

Rac1 Glucosylation In Vitro.

100 nM toxin was added to 0.8 µM GST-Rac1 and 25 µM UDP-glucose (Sigma) in glucosylation buffer (50 mM HEPES pH 6.9, 100 mM KCl, 2 mM $MgCl_2$, 1 mM $MnCl_2$) for 3 hours. The reactions were stopped by adding Laemmli buffer and boiling. Samples were separated by SDS-PAGE and analyzed by Western using antibodies specific for glucosylated and total Rac1 (see above).

Results

Figure 9:
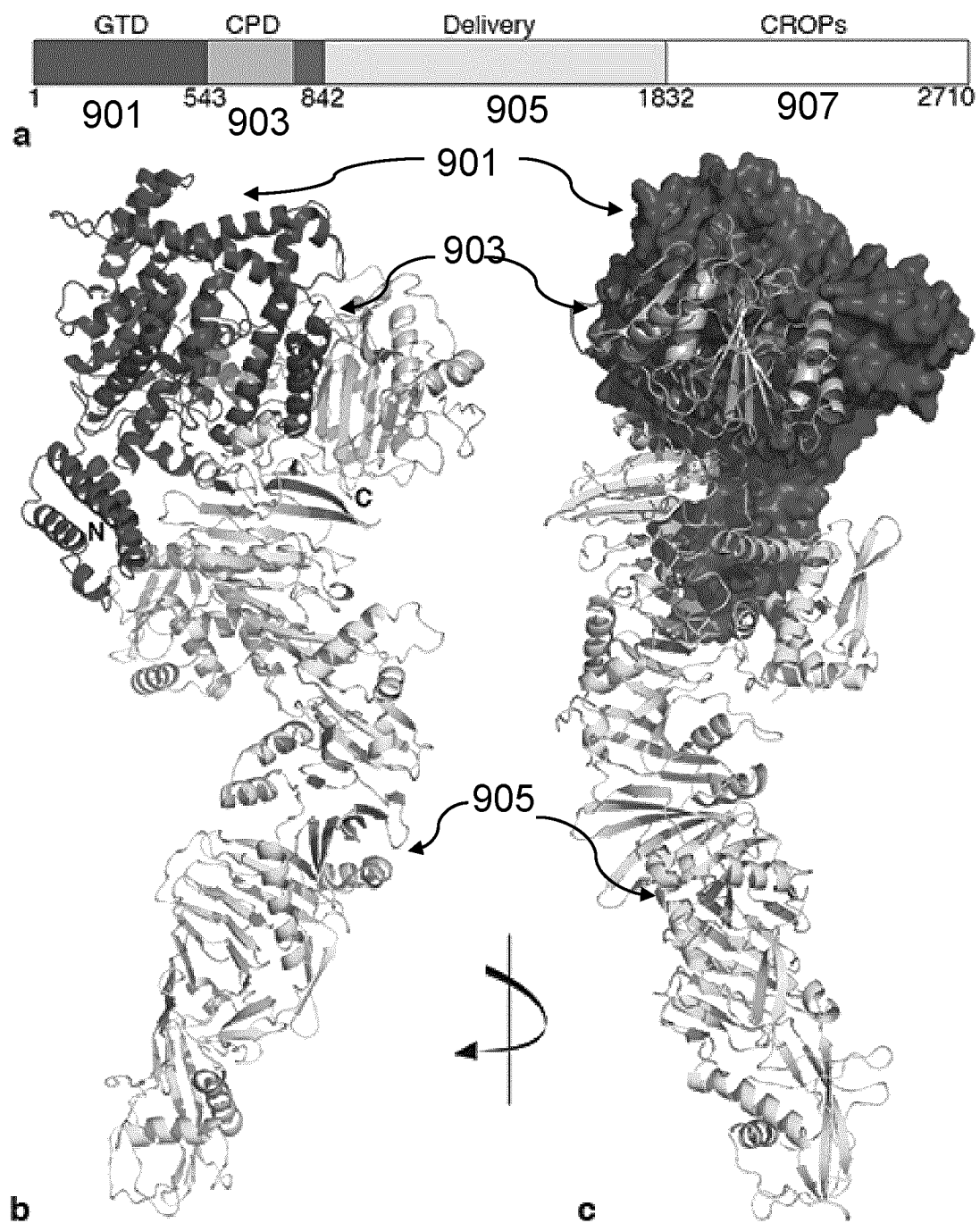
FIG. 9 shows the structure of TcdA.

FIG. 9 shows the Structure of TcdA. In panel (a), the TcdA primary structure can be divided into four functional domains: the glucosyltransferase domain (GTD) 901 initially indicated in red; the cysteine protease domain (CPD) 903 initially in blue; the delivery domain 905 initially in yellow; the CROPS domain 907 in white. In panel (b), a cartoon representation of the TcdA$_{1831}$ crystal structure shaded according to panel (a) with a zinc atom indicated. In panel (c), the structure in panel (a) was rotated 90° and the GTD is now shown as a surface view with the UDP-glucose binding site depicted.

Figure 10:
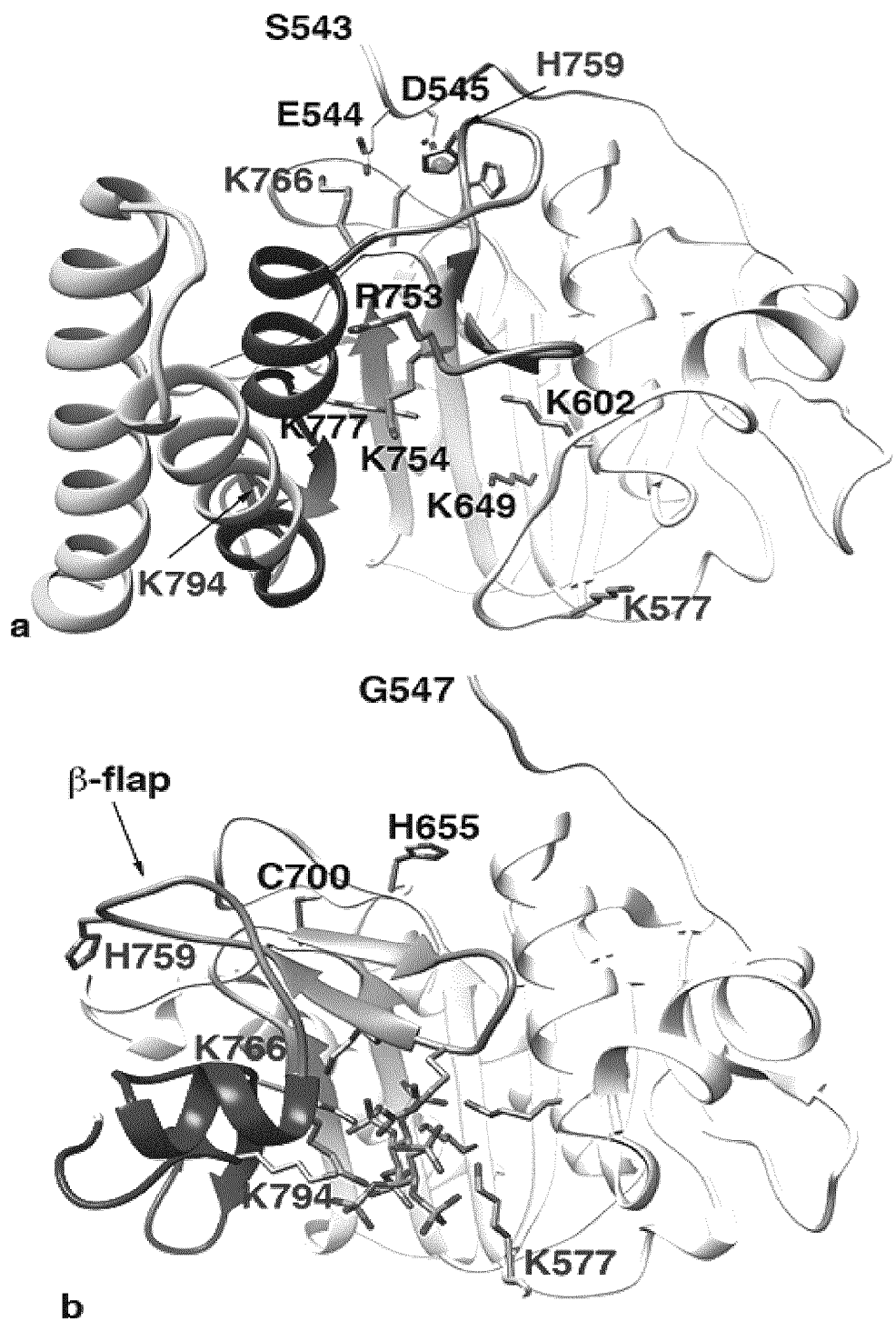
FIG. 10 provides data to illustrate that InsP6 binding induces a significant structural change in the CPD. Panel (a) shows the TcdA structure before InsP6 binding. Panel (b) shows the TcdA bound to InsP6.

FIG. 10 shows that InsP6 binding induces a significant structural change in the CPD. Shading is illustrated in shades of grey, which were initially represented in color. In panel (a), the CPD along with a small portion of the GTD and the three-helix bundle from the TcdA$_{1831}$ structure (oriented as in FIG. 9, panel (a)) is depicted with residues 522-542 (initially indicated in red), 543-745 initially in white, the 746-765 β-flap initially in light blue, and the three helix bundle (766-841) initially indicated in dark blue and yellow. A zinc atom (Initially shown in green) is bound in the CPD active site by H655, C700, and H759. Four lysines form the initial binding site for InsP6: K602, K649, K754, and K777. Comparison to panel (b), the InsP6-bound structure of the TcdA CPD suggests significant structural changes occur with InsP6 binding: the accumulation of 8 lysines and 1 arginine in the InsP6-binding site, a rearrangement of the β-flap and elements of the three-helix bundle, and displacement of H759 from the active site.

Figure 11:
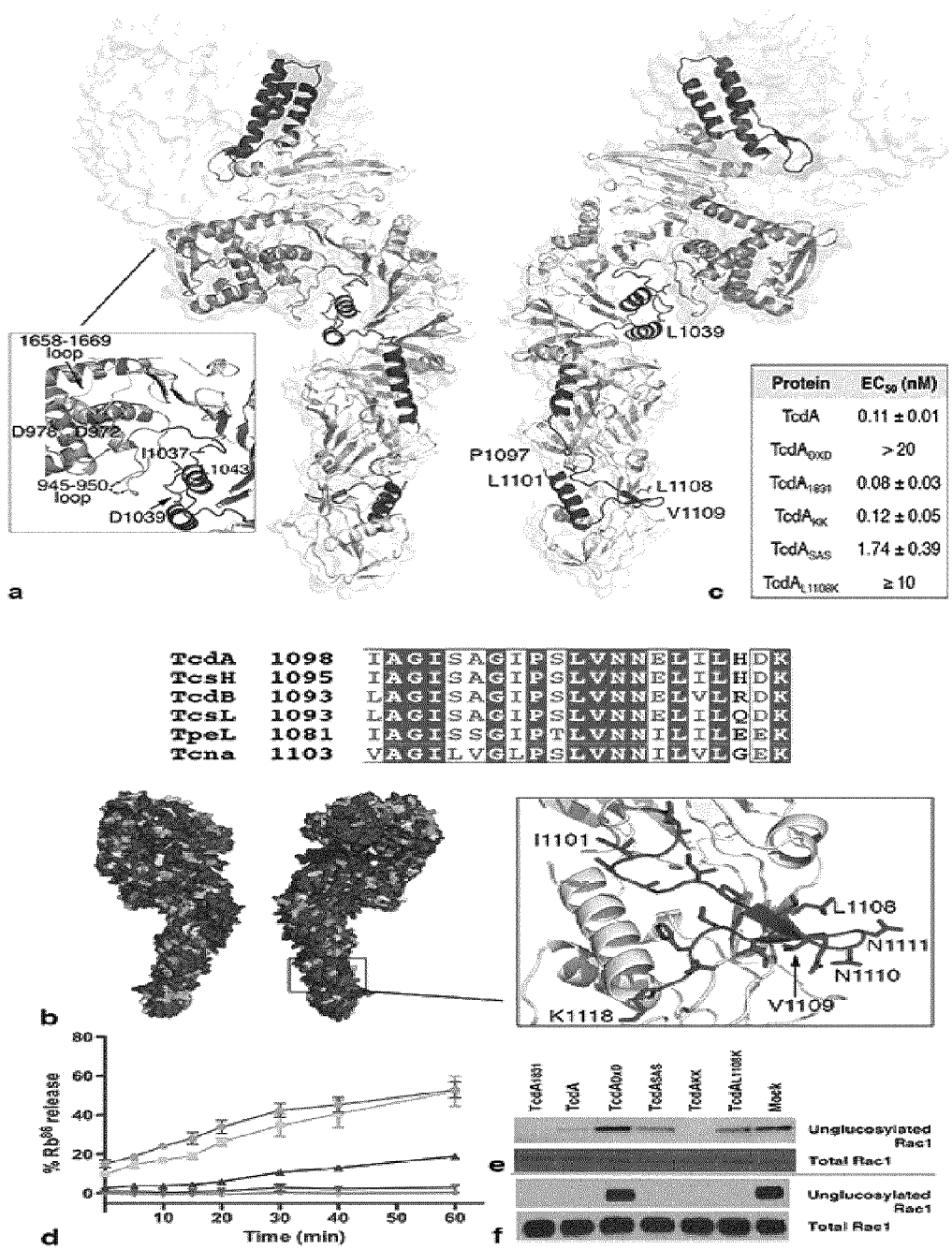
FIG. 11 provides data to illustrate that the delivery domain provides an extended scaffold for an alpha-helical hydrophobic stretch involved in pore formation. Panel (a) depicts most of the TcdA$_{1831}$ crystal structure (residues 1-1025 & 1136-1802) as a transparent surface with the GTD in light shading and the CPD in slightly darker shading. Panel (b) shows an alignment of six representative sequences from large clostridial glycosylating toxins. Panel (c) shows the average EC$_{50}$ and standard deviation calculated from five independent viability assays. Panel (d) shows the results of an evaluation of pore formation on biological membranes. Panel (e) the TcdA$_{SAS}$ and TcdA$_{L1108K}$ proteins are impaired in their capacity to glucosylate Rac1 when applied to the exterior to cells. Panel (f) shows that the TcdA$_{SAS}$ and TcdA$_{L1108K}$ proteins are not impaired in their capacity to glucosylate Rac1 in vitro.

FIG. 11 shows that the delivery domain provides an extended scaffold for an alpha-helical hydrophobic stretch involved in pore formation. In panel (a), it is shown that most of the TcdA$_{1831}$ crystal structure (residues 1-1025 and 1136-1802) is depicted as a transparent surface with the GTD in light shading, initially white, and the CPD in slightly darker shading, initially light blue. The delivery domain is also visible as a cartoon to highlight discrete structural elements: the three-helix bundle (initially shown in blue), the globular sub-domain (initially shown in green), the alpha-helical hydrophobic stretch (residues 1026-1135, initially shown in purple), and the beta-scaffold (initially shown in yellow). The locations of residues that have been implicated in TcdB pore formation were initially depicted in orange or red sticks, now shades of medium grey.

In panel (b), representative sequences are provided from the six large clostridial glucosylating toxins were aligned and scored with a Risler matrix according to the extent of sequence variation. Scores were displayed on the TcdA$_{1831}$ structure surface with a color ramp (initially utilizing red, orange, yellow, green, light blue, and dark blue coloring for differentiation) in which strictly conserved residues were initially colored red, and the most variable residues were initially colored dark blue. The most conserved surface region (boxed) is at the end of the alpha-helical hydrophobic stretch: the 1098-1118 loop and β-hairpin. Within this region, the V1109, N1110, and N1111 residues are notable in their accessibility to solvent.

In panel (c), the average $EC_{50}$ and standard deviation calculated from five independent viability assays. Toxins were applied to CHO cells in duplicate over a range of concentrations (10 fM-20 nM) and incubated for 48 hours at 37° C. Cell viability was quantitated with PrestoBlue by measuring fluorescence and normalizing to cells that had not been exposed to toxin. A representative dose response curve was evaluated. $EC_{50}$'s were calculated in Prism using a four-parameter dose-response curve.

In panel (d), pore formation on biological membranes was evaluated. TcdA, TcdA$_{DXD}$, TcdA$_{KK}$, TcdA$_{SAS}$ and TcdA$_{L1108K}$ were applied to Vero cells preloaded with $^{86}Rb^+$ and then subjected to external medium at pH 4.8. The data represent the averages and standard deviations associated with four experiments for the five proteins. TcdA$_{WT}$, (circles); TcdA$_{DXD}$, (squares); TcdA$_{KK}$, (upward triangles); TcdA$_{SAS}$, (downward triangles); TcdA$_{L1108K}$, (diamonds).

In panel (e), it is shown that the TcdA$_{SAS}$ and TcdA$_{L1108K}$ proteins are impaired in their capacity to glucosylate Rac1 when applied to the exterior to cells. Toxins (10 nM) were applied to HeLa cells and incubated for 3 hours at 37° C. Proteins were separated by SDS-PAGE and probed with antibodies that recognize either non-glucosylated or total quantities of Rac1.

In panel (f), it is shown that the TcdA$_{SAS}$ and TcdA$_{L1108K}$ proteins are not impaired in their capacity to glucosylate Rac1 in vitro. Toxins (100 nM) were mixed with purified GST-Rac1, incubated for 3 hours at 37° C., and analyzed by Western as in panel (e).

Figure 12:
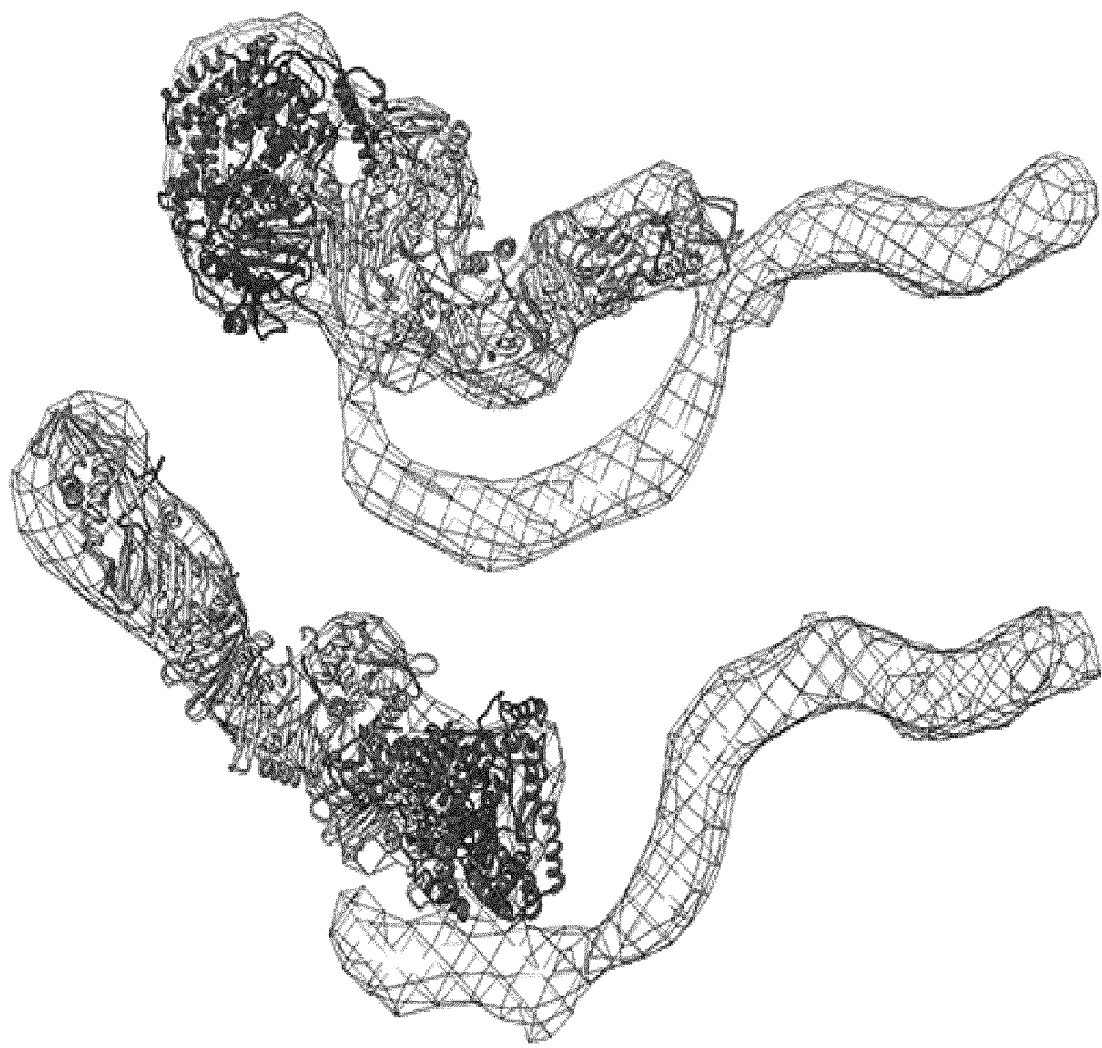
FIG. 12 shows that the TcdA$_{1831}$ structure can rotate about the delivery domain-CROPS junction upon exposure to low pH.

FIG. 12 shows that the TcdA$_{1831}$ structure can rotate about the delivery domain-CROPS junction upon exposure to low pH. The TcdA$_{1831}$ structure was placed in the 20 Å EM structures of TcdA holotoxin at neutral (upper) and acidic (lower) pH. The EM structures were calculated by single particle averaging and random conical tilt as previously described (Pruitt et al., 2010). The crystal structure (initially colored as in FIG. 9) was fit in each map using Chimera.

Discussion

Analysis of TcdA holotoxin by electron microscopy (EM) shows that the C-terminal CROPS (combined repetitive oligopeptides) domain (1832-2710) can serve as an impediment to crystallization. The TcdA construct described herein, encoding residues 1-1831 (FIG. 9, panel a), illustrates that this protein was as active as full-length toxin in cell-based viability and Rac1 glucosylation assays (FIG. 11, panels c and e), consistent with data showing that the CROPS modulates the cytopathic potency of the toxin but is not essential for uptake. The structure of TcdA$_{1831}$ was determined and refined to 3.25 Å resolution. The structure (FIG. 9 panel b) reveals significant interactions between the GTD and CPD and an extended and topologically complex delivery domain.

The GTD aligns to structures of the isolated TcdA GTD in the presence or absence of UDP-glucose with rmsd's of 0.92 and 0.66 Å$^2$, respectively. In the context of TcdA$_{1831}$, the GTD is oriented such that the proposed GTPase binding site is occluded by the presence of the CPD (FIG. 9, panel c). This explains data indicating that glucosyltransferase efficiency is enhanced after the GTD is released by autoprocessing (Pruitt et al., 2012). The C-terminus of the GTD emerges in proximity to the CPD, with residues 538-557 forming an extended loop that spans the CPD active site (FIG. 10, panel a).

Autoprocessing in TcdA and TcdB has previously been ascribed to an InsP6-dependent cysteine protease activity that results in cleavage after L542 (L543 for TcdB) and release of the GTD. Structures of the isolated TcdA and TcdB CPDs have shown that InsP6 binds a positively charged pocket, distal from the active site (Shen et al., 2011). While structures in the absence of InsP6 have heretofore been unavailable, mutational studies in TcdB have revealed an allosteric circuit where InsP6 binding is functionally coupled to the active site through a central 'β-flap' structure (FIG. 10, panel b).

While the N-terminal portion (547-741) of the TcdA$_{1831}$ CPD (crystallized in the absence of InsP6) aligns to the InsP6-bound CPD with an rmsd of 0.67 Å, the C-terminal portion of the domain is significantly different. The β-flap (residues 746-765) separating the InsP6 binding site and the catalytic dyad (C700 and H655) has rotated ~90 degrees, and the sequence that follows (766-802) is significantly repositioned (FIG. 10). One effect of this conformational change is an increase in positively charged residues at the InsP6 binding site. The pocket transitions from four lysine residues in the TcdA$_{1831}$ structure (K602, K649, K754, and K777) to include 7 lysines and 1 arginine in the InsP6 bound structure. The largest change is evident in Lys766 as its NZ atom moves 21 Å as a result of rearrangements in the β-flap. The change also results in a 19 Å movement of H759 out of the active site (comparison of Cβ atoms).

Unexpectedly, anomalous scattering data reveal a zinc atom, bound at H759 and the catalytic dyad of the CPD (FIG. 10). While zinc was not observed in the InsP6-bound structures of the TcdA and TcdB CPDs solved previously, TcdA binds zinc in solution as indicated by both X-ray absorption spectroscopy (XAS) and inductively coupled plasma-mass spectrometry (ICP-MS) experiments. A zinc atom is present at the same site in TcdB as indicated by ICP-MS analysis of TcdB and a TcdB C698A mutant. Zinc is known to act as a negative regulator in cysteine proteases such as papain and has been proposed to protect the active-site sulfhydryl of caspases from oxidative stress. In the toxins, the zinc may also aid in coupling the structural change of InsP6-binding to the positioning of substrate within the active site.

A three-helix bundle (767-841) is located at the GTD-CPD interface and serves as a transition into the delivery domain (FIG. 11, panel a). The three-helix bundle is followed by a small globular sub-domain (850-1025) and then an elongated 'hydrophobic helical stretch' containing four α-helices (1026-1135) that extends to the other end of the molecule. The delivery domain then adopts a series of β-sheet structures as it returns to the base of the CPD. Clear placement of the TcdA$_{1831}$ structure into holotoxin EM structures indicates that the CROPS will extend from the base of the CPD and that exposure to low pH causes a rotation around the CROPS-delivery domain junction (FIG. 12) (Pruitt et al, 2010). A conformational change at the CROPS junction fully exposes the delivery domain and could facilitate pore formation, autoprocessing, and/or GTD delivery across the endosomal membrane.

Primary sequence analysis has revealed the presence of conserved hydrophobic sequences in TcdA (958-1130) and TcdB (956-1128) (von Eichel-Streiber et al., 1992). These sequences have been predicted to insert into the endosomal membrane with acidic pH to form the pore that allows for translocation of the GTD into the cytosol. A combination of site-directed mutagenesis and whole cell rubidium release is used to identify residues required for pore formation in TcdB, as described above in Example 1. One pair of mutants E970K/E976K maps to D972/D978 in the globular sub-domain of the TcdA delivery domain, while another set of mutants align to residues along the 'hydrophobic helical stretch' (FIG. 11, panel a). Among this second set, TcdB$_{L1106K}$ was notable in that it eliminated Rb+ release and cellular toxicity, as outlined above.

To test whether the mutations that confer defects in TcdB pore formation also confer defects in the context of TcdA, equivalent mutations were constructed: TcdA$_{KK}$ (D972K, D978K) and TcdA$_{L1108K}$. While both TcdA mutants were unperturbed in their in vitro glucosyltransfer activity (FIG. 11, panel f), TcdA$_{L1108K}$ was devoid of Rb+ release activity and TcdA$_{KK}$ was impaired relative to wild-type TcdA (FIG. 11, panel d). The impact of the mutations on viability differed significantly, however: relative to wild-type TcdA, the EC$_{50}$ of TcdA$_{KK}$ was unchanged whereas the EC$_{50}$ of TcdA$_{L1108K}$ was increased over 100-fold (FIG. 11, panel c). Similarly, differences were observed in a cell-based Rac1 glucosylation assay: TcdA$_{KK}$ was able to access and glucosylate all of the detectable Rac1 while TcdA$_{L1108K}$ was impaired in this activity.

It was concluded that the pore-forming defect in TcdA$_{KK}$ is modest and that a significant amount of GTD delivery still occurs with this protein. The location of D972 and D978 is in the small globular sub-domain between two loops of the delivery domain, 1658-1669 and 945-950 (a loop that is likely to be flexible since it was not visible in the electron density maps). This suggests a role for the small globular sub-domain in the cellular intoxication mechanism of TcdA. The significant defects in Rb+ release, viability, and cellular Rac1 modification observed with TcdA$_{L1108K}$ support a model in which the hydrophobic helical stretch is involved in pore formation in both TcdA and TcdB.

In addition to the homology with TcdB, TcdA shares homology with large glucosylating toxins from *C. sordellii* (TcsH and TcsL), *C. novyi* (Tcnα), and *C. perfringens* (TpeL). Sequences from these six large clostridial toxins (LCTs) were aligned, and the sequence conservation was mapped onto the TcdA$_{1831}$ structure (FIG. 11, panel b). The largest area of strict conservation that mapped to the surface of the structure was located in a portion of the 'hydrophobic helical stretch': a 1096-1115 loop and β-hairpin. To test the hypothesis that a highly conserved sequence on the surface of the molecule is important for the function of the molecule, we mutated the β-hairpin turn from VNN to SAS. TcdA$_{SAS}$ showed no defect in its in vitro glucosyltransfer activity (FIG. 11, panel f) but was impaired in its capacity to kill cells (FIG. 11, panel c). The impaired toxicity is likely due to a defect in pore formation; TcdA$_{SAS}$ is impaired in a cell-surface Rb+ release assay (FIG. 11, panel d) and its capacity to glucosylate Rac1 in a cell-based intoxication assay (FIG. 11, panel e). The identification of a conserved surface feature with function in toxicity indicates that antibodies specific for this feature can protect against multiple toxin-mediated clostridial infections and indicates that a generalizable strategy can generate safe vaccine antigens for this class of toxins.

Recognizing that hydrophobic helical elements resemble motifs present in the pore-forming domain of diphtheria toxin (DT) (Choe et al., 1992; Wang et al., 2009), the 'double-dagger' model described in Example 1 above, is described. In this model, TcdB inserts two pairs of helical hairpins into the membrane to form a pore. While TcdA and TcdB are homologs and predicted to form similar tertiary structures, DT is different in both size and structure. The pore-forming domain of DT consists of 180 amino acids that form a globular 10-helix bundle with the most hydrophobic sequences shielded within the core of the soluble toxin structure. In contrast, the delivery domains of TcdA and TcdB are 982 amino acids long. Pore formation is but one function established for this domain, and the reason why so much protein is dedicated to this function is not known. The structure of TcdA$_{1831}$ reveals that, rather than shield its hydrophobic sequences within a compact interior, TcdA has stretched its 173 amino acid hydrophobic sequence across the surface of an elongated scaffold of β-sheets. This large delivery domain scaffold can provide an alternative structural solution to maintaining hydrophobic segments that are destined for the membrane in a soluble, but readily accessible conformation. This Example shows a paradigm: that pH-dependent toxins and viruses exist in two distinct environments during their pathogenic lifecycle.

Example 3

Cell Response to TcdA Mutants

Homologous toxins TcdA, TcdA$_{DXD}$, TcdA$_{KK}$, TcdA$_{SAS}$, TcdA$_{L1108K}$, and TcdA$_{KS}$ were applied to cells to observe associated effects. Methods used are as described above in Example 1 and Example 2. The ability of each of mutants and control toxins to release $^{86}$Rubidium ions from Vero cells upon binding to the cell surface and acidification of the medium to trigger insertion into the plasma membrane was tested. Further, mutant toxicity was evaluated by dose response with CHO cells. A double mutant was made prepared for TcdA, having both L1108K, V1109S.

FIG. 13 shows Rb$^{86}$ release, indicative of pore formation on biological membranes. TcdA, TcdA$_{DXD}$, TcdA$_{KK}$, TcdA$_{SAS}$, TcdA$_{L1108K}$, and TcdA$_{KS}$ were applied to Vero cells preloaded with $^{86}$Rb$^+$ and cells were then subjected to external medium at pH 4.8. The data represent the averages and standard deviations associated with four experiments for the 6 proteins. TcdA$_{WT}$, (small circles); TcdA$_{DXD}$, (squares); TcdA$_{KK}$, (upward-pointing triangles); TcdA$_{SAS}$, (downward-pointing triangles); TcdA$_{L1108K}$, (diamonds); TcdA$_{KS}$, (large circles). These data indicate that TcdA $_{WT}$, (small circles); TcdA$_{DXD}$, (squares) steadily increased in percentage Rb$^{86}$ release over a time period of 1 hour, while others toxins showed little release or change over time (with a low but steady increase in release from TcdA$_{KK}$).

FIG. 14 shows a dose response curve for cell viability attributable to the presence of these toxins. TcdA$_{WT}$, (small circles); TcdA$_{DXD}$, (large circles); TcdA$_{1831}$, (upward-pointing triangles); TcdA$_{KK}$, (downward-pointing triangles); TcdA$_{VNN}$, (diamonds); TcdA$_{L1108K}$, (small squares); TcdA$_{KS}$, (large squares). Toxins were applied to CHO cells in duplicate over the indicated concentrations (ranging from 10 fM-20 nM) and incubated for 48 hours at 37° C. Cell viability was quantitated by measuring PrestoBlue fluorescence and normalized to cells that had not been exposed to toxin. TcdA$_{DXD}$ illustrated low toxicity, followed by TcdA$_{L1108K}$, TcdA$_{KS}$ and TcdA$_{VNN}$. Whereas TcdA$_{1831}$ and TcdA$_{KK}$ showed more similarity to the dose response curve of wildtype TcdA.

TcdA$_{DXD}$ was used herein, as described above in Example 2. As expected, TcdADXD showed wild-type ability in its capacity to form pores (FIG. 13) but is not able to kill cells (FIG. 14).

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art without departing from the scope, which is defined solely by the claims appended hereto.

REFERENCES

All references cited herein are incorporated by reference in their entirety.

Choe S, et al. (1992) The crystal structure of diphtheria toxin. Nature 357(6375):216-222.

Chumbler N M, et al. (2012) *Clostridium difficile* Toxin B causes epithelial cell necrosis through an autoprocessing-independent mechanism. PLoS Pathog 8(12):e1003072.

Genisyuerek S, et al. (2011) Structural determinants for membrane insertion, pore formation and translocation of *Clostridium difficile* toxin B. Mol Microbial 79(6):1643-1654.

Hundsberger et al., Eur. J. Biochem. 244 (3), 735-742 (1997).

Kreimeyer I, et al. (2011) Autoproteolytic cleavage mediates cytotoxicity of *Clostridium difficile* toxin A. Naunyn Schmiedebergs Arch Pharmacol 383(3):253-262.

Lanis J M, Barua S, & Ballard J D (2010) Variations in TcdB activity and the hypervirulence of emerging strains of *Clostridium difficile*. PLoS Pathog 6(8):e1001061.

Kabsch, W. Xds. Acta Crystallogr D Biol Crystallogr 66, 125-132, doi:10.1107/S0907444909047337 (2010).

Krogh A, Larsson B, von Heijne G, & Sonnhammer E L (2001) Predicting transmembrane protein topology with a hidden Markov model: application to complete genomes. J Mol Biol 305(3):567-580.

Melnyk R A & Collier R J (2006) A loop network within the anthrax toxin pore positions the phenylalanine clamp in an active conformation. Proc Natl Acad Sci USA 103(26): 9802-9807.

Pruitt, R. N., Chambers, M. G., Ng, K. K., Ohi, M. D. & Lacy, D. B. Structural organization of the functional domains of *Clostridium difficile* toxins A and B. Proc Natl Acad Sci USA 107, 13467-13472, doi:10.1073/pnas.1002199107 (2010).

Pruitt, R. N. et al. Structural determinants of *Clostridium difficile* toxin A glucosyltransferase activity. J Biol Chem 287, 8013-8020, doi:10.1074/jbc.M111.298414 (2012).

Shen, A. et al. Defining an allosteric circuit in the cysteine protease domain of *Clostridium difficile* toxins. Nat Struct Mol Biol 18, 364-371, doi:10.1038/nsmb.1990 (2011).

von Eichel-Streiber C, Laufenberg-Feldmann R, Sartingen S, Schulze J, & Sauerborn M (1992) Comparative sequence analysis of the *Clostridium difficile* toxins A and B. Mol Gen Genet 233(1-2):260-268.

Wang J & London E (2009) The membrane topography of the diphtheria toxin T domain linked to the a chain reveals a transient transmembrane hairpin and potential translocation mechanisms. Biochemistry 48(43):10446-10456.

Yang G, et al. (2008) Expression of recombinant *Clostridium difficile* toxin A and B in *Bacillus megaterium*. BMC Microbiol 8:192.

Zhang Y, et al. (2013) A segment of 97 amino acids within the translocation domain of *Clostridium difficile* toxin B is essential for toxicity. PLoS One 8(3):e58634.

US Patent Publication No. US 2012/0276132 A1.

---

SEQUENCE LISTING

```
<160> NUMBER OF SEQ ID NOS: 17

<210> SEQ ID NO 1
<211> LENGTH: 2372
<212> TYPE: PRT
<213> ORGANISM: Clostridium difficile

<400> SEQUENCE: 1

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190
```

```
Gln Arg Glu Glu Asn Pro Glu Leu Ile Ile Asp Asp Ile Val Lys Thr
            195                 200                 205
Tyr Leu Ser Asn Glu Tyr Ser Lys Glu Ile Asp Glu Leu Asn Thr Tyr
    210                 215                 220
Ile Glu Glu Ser Leu Asn Lys Ile Thr Gln Asn Ser Gly Asn Asp Val
225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ala Ser Asp Ile Leu
            260                 265                 270
Arg Ile Ser Ala Leu Lys Glu Ile Gly Gly Met Tyr Leu Asp Val Asp
        275                 280                 285
Met Leu Pro Gly Ile Gln Pro Asp Leu Phe Glu Ser Ile Glu Lys Pro
    290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
        355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
            420                 425                 430
Asp Ser Ile Met Ala Glu Ala Asn Ala Asp Asn Gly Arg Phe Met Met
        435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
            500                 505                 510
Glu Gln Glu Met Ala Ser Leu Trp Ser Phe Asp Asp Ala Arg Ala Lys
        515                 520                 525
Ala Gln Phe Glu Glu Tyr Lys Arg Asn Tyr Phe Glu Gly Ser Leu Gly
    530                 535                 540
Glu Asp Asp Asn Leu Asp Phe Ser Gln Asn Ile Val Val Asp Lys Glu
545                 550                 555                 560
Tyr Leu Leu Glu Lys Ile Ser Ser Leu Ala Arg Ser Ser Glu Arg Gly
                565                 570                 575
Tyr Ile His Tyr Ile Val Gln Leu Gln Gly Asp Lys Ile Ser Tyr Glu
            580                 585                 590
Ala Ala Cys Asn Leu Phe Ala Lys Thr Pro Tyr Asp Ser Val Leu Phe
        595                 600                 605
```

-continued

```
Gln Lys Asn Ile Glu Asp Ser Glu Ile Ala Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Ser Ile
        755                 760                 765

Ile Lys Asp Ile Ser Ser Lys Glu Tyr Ile Ser Phe Asn Pro Lys Glu
770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Tyr Ala Gln
            980                 985                 990

Leu Phe Ser Thr Gly Leu Asn Thr  Ile Thr Asp Ala Ala  Lys Val Val
        995                 1000                1005

Glu Leu  Val Ser Thr Ala Leu  Asp Glu Thr Ile Asp  Leu Leu Pro
    1010                1015                1020
```

-continued

```
Thr Leu Ser Glu Gly Leu Pro Ile Ile Ala Thr Ile  Ile Asp Gly
    1025            1030                1035

Val Ser Leu Gly Ala Ala Ile Lys Glu Leu Ser Glu  Thr Ser Asp
    1040            1045                1050

Pro Leu Leu Arg Gln Glu Ile Glu Ala Lys Ile Gly  Ile Met Ala
    1055            1060                1065

Val Asn Leu Thr Thr Ala Thr Thr Ala Ile Ile Thr  Ser Ser Leu
    1070            1075                1080

Gly Ile Ala Ser Gly Phe Ser Ile Leu Leu Val Pro  Leu Ala Gly
    1085            1090                1095

Ile Ser Ala Gly Ile Pro Ser Leu Val Asn Asn Glu  Leu Val Leu
    1100            1105                1110

Arg Asp Lys Ala Thr Lys Val Val Asp Tyr Phe Lys  His Val Ser
    1115            1120                1125

Leu Val Glu Thr Glu Gly Val Phe Thr Leu Leu Asp  Asp Lys Ile
    1130            1135                1140

Met Met Pro Gln Asp Asp Leu Val Ile Ser Glu Ile  Asp Phe Asn
    1145            1150                1155

Asn Asn Ser Ile Val Leu Gly Lys Cys Glu Ile Trp  Arg Met Glu
    1160            1165                1170

Gly Gly Ser Gly His Thr Val Thr Asp Asp Ile Asp  His Phe Phe
    1175            1180                1185

Ser Ala Pro Ser Ile Thr Tyr Arg Glu Pro His Leu  Ser Ile Tyr
    1190            1195                1200

Asp Val Leu Glu Val Gln Lys Glu Glu Leu Asp Leu  Ser Lys Asp
    1205            1210                1215

Leu Met Val Leu Pro Asn Ala Pro Asn Arg Val Phe  Ala Trp Glu
    1220            1225                1230

Thr Gly Trp Thr Pro Gly Leu Arg Ser Leu Glu Asn  Asp Gly Thr
    1235            1240                1245

Lys Leu Leu Asp Arg Ile Arg Asp Asn Tyr Glu Gly  Glu Phe Tyr
    1250            1255                1260

Trp Arg Tyr Phe Ala Phe Ile Ala Asp Ala Leu Ile  Thr Thr Leu
    1265            1270                1275

Lys Pro Arg Tyr Glu Asp Thr Asn Ile Arg Ile Asn  Leu Asp Ser
    1280            1285                1290

Asn Thr Arg Ser Phe Ile Val Pro Ile Ile Thr Thr  Glu Tyr Ile
    1295            1300                1305

Arg Glu Lys Leu Ser Tyr Ser Phe Tyr Gly Ser Gly  Gly Thr Tyr
    1310            1315                1320

Ala Leu Ser Leu Ser Gln Tyr Asn Met Gly Ile Asn  Ile Glu Leu
    1325            1330                1335

Ser Glu Ser Asp Val Trp Ile Ile Asp Val Asp Asn  Val Val Arg
    1340            1345                1350

Asp Val Thr Ile Glu Ser Asp Lys Ile Lys Lys Gly  Asp Leu Ile
    1355            1360                1365

Glu Gly Ile Leu Ser Thr Leu Ser Ile Glu Glu Asn  Lys Ile Ile
    1370            1375                1380

Leu Asn Ser His Glu Ile Asn Phe Ser Gly Glu Val  Asn Gly Ser
    1385            1390                1395

Asn Gly Phe Val Ser Leu Thr Phe Ser Ile Leu Glu  Gly Ile Asn
    1400            1405                1410
```

Ala Ile Ile Glu Val Asp Leu Leu Ser Lys Ser Tyr Lys Leu Leu
1415                1420                1425

Ile Ser Gly Glu Leu Lys Ile Leu Met Leu Asn Ser Asn His Ile
1430                1435                1440

Gln Gln Lys Ile Asp Tyr Ile Gly Phe Asn Ser Glu Leu Gln Lys
1445                1450                1455

Asn Ile Pro Tyr Ser Phe Val Asp Ser Glu Gly Lys Glu Asn Gly
1460                1465                1470

Phe Ile Asn Gly Ser Thr Lys Glu Gly Leu Phe Val Ser Glu Leu
1475                1480                1485

Pro Asp Val Val Leu Ile Ser Lys Val Tyr Met Asp Asp Ser Lys
1490                1495                1500

Pro Ser Phe Gly Tyr Tyr Ser Asn Asn Leu Lys Asp Val Lys Val
1505                1510                1515

Ile Thr Lys Asp Asn Val Asn Ile Leu Thr Gly Tyr Tyr Leu Lys
1520                1525                1530

Asp Asp Ile Lys Ile Ser Leu Ser Leu Thr Leu Gln Asp Glu Lys
1535                1540                1545

Thr Ile Lys Leu Asn Ser Val His Leu Asp Glu Ser Gly Val Ala
1550                1555                1560

Glu Ile Leu Lys Phe Met Asn Arg Lys Gly Asn Thr Asn Thr Ser
1565                1570                1575

Asp Ser Leu Met Ser Phe Leu Glu Ser Met Asn Ile Lys Ser Ile
1580                1585                1590

Phe Val Asn Phe Leu Gln Ser Asn Ile Lys Phe Ile Leu Asp Ala
1595                1600                1605

Asn Phe Ile Ile Ser Gly Thr Thr Ser Ile Gly Gln Phe Glu Phe
1610                1615                1620

Ile Cys Asp Glu Asn Asp Asn Ile Gln Pro Tyr Phe Ile Lys Phe
1625                1630                1635

Asn Thr Leu Glu Thr Asn Tyr Thr Leu Tyr Val Gly Asn Arg Gln
1640                1645                1650

Asn Met Ile Val Glu Pro Asn Tyr Asp Leu Asp Asp Ser Gly Asp
1655                1660                1665

Ile Ser Ser Thr Val Ile Asn Phe Ser Gln Lys Tyr Leu Tyr Gly
1670                1675                1680

Ile Asp Ser Cys Val Asn Lys Val Val Ile Ser Pro Asn Ile Tyr
1685                1690                1695

Thr Asp Glu Ile Asn Ile Thr Pro Val Tyr Glu Thr Asn Asn Thr
1700                1705                1710

Tyr Pro Glu Val Ile Val Leu Asp Ala Asn Tyr Ile Asn Glu Lys
1715                1720                1725

Ile Asn Val Asn Ile Asn Asp Leu Ser Ile Arg Tyr Val Trp Ser
1730                1735                1740

Asn Asp Gly Asn Asp Phe Ile Leu Met Ser Thr Ser Glu Glu Asn
1745                1750                1755

Lys Val Ser Gln Val Lys Ile Arg Phe Val Asn Val Phe Lys Asp
1760                1765                1770

Lys Thr Leu Ala Asn Lys Leu Ser Phe Asn Phe Ser Asp Lys Gln
1775                1780                1785

Asp Val Pro Val Ser Glu Ile Ile Leu Ser Phe Thr Pro Ser Tyr
1790                1795                1800

-continued

```
Tyr Glu Asp Gly Leu Ile Gly Tyr Asp Leu Gly Leu Val Ser Leu
1805                1810                1815

Tyr Asn Glu Lys Phe Tyr Ile Asn Asn Phe Gly Met Met Val Ser
1820                1825                1830

Gly Leu Ile Tyr Ile Asn Asp Ser Leu Tyr Tyr Phe Lys Pro Pro
1835                1840                1845

Val Asn Asn Leu Ile Thr Gly Phe Val Thr Val Gly Asp Asp Lys
1850                1855                1860

Tyr Tyr Phe Asn Pro Ile Asn Gly Gly Ala Ala Ser Ile Gly Glu
1865                1870                1875

Thr Ile Ile Asp Asp Lys Asn Tyr Tyr Phe Asn Gln Ser Gly Val
1880                1885                1890

Leu Gln Thr Gly Val Phe Ser Thr Glu Asp Gly Phe Lys Tyr Phe
1895                1900                1905

Ala Pro Ala Asn Thr Leu Asp Glu Asn Leu Glu Gly Glu Ala Ile
1910                1915                1920

Asp Phe Thr Gly Lys Leu Ile Ile Asp Glu Asn Ile Tyr Tyr Phe
1925                1930                1935

Asp Asp Asn Tyr Arg Gly Ala Val Glu Trp Lys Glu Leu Asp Gly
1940                1945                1950

Glu Met His Tyr Phe Ser Pro Glu Thr Gly Lys Ala Phe Lys Gly
1955                1960                1965

Leu Asn Gln Ile Gly Asp Tyr Lys Tyr Tyr Phe Asn Ser Asp Gly
1970                1975                1980

Val Met Gln Lys Gly Phe Val Ser Ile Asn Asp Asn Lys His Tyr
1985                1990                1995

Phe Asp Asp Ser Gly Val Met Lys Val Gly Tyr Thr Glu Ile Asp
2000                2005                2010

Gly Lys His Phe Tyr Phe Ala Glu Asn Gly Glu Met Gln Ile Gly
2015                2020                2025

Val Phe Asn Thr Glu Asp Gly Phe Lys Tyr Phe Ala His His Asn
2030                2035                2040

Glu Asp Leu Gly Asn Glu Glu Gly Glu Glu Ile Ser Tyr Ser Gly
2045                2050                2055

Ile Leu Asn Phe Asn Asn Lys Ile Tyr Tyr Phe Asp Asp Ser Phe
2060                2065                2070

Thr Ala Val Val Gly Trp Lys Asp Leu Glu Asp Gly Ser Lys Tyr
2075                2080                2085

Tyr Phe Asp Glu Asp Thr Ala Glu Ala Tyr Ile Gly Leu Ser Leu
2090                2095                2100

Ile Asn Asp Gly Gln Tyr Tyr Phe Asn Asp Asp Gly Ile Met Gln
2105                2110                2115

Val Gly Phe Val Thr Ile Asn Asp Lys Val Phe Tyr Phe Ser Asp
2120                2125                2130

Ser Gly Ile Ile Glu Ser Gly Val Gln Asn Ile Asp Asp Asn Tyr
2135                2140                2145

Phe Tyr Ile Asp Asp Asn Gly Ile Val Gln Ile Gly Val Phe Asp
2150                2155                2160

Thr Ser Asp Gly Tyr Lys Tyr Phe Ala Pro Ala Asn Thr Val Asn
2165                2170                2175

Asp Asn Ile Tyr Gly Gln Ala Val Glu Tyr Ser Gly Leu Val Arg
2180                2185                2190
```

-continued

Val Gly Glu Asp Val Tyr Tyr Phe Gly Glu Thr Tyr Thr Ile Glu
    2195                2200                2205

Thr Gly Trp Ile Tyr Asp Met Glu Asn Glu Ser Asp Lys Tyr Tyr
    2210                2215                2220

Phe Asn Pro Glu Thr Lys Lys Ala Cys Lys Gly Ile Asn Leu Ile
    2225                2230                2235

Asp Asp Ile Lys Tyr Tyr Phe Asp Glu Lys Gly Ile Met Arg Thr
    2240                2245                2250

Gly Leu Ile Ser Phe Glu Asn Asn Asn Tyr Tyr Phe Asn Glu Asn
    2255                2260                2265

Gly Glu Met Gln Phe Gly Tyr Ile Asn Ile Glu Asp Lys Met Phe
    2270                2275                2280

Tyr Phe Gly Glu Asp Gly Val Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu His His His His His His
    2360                2365                2370

<210> SEQ ID NO 2
<211> LENGTH: 2372
<212> TYPE: PRT
<213> ORGANISM: Clostridium difficile

<400> SEQUENCE: 2

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

```
Gln Arg Glu Glu Asn Pro Glu Leu Ile Ile Asp Asp Ile Val Lys Thr
            195                 200                 205
Tyr Leu Ser Asn Glu Tyr Ser Lys Glu Ile Asp Glu Leu Asn Thr Tyr
210                 215                 220
Ile Glu Glu Ser Leu Asn Lys Ile Thr Gln Asn Ser Gly Asn Asp Val
225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ala Ser Asp Ile Leu
            260                 265                 270
Arg Ile Ser Ala Leu Lys Glu Ile Gly Gly Met Tyr Leu Asp Val Asp
        275                 280                 285
Met Leu Pro Gly Ile Gln Pro Asp Leu Phe Glu Ser Ile Glu Lys Pro
    290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
        355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
            420                 425                 430
Asp Ser Ile Met Ala Glu Ala Asn Ala Asp Asn Gly Arg Phe Met Met
        435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
            500                 505                 510
Glu Gln Glu Met Ala Ser Leu Trp Ser Phe Asp Asp Ala Arg Ala Lys
        515                 520                 525
Ala Gln Phe Glu Glu Tyr Lys Arg Asn Tyr Phe Glu Gly Ser Leu Gly
    530                 535                 540
Glu Asp Asp Asn Leu Asp Phe Ser Gln Asn Ile Val Val Asp Lys Glu
545                 550                 555                 560
Tyr Leu Leu Glu Lys Ile Ser Ser Leu Ala Arg Ser Ser Glu Arg Gly
                565                 570                 575
Tyr Ile His Tyr Ile Val Gln Leu Gln Gly Asp Lys Ile Ser Tyr Glu
            580                 585                 590
Ala Ala Cys Asn Leu Phe Ala Lys Thr Pro Tyr Asp Ser Val Leu Phe
        595                 600                 605
```

```
Gln Lys Asn Ile Glu Asp Ser Glu Ile Ala Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Ser Ile
            755                 760                 765

Ile Lys Asp Ile Ser Ser Lys Glu Tyr Ile Ser Phe Asn Pro Lys Glu
770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
                820                 825                 830

Asp Thr Gln Ile Val Glu Glu Arg Ile Glu Glu Ala Lys Asn Leu Thr
                835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
                900                 905                 910

Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Tyr Ala Gln
                980                 985                 990

Leu Phe Ser Thr Gly Leu Asn Thr Ile Thr Asp Ala Ala Lys Val Val
            995                 1000                1005

Glu Leu Val Ser Thr Ala Leu Asp Glu Thr Ile Asp Leu Leu Pro
    1010                1015                1020
```

```
Thr Leu Ser Glu Gly Leu Pro Ile Ile Ala Thr Ile Ile Asp Gly
    1025            1030                1035

Val Ser Leu Gly Ala Ala Ile Lys Glu Leu Ser Glu Thr Ser Asp
    1040            1045                1050

Pro Leu Leu Arg Gln Glu Ile Glu Ala Lys Ile Gly Ile Met Ala
    1055            1060                1065

Val Asn Leu Thr Thr Ala Thr Thr Ala Ile Ile Thr Ser Ser Leu
    1070            1075                1080

Gly Ile Ala Ser Gly Phe Ser Ile Leu Leu Val Pro Leu Ala Gly
    1085            1090                1095

Ile Ser Ala Gly Ile Pro Ser Lys Val Asn Asn Glu Leu Val Leu
    1100            1105                1110

Arg Asp Lys Ala Thr Lys Val Val Asp Tyr Phe Lys His Val Ser
    1115            1120                1125

Leu Val Glu Thr Glu Gly Val Phe Thr Leu Leu Asp Asp Lys Ile
    1130            1135                1140

Met Met Pro Gln Asp Asp Leu Val Ile Ser Glu Ile Asp Phe Asn
    1145            1150                1155

Asn Asn Ser Ile Val Leu Gly Lys Cys Glu Ile Trp Arg Met Glu
    1160            1165                1170

Gly Gly Ser Gly His Thr Val Thr Asp Asp Ile Asp His Phe Phe
    1175            1180                1185

Ser Ala Pro Ser Ile Thr Tyr Arg Glu Pro His Leu Ser Ile Tyr
    1190            1195                1200

Asp Val Leu Glu Val Gln Lys Glu Glu Leu Asp Leu Ser Lys Asp
    1205            1210                1215

Leu Met Val Leu Pro Asn Ala Pro Asn Arg Val Phe Ala Trp Glu
    1220            1225                1230

Thr Gly Trp Thr Pro Gly Leu Arg Ser Leu Glu Asn Asp Gly Thr
    1235            1240                1245

Lys Leu Leu Asp Arg Ile Arg Asp Asn Tyr Glu Gly Glu Phe Tyr
    1250            1255                1260

Trp Arg Tyr Phe Ala Phe Ile Ala Asp Ala Leu Ile Thr Thr Leu
    1265            1270                1275

Lys Pro Arg Tyr Glu Asp Thr Asn Ile Arg Ile Asn Leu Asp Ser
    1280            1285                1290

Asn Thr Arg Ser Phe Ile Val Pro Ile Ile Thr Thr Glu Tyr Ile
    1295            1300                1305

Arg Glu Lys Leu Ser Tyr Ser Phe Tyr Gly Ser Gly Gly Thr Tyr
    1310            1315                1320

Ala Leu Ser Leu Ser Gln Tyr Asn Met Gly Ile Asn Ile Glu Leu
    1325            1330                1335

Ser Glu Ser Asp Val Trp Ile Ile Asp Val Asp Asn Val Val Arg
    1340            1345                1350

Asp Val Thr Ile Glu Ser Asp Lys Ile Lys Lys Gly Asp Leu Ile
    1355            1360                1365

Glu Gly Ile Leu Ser Thr Leu Ser Ile Glu Glu Asn Lys Ile Ile
    1370            1375                1380

Leu Asn Ser His Glu Ile Asn Phe Ser Gly Glu Val Asn Gly Ser
    1385            1390                1395

Asn Gly Phe Val Ser Leu Thr Phe Ser Ile Leu Glu Gly Ile Asn
    1400            1405                1410
```

```
Ala Ile Ile Glu Val Asp Leu Leu Ser Lys Ser Tyr Lys Leu Leu
    1415                1420                1425

Ile Ser Gly Glu Leu Lys Ile Leu Met Leu Asn Ser Asn His Ile
    1430                1435                1440

Gln Gln Lys Ile Asp Tyr Ile Gly Phe Asn Ser Glu Leu Gln Lys
    1445                1450                1455

Asn Ile Pro Tyr Ser Phe Val Asp Ser Glu Gly Lys Glu Asn Gly
    1460                1465                1470

Phe Ile Asn Gly Ser Thr Lys Glu Gly Leu Phe Val Ser Glu Leu
    1475                1480                1485

Pro Asp Val Val Leu Ile Ser Lys Val Tyr Met Asp Asp Ser Lys
    1490                1495                1500

Pro Ser Phe Gly Tyr Tyr Ser Asn Asn Leu Lys Asp Val Lys Val
    1505                1510                1515

Ile Thr Lys Asp Asn Val Asn Ile Leu Thr Gly Tyr Tyr Leu Lys
    1520                1525                1530

Asp Asp Ile Lys Ile Ser Leu Ser Leu Thr Leu Gln Asp Glu Lys
    1535                1540                1545

Thr Ile Lys Leu Asn Ser Val His Leu Asp Glu Ser Gly Val Ala
    1550                1555                1560

Glu Ile Leu Lys Phe Met Asn Arg Lys Gly Asn Thr Asn Thr Ser
    1565                1570                1575

Asp Ser Leu Met Ser Phe Leu Glu Ser Met Asn Ile Lys Ser Ile
    1580                1585                1590

Phe Val Asn Phe Leu Gln Ser Asn Ile Lys Phe Ile Leu Asp Ala
    1595                1600                1605

Asn Phe Ile Ile Ser Gly Thr Thr Ser Ile Gly Gln Phe Glu Phe
    1610                1615                1620

Ile Cys Asp Glu Asn Asp Asn Ile Gln Pro Tyr Phe Ile Lys Phe
    1625                1630                1635

Asn Thr Leu Glu Thr Asn Tyr Thr Leu Tyr Val Gly Asn Arg Gln
    1640                1645                1650

Asn Met Ile Val Glu Pro Asn Tyr Asp Leu Asp Asp Ser Gly Asp
    1655                1660                1665

Ile Ser Ser Thr Val Ile Asn Phe Ser Gln Lys Tyr Leu Tyr Gly
    1670                1675                1680

Ile Asp Ser Cys Val Asn Lys Val Val Ile Ser Pro Asn Ile Tyr
    1685                1690                1695

Thr Asp Glu Ile Asn Ile Thr Pro Val Tyr Glu Thr Asn Asn Thr
    1700                1705                1710

Tyr Pro Glu Val Ile Val Leu Asp Ala Asn Tyr Ile Asn Glu Lys
    1715                1720                1725

Ile Asn Val Asn Ile Asn Asp Leu Ser Ile Arg Tyr Val Trp Ser
    1730                1735                1740

Asn Asp Gly Asn Asp Phe Ile Leu Met Ser Thr Ser Glu Glu Asn
    1745                1750                1755

Lys Val Ser Gln Val Lys Ile Arg Phe Val Asn Val Phe Lys Asp
    1760                1765                1770

Lys Thr Leu Ala Asn Lys Leu Ser Phe Asn Phe Ser Asp Lys Gln
    1775                1780                1785

Asp Val Pro Val Ser Glu Ile Ile Leu Ser Phe Thr Pro Ser Tyr
    1790                1795                1800
```

```
Tyr Glu  Asp Gly Leu Ile Gly  Tyr Asp Leu Gly  Leu Val Ser Leu
    1805             1810              1815

Tyr Asn  Glu Lys Phe Tyr Ile  Asn Asn Phe Gly  Met Met Val Ser
    1820             1825              1830

Gly Leu  Ile Tyr Ile Asn Asp  Ser Leu Tyr Tyr  Phe Lys Pro Pro
    1835             1840              1845

Val Asn  Asn Leu Ile Thr Gly  Phe Val Thr Gly  Asp Asp Lys
    1850             1855              1860

Tyr Tyr  Phe Asn Pro Ile Asn  Gly Gly Ala Ala  Ser Ile Gly Glu
    1865             1870              1875

Thr Ile  Ile Asp Asp Lys Asn  Tyr Tyr Phe Asn  Gln Ser Gly Val
    1880             1885              1890

Leu Gln  Thr Gly Val Phe Ser  Thr Glu Asp Gly  Phe Lys Tyr Phe
    1895             1900              1905

Ala Pro  Ala Asn Thr Leu Asp  Glu Asn Leu Glu  Gly Glu Ala Ile
    1910             1915              1920

Asp Phe  Thr Gly Lys Leu Ile  Ile Asp Glu Asn  Ile Tyr Tyr Phe
    1925             1930              1935

Asp Asp  Asn Tyr Arg Gly Ala  Val Glu Trp Lys  Glu Leu Asp Gly
    1940             1945              1950

Glu Met  His Tyr Phe Ser Pro  Glu Thr Gly Lys  Ala Phe Lys Gly
    1955             1960              1965

Leu Asn  Gln Ile Gly Asp Tyr  Lys Tyr Tyr Phe  Asn Ser Asp Gly
    1970             1975              1980

Val Met  Gln Lys Gly Phe Val  Ser Ile Asn Asp  Asn Lys His Tyr
    1985             1990              1995

Phe Asp  Asp Ser Gly Val Met  Lys Val Gly Tyr  Thr Glu Ile Asp
    2000             2005              2010

Gly Lys  His Phe Tyr Phe Ala  Glu Asn Gly Glu  Met Gln Ile Gly
    2015             2020              2025

Val Phe  Asn Thr Glu Asp Gly  Phe Lys Tyr Phe  Ala His His Asn
    2030             2035              2040

Glu Asp  Leu Gly Asn Glu Glu  Gly Glu Glu Ile  Ser Tyr Ser Gly
    2045             2050              2055

Ile Leu  Asn Phe Asn Asn Lys  Ile Tyr Tyr Phe  Asp Asp Ser Phe
    2060             2065              2070

Thr Ala  Val Val Gly Trp Lys  Asp Leu Glu Asp  Gly Ser Lys Tyr
    2075             2080              2085

Tyr Phe  Asp Glu Asp Thr Ala  Glu Ala Tyr Ile  Gly Leu Ser Leu
    2090             2095              2100

Ile Asn  Asp Gly Gln Tyr Tyr  Phe Asn Asp Asp  Gly Ile Met Gln
    2105             2110              2115

Val Gly  Phe Val Thr Ile Asn  Asp Lys Val Phe  Tyr Phe Ser Asp
    2120             2125              2130

Ser Gly  Ile Ile Glu Ser Gly  Val Gln Asn Ile  Asp Asp Asn Tyr
    2135             2140              2145

Phe Tyr  Ile Asp Asp Asn Gly  Ile Val Gln Ile  Gly Val Phe Asp
    2150             2155              2160

Thr Ser  Asp Gly Tyr Lys Tyr  Phe Ala Pro Ala  Asn Thr Val Asn
    2165             2170              2175

Asp Asn  Ile Tyr Gly Gln Ala  Val Glu Tyr Ser  Gly Leu Val Arg
    2180             2185              2190
```

| | | | | | | | | | | | |
|---|---|---|---|---|---|---|---|---|---|---|---|
| Val | Gly | Glu | Asp | Val | Tyr | Tyr | Phe | Gly | Glu | Thr | Tyr | Thr | Ile | Glu |
| | 2195 | | | | 2200 | | | | 2205 | | |

Thr Gly Trp Ile Tyr Asp Met Glu Asn Glu Ser Asp Lys Tyr Tyr
    2210                2215                2220

Phe Asn Pro Glu Thr Lys Lys Ala Cys Lys Gly Ile Asn Leu Ile
    2225                2230                2235

Asp Asp Ile Lys Tyr Tyr Phe Asp Glu Lys Gly Ile Met Arg Thr
    2240                2245                2250

Gly Leu Ile Ser Phe Glu Asn Asn Tyr Tyr Phe Asn Glu Asn
    2255                2260                2265

Gly Glu Met Gln Phe Gly Tyr Ile Asn Ile Glu Asp Lys Met Phe
    2270                2275                2280

Tyr Phe Gly Glu Asp Gly Val Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu His His His His His
    2360                2365                2370

<210> SEQ ID NO 3
<211> LENGTH: 7119
<212> TYPE: DNA
<213> ORGANISM: Clostridium difficile

<400> SEQUENCE: 3

```
atgagcctgg tcaaccgtaa acaactggaa aaaatggcaa atgtccgctt tcgcacccaa      60
gaagatgaat atgtcgcaat cctggacgcg ctggaagaat accataacat gagcgaaaat     120
accgtggttg aaaagtacct gaagctgaag gatatcaact ccctgaccga tatttacatc     180
gacacgtata aaaagtcagg ccgtaacaag gcactgaaaa agttcaagga atatctggtg     240
accgaagttc tggaactgaa gaacaataac ctgacgccgg ttgaaaagaa cctgcacttc     300
gtctggattg gcggtcagat caacgatacc gctatcaact acatcaacca atggaaggat     360
gtgaactccg actacaacgt gaacgtgttt tatgattcaa acgcattcct gatcaacacc     420
ctgaaaaaga cggtcgtgga atctgctatc aatgataccc tggaaagttt tcgtgaaaat     480
ctgaacgatc cgcgcttcga ctacaacaag ttttttccgta agcgcatgga aatcatctac     540
gataagcaga gaacttcat caactactac aaggcgcaac gtgaagaaaa tccggaactg     600
attatcgatg acatcgtgaa gacctacctg agcaacgaat actctaagga aatcgatgaa     660
ctgaacaccct acattgaaga atcccctgaac aaaatcacgc agaactcagg caacgatgtt     720
cgcaacttcg aagaattcaa gaacggtgaa agctttaacc tgtatgaaca agaactggtg     780
gaacgttgga acctggcggc cgcatcagat attctgcgca tctcggccct gaaagaaatt     840
ggcggtatgt atctggatgt tgacatgctg ccgggcattc agccggacct gtttgaatct     900
atcgaaaaac cgagctctgt caccgtggat ttctgggaaa tgacgaaact ggaagcgatt     960
atgaaataca ggaatatat ccccggaatat accagtgaac attttgatat gctggacgaa    1020
gaagtgcaga gttccttcga atccgttctg gccagcaagt ccgacaaatc agaaattttt    1080
```

```
agcagcctgg gtgatatgga agcgtcgccg ctggaagtga agattgcctt caacagcaaa      1140
ggtattatca atcagggcct gatctctgtc aaagatagct actgctctaa tctgattgtg      1200
aagcaaatcg aaaaccgtta caagatcctg aacaacagcc tgaatccggc aatttctgaa      1260
gataacgact ttaataccac gaccaacacc ttcattgaca gcatcatggc ggaagccaac      1320
gcagataatg ccgtttttat gatggaactg ggcaagtatc tgcgcgtggg cttttttccg      1380
gatgttaaaa cgaccattaa tctgtctggt ccggaagcat acgctgcagc atatcaggat      1440
ctgctgatgt ttaaagaagg ttcaatgaac attcacctga tcgaagcaga tctgcgcaac      1500
ttcgaaatct cgaaaaccaa tatttcacag tcgacggaac aagaaatggc tagtctgtgg      1560
tcctttgatg acgctcgtgc gaaggcccag ttcgaagaat acaagcgcaa ctacttcgaa      1620
ggcagtctgg gtgaagatga caacctggac ttctcccaaa atattgttgt cgataaggaa      1680
tatctgctgg aaaaaatcag ctctctggcg cgtagttccg aacgcggcta cattcattat      1740
atcgttcagc tgcaaggtga taaaattagc tacgaagcag cttgcaacct gtttgcaaag      1800
accccgtatg actcagtgct gttccagaaa aatatcgaag attcggaaat cgcttactac      1860
tataacccgg gcgacggtga atccaagaaa atcgataagt acaagatccc gtcaatcatc      1920
tcggatcgtc cgaaaatcaa gctgaccttt attggccacg gtaaagatga attcaatacg      1980 gacattttg cgggcttcga tgtggacagc ctgtctaccg aaattgaagc ggccatcgat      2040
ctggccaagg aagacattag cccgaaatct attgaaatca atctgctggg ctgtaacatg      2100
tttagttact ccatcaacgt ggaagaaacc tatccgggta aactgctgct gaaagttaag      2160
gacaaaattt cagaactgat gccgtcaatc tcgcaggata gtattatcgt ctccgccaac      2220
caatatgaag tgcgcattaa ttctgaaggc cgtcgcgaac tgctggatca ttcgggtgaa      2280
tggatcaaca aagaagaaag catcatcaag gatatctcat cgaaggaata catcagcttc      2340
aacccgaagg aaaacaagat caccgtgaag tccaagaacc tgccggaact gtcaacgctg      2400
ctgcaggaaa tccgtaataa cagtaacagc tctgatattg aactggaaga aaaagtgatg      2460
ctgaccgaat gcgaaattaa cgttatctcc aatattgata cgcagatcgt cgaagaacgc      2520
attgaagaag cgaaaaacct gaccagcgac tctattaact acatcaagga tgaattcaag      2580
ctgatcgaaa gtatttccga tgccctgtgt gacctgaaac agcaaaacga actggaagat      2640 tcacactta tctcgttcga agatatttcg gaaaccgacg aaggctttag catccgcttc      2700
atcaacaagg aaacgggtga atcaatcttc gtggaaacgg aaaaaaccat cttctcggaa      2760
tatgcgaacc atattaccga agaaatcagc aagattaaag gcaccatttt tgacacggtt      2820
aatggtaaac tggtcaaaaa ggtgaacctg gatacgaccc acgaagtcaa caccctgaat      2880
gcagcgtttt tcattcagag cctgatcgaa tacaatagtt ccaaggaatc actgtcgaac      2940
ctgtcggttg caatgaaagt tcaggtctat gctcaactgt ttagcaccgg cctgaatacg      3000
attaccgatg cggccaaagt ggttgaactg gtgtctaccg cgctggatga aacgatcgac      3060
ctgctgccga ccctgagtga aggtctgccg attatcgcca cgattatcga tggcgtttcc      3120
ctgggtgcag ctattaaaga actgagtgaa acctccgatc cgctgctgcg tcaggaaatc      3180
gaagcaaaaa ttggcatcat ggctgttaac ctgacgaccg caacgaccgc tattatcacg      3240
tcatcgctgg gcatcgcatc aggttttttcg attctgctgg tgccgctggc aggtattagt      3300
gcaggtatcc cgtccctggt taataacgaa ctggtcctgc gcgacaaggc taccaaagtc      3360
gtggattatt ttaaacatgt tagcctggtc gaaaccgagg gtgtgttcac gctgctggat      3420
gacaaaatta tgatgccgca ggatgacctg gtcatctcgg aaatcgattt caacaacaac      3480
```

```
agcattgtgc tgggcaaatg tgaaatctgg cgtatggaag gcggtagcgg tcatacggtt    3540
accgatgaca tcgatcactt tttcagcgcg ccgtctatta cctaccgcga accgcacctg    3600
agcatctatg atgtgctgga agttcagaag gaagaactgg atctgtctaa agacctgatg    3660
gtcctgccga acgcgccgaa tcgtgtgttt gcctgggaaa cgggttggac cccgggtctg    3720
cgtagcctgg aaaatgatgg caccaaactg ctggatcgta ttcgcgacaa ctacgagggt    3780
gaattctact ggcgttattt tgccttcatc gcagatgctc tgattacgac cctgaaaccg    3840
cgttatgaag acaccaacat tcgcatcaat ctggatagca acacgcgttc tttattgtg     3900
ccgattatca cgaccgaata tatccgcgaa aaactgagct actctttcta tggcagcggc    3960
ggtacctacg cactgagtct gtcccagtat aatatgggta ttaacatcga actgtcagaa    4020
tcggatgtgt ggattatcga tgttgacaat gttgtccgcg atgttaccat cgaaagcgac    4080
aaaattaaaa agggtgatct gatcgaaggc attctgagta cgctgtccat cgaagaaaac    4140
aagatcatcc tgaacagtca tgaaatcaat tttagcggcg aagttaacgg ctcaaatggt    4200
tttgtcagtc tgaccttctc cattctggaa ggtatcaacg ccattatcga agtggatctg    4260
ctgagcaagt cttataaact gctgatcagc ggcgaactga agattctgat gctgaattct    4320
aaccacatcc agcaaaagat cgattacatc ggtttcaaca gcgaactgca gaagaatatc    4380
ccgtactcat tcgttgattc ggaaggcaag gaaaatggtt tcatcaacgg ctctaccaaa    4440
gaaggcctgt tgttagtga actgccggat gtggttctga ttagtaaggt ctatatggat    4500
gactcaaaac cgtcgtttgg ctactattcc aacaatctga aggacgtgaa ggttatcacc    4560
aaggataacg tgaacatcct gacgggttac tatctgaagg atgacattaa atcagtctg     4620
tccctgaccc tgcaggacga aaagacgatt aaactgaatt cggtgcatct ggatgaaagc    4680
ggcgttgcag aaatcctgaa gtttatgaac cgtaaaggta atacgaacac ctcagattcg    4740
ctgatgagct tcctggaatc tatgaacatc aagtccatct tcgttaactt cctgcagtca    4800
aatatcaagt ttattctgga tgcgaacttc attatcagtg gtacgacctc catcggccag    4860
tttgaattca tttgcgatga aaatgacaac atccaaccgt actttattaa attcaacacg    4920
ctggaaacca attacacgct gtatgttggt aaccgccaga atatgattgt cgaaccgaat    4980
tatgacctgg atgactctgg cgatatcagc tctaccgtca ttaactttag tcaaaagtac    5040
ctgtatggta ttgattcgtg tgtgaacaaa gtcgtgatta gcccgaatat ctataccgat    5100
gaaattaaca tcacgccggt gtacgaaacc aacaatacgt atccggaagt cattgtgctg    5160
gacgcgaact acatcaacga aaagatcaac gttaacatca cgatctgtc tatccgttat    5220
gtctggagta acgatggcaa tgactttatc ctgatgagca cctctgaaga aaataaagtc    5280
agccaggtga aaattcgctt tgttaacgtc ttcaaggata aaacgctggc caacaagctg    5340
tcatttaatt tctcggataa acaagacgtg cctgttagtg aaattatcct gagctttacc    5400
ccgtcttact atgaagacgg cctgattggt tacgatctgg gtctggtttc cctgtacaac    5460
gaaaagttct acatcaacaa cttcggtatg atggtgtctg gcctgatcta catcaacgat    5520
agtctgtact acttcaaacc gccggtgaac aatctgatta ccggtttcgt cacggtgggc    5580
gatgacaagt actacttcaa cccgatcaac ggcggtgcgg ccagcatcgg cgaaaccatc    5640
atcgatgaca agaactacta cttcaaccag tctggtgtcc tgcaaaccgg cgtgttcagt    5700
acggaagacg gttttaaata tttcgcgccg gccaacaccc tggatgaaaa tctggaaggc    5760
gaagcgattg actttacggg caagctgatc atcgatgaaa acatctacta cttcgatgac    5820
aactaccgtg gcgcagtgga atggaaagaa ctggatggtg aaatgcatta ttttagcccg    5880
```

-continued

```
gaaaccggca aggctttcaa aggcctgaat cagattggtg actacaaata ctatttcaac    5940
agtgatggcg tcatgcaaaa gggtttcgtg tccatcaacg ataacaagca ttatttcgat    6000
gacagcggcg ttatgaaggt cggttacacc gaaattgatg gcaaacactt ttatttcgcg    6060
gaaaatggcg aaatgcagat cggtgttttt aacaccgaag atggttttaa atacttcgcc    6120
catcacaacg aagatctggg taatgaagaa ggcgaagaaa tcagttattc cggcattctg    6180
aacttcaaca acaagattta ttacttcgat gactcattca ccgccgttgt cggctggaag    6240
gatctggaag acggttcgaa atactatttc gatgaagaca cggcagaagc ttatatcggc    6300
ctgagtctga tcaacgatgg ccagtactac ttcaacgatg acggcatcat gcaagtgggt    6360
ttcgttacca tcaacgacaa ggtgttttat ttctcagatt cgggcattat cgaatctggt    6420
gttcagaaca tcgatgacaa ctacttctac atcgatgaca atggcatcgt ccaaattggt    6480
gtgtttgata ccagcgacgg ctacaagtac ttcgcgccgg ccaacacggt gaacgataat    6540
atttacggtc aggccgttga atattctggc ctggttcgtg tcggtgaaga tgtgtactat    6600
tttggcgaaa cgtacaccat cgaaaccggt tggatctacg acatggaaaa cgaaagcgat    6660
aaatattact caacccggga acgaaaaag gcatgcaagg gtatcaatct gattgatgac    6720
atcaagtact atttcgatga aaaggcatc atgcgcaccg tctgatctc tttcgaaaac    6780
aacaactact acttcaacga aacggtgaa atgcagtttg ttacatcaa catcgaagac    6840
aagatgttct atttcggcga agatggtgtt atgcagattg gcgtctttaa cacccggac    6900
ggttttaaat acttcgcgca tcaaaacacg ctggatgaaa acttcgaagg cgaaagtatc    6960
aactacaccg gttggctgga tctggacgaa aaacgctact attttaccga cgaatacatt    7020
gcagctacgg gcagcgtgat tatcgatggt gaagaatatt attttgaccc ggacaccgca    7080
caactggtta tttctgaaca tcatcatcat catcactaa                          7119
```

<210> SEQ ID NO 4
<211> LENGTH: 7119
<212> TYPE: DNA
<213> ORGANISM: Clostridium difficile

<400> SEQUENCE: 4

```
atgagcctgg tcaaccgtaa acaactggaa aaaatggcaa atgtccgctt cgcacccaa     60
gaagatgaat atgtcgcaat cctggacgcg ctggaagaat accataacat gagcgaaaat    120
accgtggttg aaaagtacct gaagctgaag gatatcaact ccctgaccga tatttacatc    180
gacacgtata aaaagtcagg ccgtaacaag gcactgaaaa agttcaagga atatctggtg    240
accgaagttc tggaactgaa gaacaataac ctgacgccgg ttgaaaagaa cctgcacttc    300
gtctggattg gcggtcagat caacgatacc gctatcaact acatcaacca atggaaggat    360
gtgaactccg actacaacgt gaacgtgttt tatgattcaa acgcattcct gatcaacacc    420
ctgaaaaaga cggtcgtgga atctgctatc aatgataccc tggaaagttt tcgtgaaaat    480
ctgaacgatc cgcgcttcga ctacaacaag ttttttccgta agcgcatgga aatcatctac    540
gataagcaga agaacttcat caactactac aaggcgcaac gtgaagaaaa tccggaactg    600
attatcgatg acatcgtgaa gacctacctg agcaacgaat actctaagga aatcgatgaa    660
ctgaacaccct acattgaaga tccctgaac aaaatcacgc agaactcagg caacgatgtt    720
cgcaacttcg aagaattcaa gaacggtgaa agctttaacc tgtatgaaca agaactggtg    780
gaacgttgga acctggcggc cgcatcagat attctgcgca tctcggccct gaaagaaatt    840
ggcggtatgt atctggatgt tgacatgctg ccgggcattc agccggacct gtttgaatct    900
```

| | |
|---|---|
| atcgaaaaac cgagctctgt caccgtggat ttctgggaaa tgacgaaact ggaagcgatt | 960 |
| atgaaataca aggaatatat cccggaatat accagtgaac attttgatat gctggacgaa | 1020 |
| gaagtgcaga gttccttcga atccgttctg ccagcaagt ccgacaaatc agaaattttt | 1080 |
| agcagcctgg gtgatatgga agcgtcgccg ctggaagtga agattgcctt caacagcaaa | 1140 |
| ggtattatca atcagggcct gatctctgtc aaagatagct actgctctaa tctgattgtg | 1200 |
| aagcaaatcg aaaaccgtta caagatcctg aacaacagcc tgaatccggc aatttctgaa | 1260 |
| gataacgact ttaataccac gaccaacacc ttcattgaca gcatcatggc ggaagccaac | 1320 |
| gcagataatg gccgttttat gatggaactg ggcaagtatc tgcgcgtggg cttttttccg | 1380 |
| gatgttaaaa cgaccattaa tctgtctggt ccggaagcat acgctgcagc atatcaggat | 1440 |
| ctgctgatgt ttaaagaagg ttcaatgaac attcacctga tcgaagcaga tctgcgcaac | 1500 |
| ttcgaaatct cgaaaaccaa tatttcacag tcgacggaac aagaaatggc tagtctgtgg | 1560 |
| tcctttgatg acgctcgtgc gaaggccag ttcgaagaat acaagcgcaa ctacttcgaa | 1620 |
| ggcagtctgg gtgaagatga caacctgac ttctcccaaa atattgttgt cgataaggaa | 1680 |
| tatctgctgg aaaaaatcag ctctctggcg cgtagttccg aacgcggcta cattcattat | 1740 |
| atcgttcagc tgcaaggtga taaaattagc tacgaagcag cttgcaacct gtttgcaaag | 1800 |
| accccgtatg actcagtgct gttccagaaa aatatcgaag attcggaaat cgcttactac | 1860 |
| tataacccgg cgacggtga atccaagaa atcgataagt acaagatccc gtcaatcatc | 1920 |
| tcggatcgtc cgaaaatcaa gctgaccttt attggccacg gtaaagatga attcaatacg | 1980 |
| gacatttttg cgggcttcga tgtggacagc ctgtctaccg aaattgaagc ggccatcgat | 2040 |
| ctggccaagg aagacattag cccgaaatct attgaaatca atctgctggg ctgtaacatg | 2100 |
| tttagttact ccatcaacgt ggaagaaacc tatccgggta actgctgct gaaagttaag | 2160 |
| gacaaaattt cagaactgat gccgtcaatc tcgcaggata gtattatcgt ctccgccaac | 2220 |
| caatatgaag tgcgcattaa ttctgaaggc cgtcgcgaac tgctggatca ttcgggtgaa | 2280 |
| tggatcaaca agaagaaag catcatcaag gatatctcat cgaaggaata catcagcttc | 2340 |
| aacccgaagg aaaacaagat caccgtgaag tccaagaacc tgccggaact gtcaacgctg | 2400 |
| ctgcaggaaa tccgtaataa cagtaacagc tctgatattg aactggaaga aaaagtgatg | 2460 |
| ctgaccgaat gcgaaattaa cgttatctcc aatattgata cgcagatcgt cgaagaacgc | 2520 |
| attgaagaag cgaaaaacct gaccagcgac tctattaact acatcaagga tgaattcaag | 2580 |
| ctgatcgaaa gtatttccga tgccctgtgt gacctgaaac agcaaaacga actggaagat | 2640 |
| tcacacttta tctcgttcga agatatttcg gaaaccgacg aaggctttag catccgcttc | 2700 |
| atcaacaagg aaacgggtga atcaatcttc gtggaaacgg aaaaaaccat cttctcggaa | 2760 |
| tatgcgaacc atattaccga agaaatcagc aagattaaag gcaccatttt tgacacggtt | 2820 |
| aatggtaaac tggtcaaaaa ggtgaacctg atacgaccc acgaagtcaa caccctgaat | 2880 |
| gcagcgtttt tcattcagag cctgatcgaa tacaatagtt ccaaggaatc actgtcgaac | 2940 |
| ctgtcggttg caatgaaagt tcaggtctat gctcaactgt ttagcaccgg cctgaatacg | 3000 |
| attaccgatg cggccaaagt ggttgaactg gtgtctaccg cgctggatga acgatcgac | 3060 |
| ctgctgccga ccctgagtga aggtctgccg attatcgcca cgattatcga tggcgtttcc | 3120 |
| ctgggtgcag ctattaaaga actgagtgaa acctccgatc cgctgctgcg tcaggaaatc | 3180 |
| gaagcaaaaa ttggcatcat ggctgttaac ctgacgaccg caacgaccgc tattatcacg | 3240 |
| tcatcgctgg gcatcgcatc aggttttttcg attctgctgg tgccgctggc aggtattagt | 3300 |

```
gcaggtatcc cgtccaaggt taataacgaa ctggtcctgc gcgacaaggc taccaaagtc    3360
gtggattatt ttaaacatgt tagcctggtc gaaaccgagg gtgtgttcac gctgctggat    3420
gacaaaatta tgatgccgca ggatgacctg gtcatctcgg aaatcgattt caacaacaac    3480
agcattgtgc tgggcaaatg tgaaatctgg cgtatggaag gcggtagcgg tcatacggtt    3540
accgatgaca tcgatcactt tttcagcgcg ccgtctatta cctaccgcga accgcacctg    3600
agcatctatg atgtgctgga agttcagaag gaagaactgg atctgtctaa agacctgatg    3660
gtcctgccga acgcgccgaa tcgtgtgttt gcctgggaaa cgggttggac cccgggtctg    3720
cgtagcctgg aaaatgatgg caccaaactg ctggatcgta ttcgcgacaa ctacgagggt    3780
gaattctact ggcgttattt tgccttcatc gcagatgctc tgattacgac cctgaaaccg    3840
cgttatgaag acaccaacat tcgcatcaat ctggatagca cacgcgttc ttttattgtg    3900 ccgattatca cgaccgaata tatccgcgaa aaactgagct actctttcta tggcagcggc    3960
ggtacctacg cactgagtct gtcccagtat aatatgggta ttaacatcga actgtcagaa    4020
tcggatgtgt ggattatcga tgttgacaat gttgccgcg atgttaccat cgaaagcgac    4080
aaaattaaaa agggtgatct gatcgaaggc attctgagta cgctgtccat cgaagaaaac    4140
aagatcatcc tgaacagtca tgaaatcaat tttagcggcg aagttaacgg ctcaaatggt    4200
tttgtcagtc tgaccttctc cattctggaa ggtatcaacg ccattatcga agtggatctg    4260
ctgagcaagt cttataaact gctgatcagc ggcgaactga agattctgat gctgaattct    4320
aaccacatcc agcaaaagat cgattacatc ggtttcaaca gcgaactgca agaatatc    4380 ccgtactcat tcgttgattc ggaaggcaag gaaaatggtt tcatcaacgg ctctaccaaa    4440
gaaggcctgt ttgttagtga actgccggat gtggttctga ttagtaaggt ctatatggat    4500
gactcaaaac cgtcgtttgg ctactattcc aacaatctga aggacgtgaa ggttatcacc    4560
aaggataacg tgaacatcct gacgggttac tatctgaagg atgacattaa aatcagtctg    4620
tccctgaccc tgcaggacga aaagacgatt aaactgaatt cggtgcatct ggatgaaagc    4680
ggcgttgcag aaatcctgaa gtttatgaac cgtaaaggta atacgaacac ctcagattcg    4740
ctgatgagct tcctggaatc tatgaacatc aagtccatct tcgttaactt cctgcagtca    4800
aatatcaagt ttattctgga tgcgaacttc attatcagtg gtacgacctc catcggccag    4860
tttgaattca tttgcgatga aaatgacaac atccaaccgt actttattaa attcaacacg    4920
ctggaaacca attacacgct gtatgttggt aaccgccaga atatgattgt cgaaccgaat    4980
tatgacctgg atgactctgg cgatatcagc tctaccgtca ttaactttag tcaaaagtac    5040
ctgtatggta ttgattcgtg tgtgaacaaa tcgtgatta gcccgaatat ctataccgat    5100
gaaattaaca tcacgccggt gtacgaaacc aacaatacgt atccggaagt cattgtgctg    5160
gacgcgaact acatcaacga aaagatcaac gttaacatca cgatctgtc tatccgttat    5220 gtctggagta acgatggcaa tgactttatc ctgatgagca cctctgaaga aaataaagtc    5280
agccaggtga aaattcgctt tgttaacgtc ttcaaggata aaacgctggc caacaagctg    5340
tcatttaatt tctcggataa acaagacgtg cctgttagtg aaattatcct gagctttacc    5400
ccgtcttact atgaagacgg cctgattggt tacgatctgg gtctggtttc cctgtacaac    5460
gaaaagttct acatcaacaa cttcggtatg atggtgtctg gcctgatcta catcaacgat    5520
agtctgtact acttcaaacc gccggtgaac aatctgatta ccggttttcgt cacggtgggc    5580 gatgacaagt actacttcaa cccgatcaac ggcggtgcgg ccagcatcgg cgaaaccatc    5640
```

```
atcgatgaca agaactacta cttcaaccag tctggtgtcc tgcaaaccgg cgtgttcagt   5700
acggaagacg gttttaaata tttcgcgccg gccaacaccc tggatgaaaa tctggaaggc   5760
gaagcgattg actttacggg caagctgatc atcgatgaaa acatctacta cttcgatgac   5820
aactaccgtg cgcagtggaa atggaaagaa ctggatggtg aaatgcatta ttttagcccg   5880
gaaaccggca aggctttcaa aggcctgaat cagattggtg actacaaata ctatttcaac   5940
agtgatggcg tcatgcaaaa gggtttcgtg tccatcaacg ataacaagca ttatttcgat   6000
gacagcggcg ttatgaaggt cggttacacc gaaattgatg gcaaacactt ttatttcgcg   6060
gaaaatggcg aaatgcagat cggtgttttt aacaccgaag atggttttaa atacttcgcc   6120
catcacaacg aagatctggg taatgaagaa ggcgaagaaa tcagttattc cggcattctg   6180
aacttcaaca acaagattta ttacttcgat gactcattca ccgccgttgt cggctggaag   6240
gatctggaag acggttcgaa atactatttc gatgaagaca cggcagaagc ttatatcggc   6300
ctgagtctga tcaacgatgg ccagtactac ttcaacgatg acggcatcat gcaagtgggt   6360
ttcgttacca tcaacgacaa ggtgttttat ttctcagatt cggcattat cgaatctggt   6420 gttcagaaca tcgatgacaa ctacttctac atcgatgaca atggcatcgt ccaaattggt   6480
gtgtttgata ccagcgacgg ctacaagtac ttcgcgccgg ccaacacggt gaacgataat   6540
atttacggtc aggccgttga atattctggc ctggttcgtg tcggtgaaga tgtgtactat   6600
tttggcgaaa cgtacaccat cgaaaccggt tggatctacg acatggaaaa cgaaagcgat   6660
aaatattact tcaacccgga aacgaaaaag gcatgcaagg gtatcaatct gattgatgac   6720
atcaagtact atttcgatga aaaggcatc atgcgcaccg gtctgatctc tttcgaaaac   6780
aacaactact acttcaacga aacggtgaaa tgcagtttg gttacatcaa catcgaagac   6840
aagatgttct atttcggcga agatggtgtt atgcagattg gcgtctttaa caccccggac   6900
ggttttaaat acttcgcgca tcaaaacacg ctggatgaaa acttcgaagg cgaaagtatc   6960
aactacaccg gttggctgga tctggacgaa aaacgctact attttaccga cgaatacatt   7020
gcagctacgg gcagcgtgat tatcgatggt gaagaatatt attttgaccc ggacaccgca   7080
caactggtta tttctgaaca tcatcatcat catcactaa                          7119
```

<210> SEQ ID NO 5
<211> LENGTH: 16
<212> TYPE: PRT
<213> ORGANISM: Clostridium difficile

<400> SEQUENCE: 5

Ile Ile Ala Thr Ile Ile Asp Gly Val Ser Leu Gly Ala Ala Ile Lys
1               5                   10                  15

<210> SEQ ID NO 6
<211> LENGTH: 15
<212> TYPE: PRT
<213> ORGANISM: Clostridium difficile

<400> SEQUENCE: 6

Val Pro Leu Ala Gly Ile Ser Ala Gly Ile Pro Ser Leu Val Asn
1               5                   10                  15

<210> SEQ ID NO 7
<211> LENGTH: 16
<212> TYPE: PRT
<213> ORGANISM: Clostridium difficile

```
<400> SEQUENCE: 7

Ile Val Ser Thr Ile Leu Asp Gly Ile Asn Leu Gly Ala Ala Ile Lys
1               5                   10                  15

<210> SEQ ID NO 8
<211> LENGTH: 15
<212> TYPE: PRT
<213> ORGANISM: Clostridium difficile

<400> SEQUENCE: 8

Leu Pro Ile Ala Gly Ile Ser Ala Gly Ile Pro Ser Leu Val Asn
1               5                   10                  15

<210> SEQ ID NO 9
<211> LENGTH: 16
<212> TYPE: PRT
<213> ORGANISM: Corynebacterium diphtheriae

<400> SEQUENCE: 9

Asn Val Ala Gln Val Ile Asp Ser Glu Thr Ala Asp Asn Leu Glu Lys
1               5                   10                  15

<210> SEQ ID NO 10
<211> LENGTH: 15
<212> TYPE: PRT
<213> ORGANISM: Corynebacterium diphtheriae
<220> FEATURE:
<221> NAME/KEY: MISC_FEATURE
<222> LOCATION: (6)..(11)
<223> OTHER INFORMATION: Xaa is any amino acid

<400> SEQUENCE: 10

Ile Pro Leu Val Gly Xaa Xaa Xaa Xaa Xaa Xaa Glu Leu Val Asp
1               5                   10                  15

<210> SEQ ID NO 11
<211> LENGTH: 15
<212> TYPE: PRT
<213> ORGANISM: Clostridium difficile

<400> SEQUENCE: 11

Ala Gly Ile Ser Ala Gly Ile Pro Ser Leu Val Asn Asn Glu Leu
1               5                   10                  15

<210> SEQ ID NO 12
<211> LENGTH: 20
<212> TYPE: PRT
<213> ORGANISM: Clostridium difficile

<400> SEQUENCE: 12

Val Pro Leu Ala Gly Ile Ser Ala Gly Ile Pro Ser Leu Val Asn Asn
1               5                   10                  15

Glu Leu Val Leu
            20

<210> SEQ ID NO 13
<211> LENGTH: 20
<212> TYPE: PRT
<213> ORGANISM: Clostridium difficile
```

```
<400> SEQUENCE: 13

Leu Pro Ile Ala Gly Ile Ser Ala Gly Ile Pro Ser Leu Val Asn Asn
1               5                   10                  15

Glu Leu Ile Leu
            20

<210> SEQ ID NO 14
<211> LENGTH: 20
<212> TYPE: PRT
<213> ORGANISM: Clostridium difficile

<400> SEQUENCE: 14

Val Pro Leu Ala Gly Ile Ser Ala Gly Ile Pro Ser Lys Val Asn Asn
1               5                   10                  15

Glu Leu Val Leu
            20

<210> SEQ ID NO 15
<211> LENGTH: 20
<212> TYPE: PRT
<213> ORGANISM: Clostridium difficile

<400> SEQUENCE: 15

Leu Pro Ile Ala Gly Ile Ser Ala Gly Ile Pro Ser Lys Val Asn Asn
1               5                   10                  15

Glu Leu Ile Leu
            20

<210> SEQ ID NO 16
<211> LENGTH: 20
<212> TYPE: PRT
<213> ORGANISM: Clostridium difficile

<400> SEQUENCE: 16

Val Pro Leu Ala Gly Ile Ser Ala Gly Ile Pro Ser Lys Ser Ala Ser
1               5                   10                  15

Glu Leu Val Leu
            20

<210> SEQ ID NO 17
<211> LENGTH: 20
<212> TYPE: PRT
<213> ORGANISM: Clostridium difficile

<400> SEQUENCE: 17

Leu Pro Ile Ala Gly Ile Ser Ala Gly Ile Pro Ser Lys Ser Ala Ser
1               5                   10                  15

Glu Leu Ile Leu
            20
```

The invention claimed is:

1. A recombinant *Clostridium* toxin protein comprising a mutant of SEQ ID NO: 11 (AGISAGIPSLVNNEL), wherein the mutant comprises 1 to 4 mutations in LVNN of SEQ ID NO: 11.

2. The recombinant protein of claim 1, wherein the mutation is L to K.

3. The recombinant protein of claim 1, wherein the mutation is VNN to SAS.

4. The recombinant protein of claim 1, wherein the mutant of SEQ ID NO: 11 comprises a mutant of SEQ ID NO: 12 (VPLAGISAGIPSLVNNELVL) or SEQ ID NO: 13 (LPIAGISAGIPSLVNNELIL).

5. The recombinant protein of claim 4, wherein the mutant of SEQ ID NO:12 or SEQ ID NO: 13 comprises:
SEQ ID NO: 14 (VPLAGISAGIPSKVNNELVL);
SEQ ID NO: 15 (LPIAGISAGIPSKVNNELIL);
SEQ ID NO: 16 (VPLAGISAGIPSKSASELVL); or
SEQ ID NO: 17 (LPIAGISAGIPSKSASELIL).

6. A recombinant protein which is a *Clostridium* TcdA toxin protein (SEQ ID NO: 1) comprising a L1108K mutation.

7. A recombinant protein which is a *Clostridium* TcdB toxin protein (SEQ ID NO: 2) comprising a L1106K mutation.

8. A recombinant protein which is a *Clostridium* TcdA toxin protein (SEQ ID NO: 1) comprising mutations V1109S, N1110A, and N1111S.

9. A recombinant protein which is a *Clostridium* TcdB toxin protein (SEQ ID NO: 2) comprising mutations V1107S, N1108A, and N1109S.

10. The recombinant protein of claim 1, wherein epithelial cell toxicity is reduced by 100-fold or greater, or 1000-fold or greater compared to wild-type *Clostridium* toxin.

11. The recombinant protein of claim 1 comprising:
   a sequence of 75% or greater, 80% or greater, 85% or greater, 90% or greater, 95% or greater, or 99% or greater identity to residues 958 to 1130 of TcdA (SEQ ID NO: 1); or
   a sequence of 75% or greater, 80% or greater, 85% or greater, 90% or greater, 95% or greater, or 99% or greater identity to residues 956 to 1128 of TcdB (SEQ ID NO: 2).

12. The recombinant protein of claim 1 encoded by a sequence of 75% or greater, 80% or greater, 85% or greater, 90% or greater, 95% or greater, or 99% or greater identity to SEQ ID NO:4.

13. An immunogenic composition comprising a recombinant protein according to claim 1, and a pharmaceutically acceptable excipient.

14. A vaccine comprising the immunogenic composition of claim 13 and a pharmaceutically acceptable adjuvant.

* * * * *